US012778379B2

(12) United States Patent
Landon

(10) Patent No.: US 12,778,379 B2
(45) Date of Patent: Nov. 3, 2026

(54) VIDEOSCOPIC ARTHROSCOPIC INSTRUMENTS, DEVICES, AND SYSTEMS AND METHODS OF USE AND ASSEMBLY

(71) Applicant: RAFAEL MEDICAL DEVICES, LLC, Newark, NJ (US)

(72) Inventor: Ari Landon, Stamford, CT (US)

(73) Assignee: RAFAEL MEDICAL DEVICES, LLC, Newark, NJ (US)

( * ) Notice: Subject to any disclaimer, the term of this patent is extended or adjusted under 35 U.S.C. 154(b) by 611 days.

(21) Appl. No.: 17/660,152

(22) Filed: Apr. 21, 2022

(65) Prior Publication Data

US 2022/0346627 A1 Nov. 3, 2022

Related U.S. Application Data

(63) Continuation of application No. PCT/US2022/071013, filed on Mar. 7, 2022.

(60) Provisional application No. 63/200,402, filed on Mar. 5, 2021.

(51) Int. Cl.

| | |
|---|---|
| ***A61B 1/00*** | (2006.01) |
| ***A61B 17/32*** | (2006.01) |
| ***A61B 17/34*** | (2006.01) |

(52) U.S. Cl.

CPC ...... *A61B 1/00009* (2013.01); *A61B 1/00045* (2013.01); *A61B 1/00087* (2013.01); *A61B 17/320016* (2013.01); *A61B 17/3421* (2013.01)

(58) Field of Classification Search

CPC .............. A61B 1/0008; A61B 1/00087; A61B 1/00098; A61B 1/00101; A61B 1/00105; A61B 1/012; A61B 1/018; A61B 17/32; A61B 17/320016; A61B 17/320036; A61B 2017/32004; A61B 2017/320072; A61B 2017/320074; A61B 2017/320075; A61B 2017/320077; A61B 17/320092; A61B 2017/320093; A61B 1/317; A61B 17/3421; A61B 2017/320052; A61B 2017/320082; A61B 1/31; A61B 1/313-3137; A61B 2017/320028; A61B 2017/320032; A61B 1/00179; A61B 1/0676

USPC ................................ 600/104, 106–107, 129

See application file for complete search history.

(56) References Cited

U.S. PATENT DOCUMENTS

| | | | |
|---|---|---|---|
| 5,306,284 | A | 4/1994 | Agee |
| 7,628,798 | B1 | 12/2009 | Welborn |
| 7,918,784 | B2 | 4/2011 | Wellborn |
| 8,523,892 | B2 | 9/2013 | Rehnke |

(Continued)

OTHER PUBLICATIONS

International Search Report and Written Opinion of the International Searching Authority for PCT/US2022/071013, Jul. 14, 2022, 18 pages.

*Primary Examiner* — Ryan N Henderson
*Assistant Examiner* — Pamela F Wu
(74) *Attorney, Agent, or Firm* — Heslin Rothenberg Farley & Mesiti P.C.; Jacquelyn A. Graff, Esq.

(57) ABSTRACT

Videoscopic arthroscopic instruments, devices, and systems are disclosed. The videoscopic arthroscopic system includes a release instrument including at least one camera sensor and a video unit. In addition, methods of assembling the release instruments are disclosed. Further, surgical methods for using the videoscopic arthroscopic instruments, devices, and systems for minimally invasive tissue release surgery to release tissue in a patient's joints or limbs are disclosed.

17 Claims, 40 Drawing Sheets

(56) References Cited

U.S. PATENT DOCUMENTS

| | | | | |
|---|---|---|---|---|
| 8,951,273 | B1 | 2/2015 | Fard | |
| 8,992,424 | B2 | 3/2015 | Orbay | |
| 9,028,516 | B2 | 5/2015 | Palmer | |
| 9,254,122 | B2 | 2/2016 | Diao | |
| 9,271,637 | B2 | 3/2016 | Farr | |
| 2008/0195128 | A1* | 8/2008 | Orbay | A61B 1/00048 600/183 |
| 2009/0093677 | A1* | 4/2009 | Smith | A61B 17/3417 600/114 |
| 2010/0048994 | A1 | 2/2010 | Okoniewski | |
| 2010/0206099 | A1* | 8/2010 | Diao | A61B 17/295 73/866.5 |
| 2013/0317437 | A1* | 11/2013 | Cleveland | A61B 17/3209 604/164.01 |
| 2014/0320621 | A1 | 10/2014 | Sonnenschein et al. | |
| 2016/0270641 | A1 | 9/2016 | Mirza et al. | |
| 2016/0354105 | A1 | 12/2016 | Seymour | |
| 2017/0252056 | A1 | 9/2017 | Garvey et al. | |
| 2018/0338774 | A1 | 11/2018 | Pajardi et al. | |
| 2019/0159797 | A1 | 5/2019 | Seymour et al. | |
| 2019/0167293 | A1 | 6/2019 | Seymour et al. | |
| 2019/0374095 | A1 | 12/2019 | Lord et al. | |
| 2020/0046398 | A1 | 2/2020 | Mirza et al. | |
| 2020/0054193 | A1 | 2/2020 | Mirza et al. | |
| 2020/0078039 | A1 | 3/2020 | Mirza et al. | |
| 2020/0121347 | A1* | 4/2020 | Mirza | A61B 17/320036 |
| 2020/0155190 | A1 | 5/2020 | Basadonna et al. | |
| 2020/0197040 | A1 | 6/2020 | DaSilva | |
| 2020/0322538 | A1 | 10/2020 | Haggerty et al. | |
| 2022/0054160 | A1* | 2/2022 | Bernal | H04N 7/183 |

* cited by examiner

900

900

VIDEOSCOPIC ARTHROSCOPIC INSTRUMENTS, DEVICES, AND SYSTEMS AND METHODS OF USE AND ASSEMBLY

CROSS REFERENCE TO RELATED APPLICATION

This application is a continuation of PCT Application No. PCT/US2022/071013 filed Mar. 7, 2022 and entitled Videoscopic Arthroscopic Instruments, Devices, and Systems and Methods of Use and Assembly, which claims priority benefit under 35 U.S.C. § 119(e) of U.S. Provisional Application No. 63/200,402 filed Mar. 5, 2021 and entitled Videoscopic Arthroscopic Instruments, Devices, and Systems and Methods of Use and Assembly, which is hereby incorporated herein in its entirety.

FIELD OF THE INVENTION

The present invention relates generally to general surgery, such as instrumentation for endoscopic surgery. More specifically, but not exclusively, the present invention relates to instrumentation for minimally invasive tissue release surgery to release tissue in a patient's joints or limbs.

BACKGROUND OF THE INVENTION

As endoscopic tissue release procedures have become more common for various conditions, many of the instruments for the procedures have not allowed for full visualization of the anatomic structures during the procedure. Often a separate camera is inserted into the patient to provide visualization of the surgical procedure. Thus, improved instruments are needed for performing the tissue release procedures while allowing the surgeon to fully visualize the area that is being cut.

SUMMARY OF THE INVENTION

Aspects of the present invention provide videoscopic arthroscopic instruments, devices, and systems, as well as methods for using and assembling the videoscopic arthroscopic instruments, devices, and systems.

In one aspect, provided herein is a videoscopic arthroscopic system, including a release instrument with a blade and at least one camera sensor and wherein the blade and the at least one camera sensor translate together, and a video unit.

In another aspect, provided herein is a release instrument including a handpiece with a first end and a second end and a cannula with a first end and a second end, wherein the first end of the handpiece is slidingly received with the cannula. The handpiece including a body and a blade holder coupled to and extending out from a proximal end of the body, wherein a blade is coupled near a first end of the blade holder and at least one camera sensor is coupled to a bottom surface of a first end of the blade holder, and wherein the blade and at least one camera sensor translate together.

In yet another aspect, provided herein is another release instrument including a handpiece with a first end and a second end and a cannula with a first end and a second end, wherein the first end of the handpiece is slidingly received with the cannula. The handpiece including a body and a blade holder coupled to and extending out from a proximal end of the body, wherein the blade is coupled to a first end of the blade holder and the at least one camera sensor is coupled to the blade holder offset from the blade near the first end.

In a further aspect, provided herein is a surgical method including: obtaining a videoscopic arthroscopic system and creating an incision. The method also includes inserting a release instrument into the incision. In addition, the method includes using the integrated camera to position a blade adjacent to the tissue to be cut. The method also includes deploying the blade from the release instrument. In addition, the method may include translating the handpiece within the cannula to translate the blade to cut the tissue to be cut. Further, the method includes removing the release instrument and completing the procedure.

In yet another aspect, provided herein is a method of assembling a release instrument, including: coupling a moveable blade to a handpiece. The method also includes coupling a camera unit to the handpiece near the first end. In addition, the method includes inserting a translating member into the handpiece near a second end. Further, the method includes connecting the translating member to the moveable blade. Finally, the method includes inserting the first end of the handpiece into a second end of a cannula.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
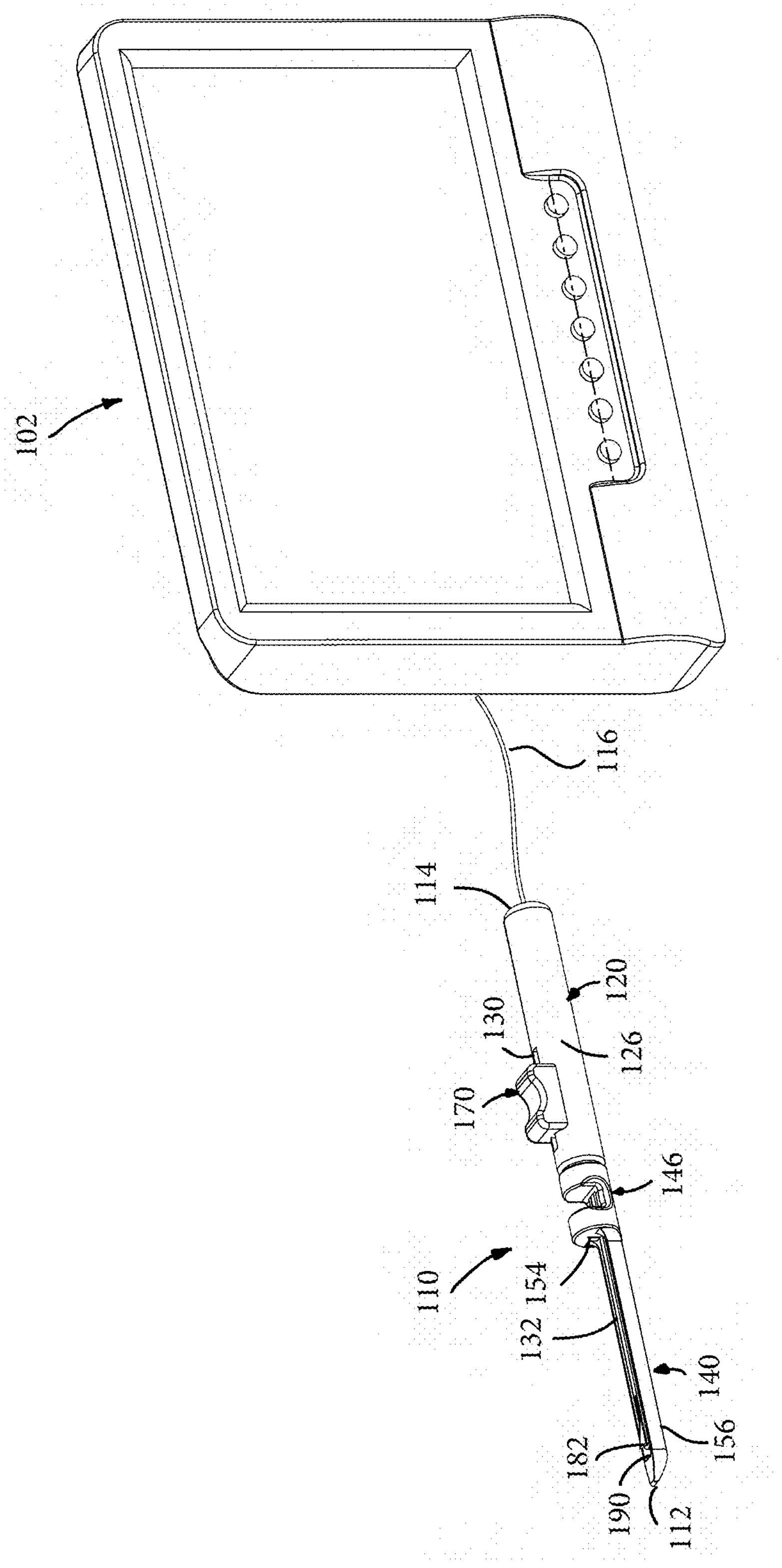
FIG. 1 is a perspective view of one embodiment of a videoscopic arthroscopic system, in accordance with an aspect of the present disclosure.

Generally stated, disclosed herein are videoscopic arthroscopic instruments, devices, and systems. Further, a method of assembly and a surgical method for using the videoscopic arthroscopic instruments, devices, and systems are discussed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current devices and methods are described herein with reference to use with the bones and anatomical structures of the hand, the bones of the hand, wrist and lower arm may be used to describe the surfaces, positions, directions or orientations of the devices, instrumentation, and methods. Further, the instruments and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the instruments and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the instruments and methods, and the aspects, components, features and the like thereof, described herein with respect to a right hand may be mirrored so that they likewise function with a left hand and vice versa. Further, the instruments and methods, and the aspects, components, features and the like thereof, disclosed herein are described with respect to the hand for brevity purposes, but it should be understood that the devices and methods may be used with other bones of the body having similar structures, for example the elbow or the lower extremity, and more specifically, with the bones of the ankle, foot, and leg.

Referring to the drawings, wherein like reference numerals are used to indicate like or analogous components throughout the several views, and with particular reference to FIGS. 1-13, there are illustrated the instruments and devices of the videoscopic arthroscopic system 100. One embodiment of the system 100 may include, for example, a release instrument 110 and a video unit 102. The release instrument 110 may be, for example, a videoscopic, single-use, disposable, arthroscopic instrument for minimally invasive, endoscopic, tissue release surgery in a patient's joints or limbs. Specifically, the instrument 110 may be used for tissue release procedures in the wrist, foot, and elbow for cutting tendinous, ligamentous, fibrous tissue, and the like. The release instrument 110 may include a first end 112 and a second end 114. The second end 114 of the release instrument 110 may include a cable 116 extending from the release instrument 110 and to a video unit 102. The video unit 102 may be, for example, a video display, such as a tablet, video screen, television, and the like, or a video processor that may be separate from or integral with a video display.

With continued reference to FIGS. 1-13, the instrument 110 may include a handpiece or housing 120 and a cannula 140. A portion of the handpiece 120 may be slidingly received within the cannula 140. The handpiece 120 may include a first end 122 and a second end 124 opposite the first end 122. The cannula 140 may engage the handpiece 120 at the first end 122. The cable 116 of the system 100 may be coupled to and extend away from the second end 124 of the handpiece 120.

The handpiece 120 may also include a body 126 extending from the second end 124 toward the first end 122, a sheath or blade housing 132 extending from the body 126 to the first end 122, an actuating blade, blade switch or translating member 170 moveably coupled to the body 126, a blade 182 coupled near the first end 122 of the handpiece 120, and a camera or camera sensor 194 coupled near the first end 122 of the handpiece 120, as shown in FIGS. 6-8 and 11-12. The actuating blade 170 and camera sensor 194 may be, for example, embedded into the handpiece 120. The handpiece 120 may, for example, optionally include at least one light member 196, 198, such as a light-emitting diode ("LED").

In addition, the body 126 may include a proximal end 128 at the end opposite the second end 124 of the handpiece 120. The body 126 may have, for example, a cylindrical shape or alternatively, the handpiece 120 may have a pencil shape, gun shape, or a shape to match the shape of a palm. The body 126 may be, for example, a singular integral or monolithic piece (i.e., of one-piece construction), or may be formed from a plurality of components that are coupled (e.g., rigidly coupled) together to form the body 126 of the handpiece 120. For example, the body 126 may include a first housing and a second housing coupled together to form the body 126. The body 126 may also include a first slot or interior track 130 positioned near the proximal end 128 of the body 126. The first slot 130 may, for example, extend along a portion of the longitudinal axis of the body 126, which extends between the proximal end 128 and the second end 124. The first slot 130 may extend, for example, only along a portion of the body 126 between the proximal end 128 and the second end 124. The first slot 130 may, for example, extend into the body 126, for example, toward a portion of the body 126 opposite the opening in the exterior surface of the body 126. The first slot 130 may extend, for example, from the exterior surface toward a central axis of the body 126. The first slot 130 may be, for example, sized and shaped to receive a portion of the blade switch or translating member 170.

Figure 2:
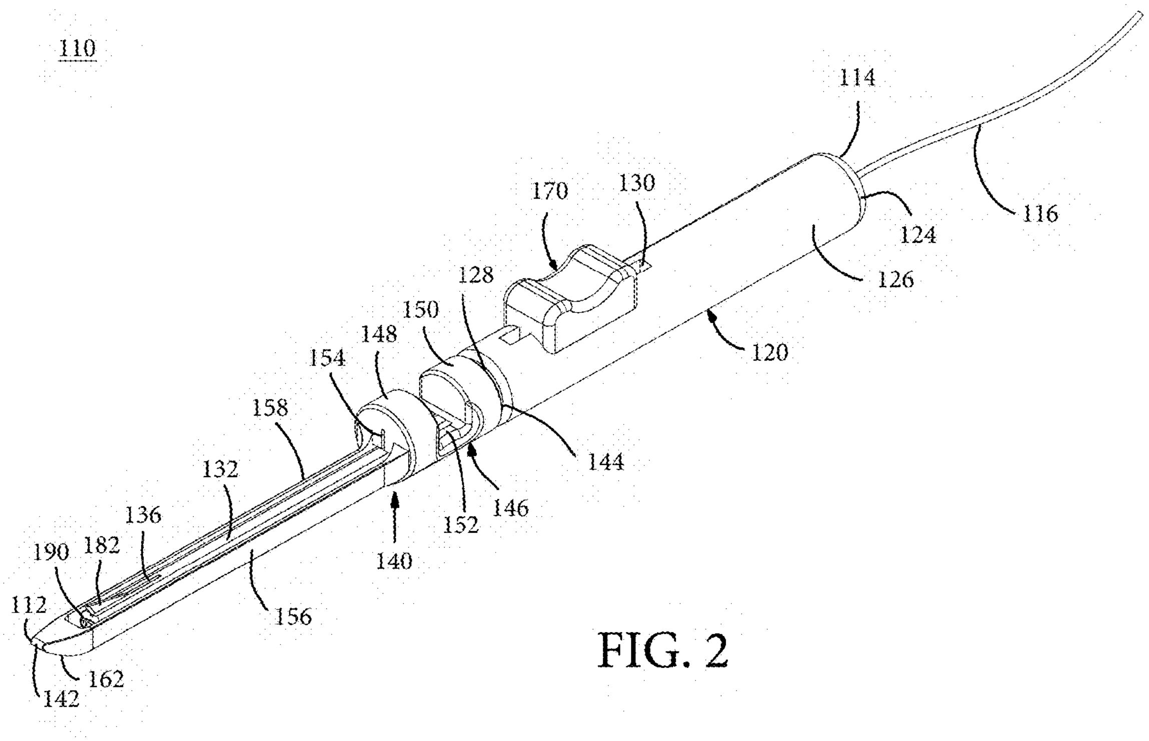
FIG. 2 is a perspective view of a release instrument of the videoscopic arthroscopic system of FIG. 1 in a deployed position, in accordance with an aspect of the present disclosure.
Figure 3:
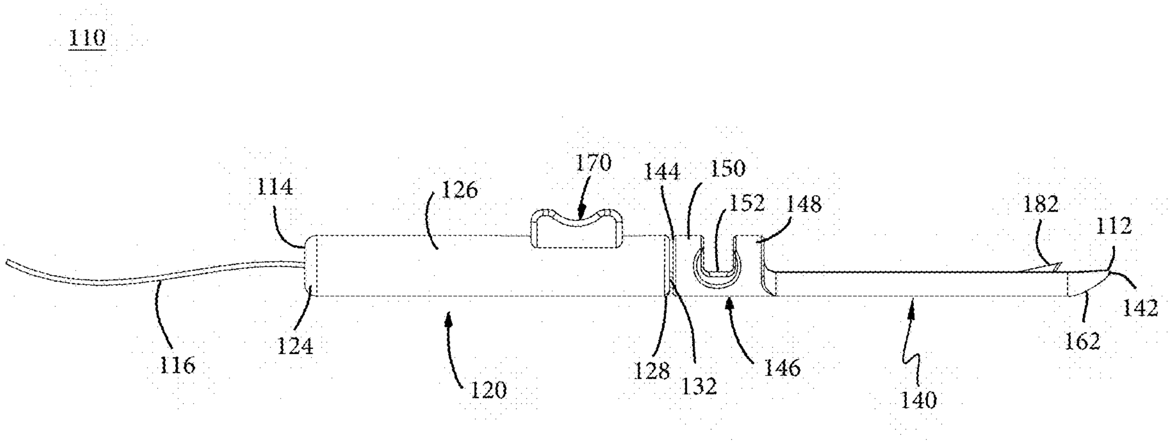
FIG. 3 is a side view of the release instrument of FIG. 2, in accordance with an aspect of the present disclosure.
Figure 4:
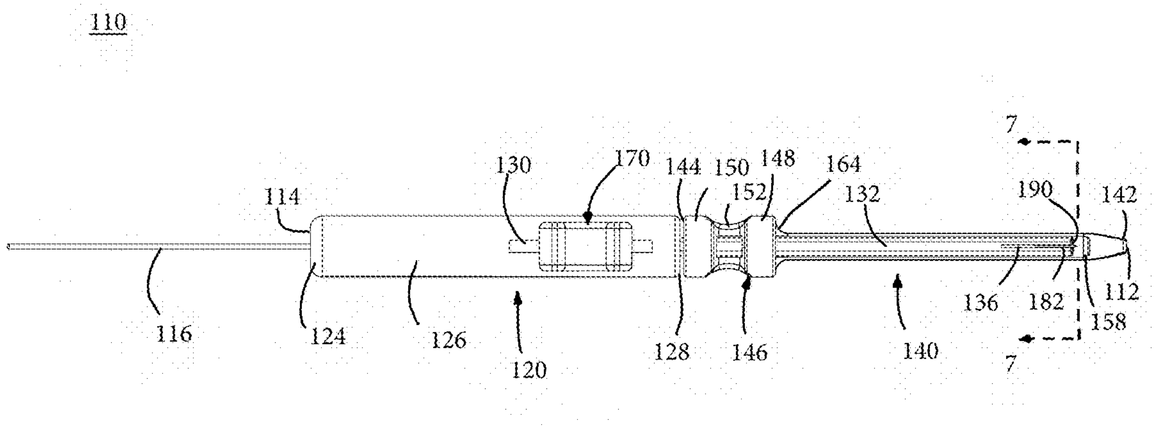
FIG. 4 is a top view of the release instrument of FIG. 2, in accordance with an aspect of the present disclosure.
Figure 5:
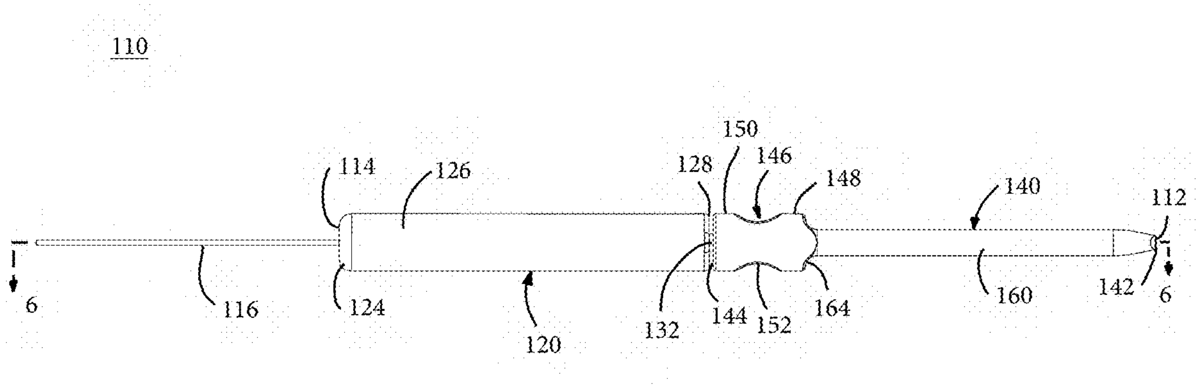
FIG. 5 is a bottom view of the release instrument of FIG. 2, in accordance with an aspect of the present disclosure.
Figure 6:
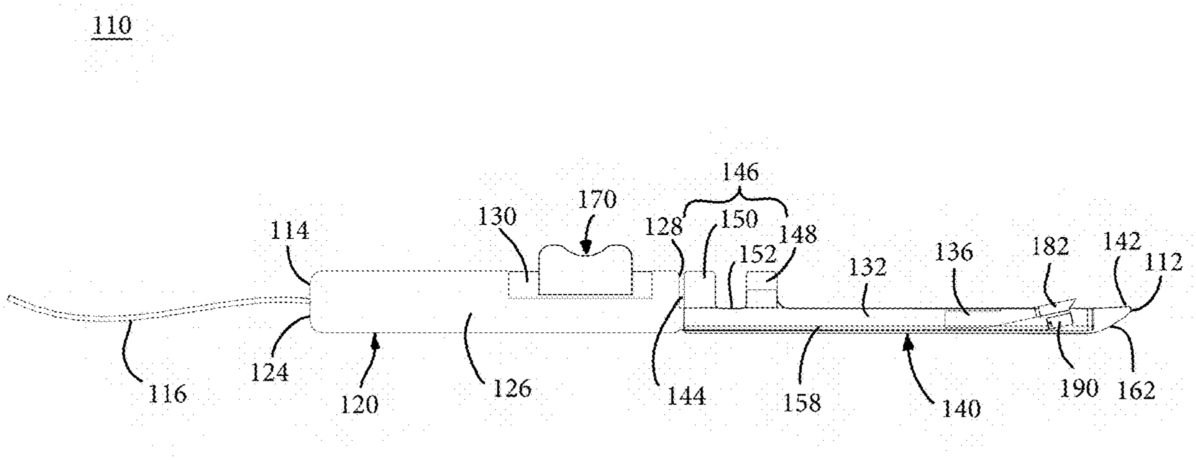
FIG. 6 is a cross-sectional side view of the release instrument of FIG. 2 taken along line 6-6 in FIG. 5, in accordance with an aspect of the present disclosure.
Figure 7:
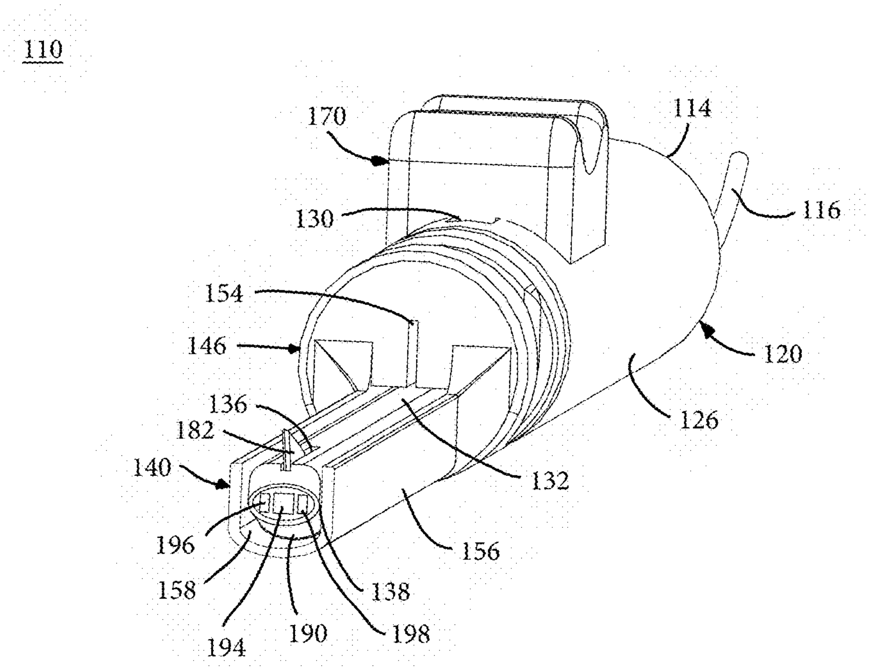
FIG. 7 is a cross-sectional front view of the release instrument of FIG. 2 taken along line 7-7 in FIG. 4, in accordance with an aspect of the present disclosure.
Figure 8:
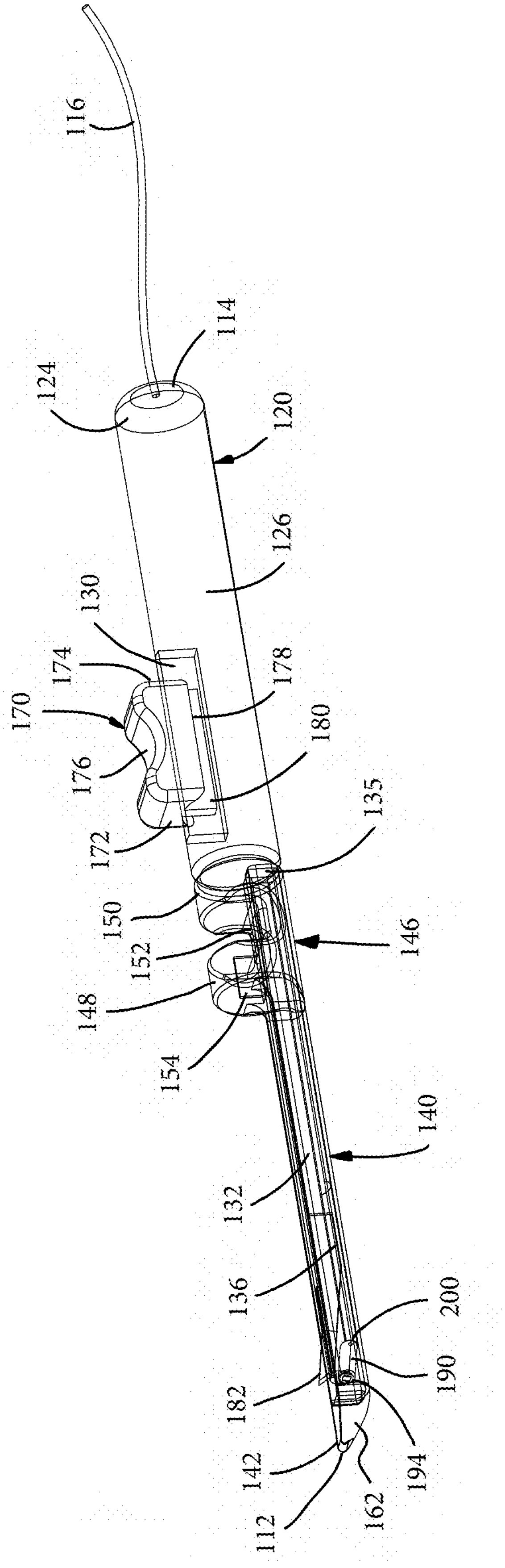
FIG. 8 is a perspective view of the release instrument of FIG. 2 with a transparent handpiece and cannula, in accordance with an aspect of the present disclosure.
Figure 10:
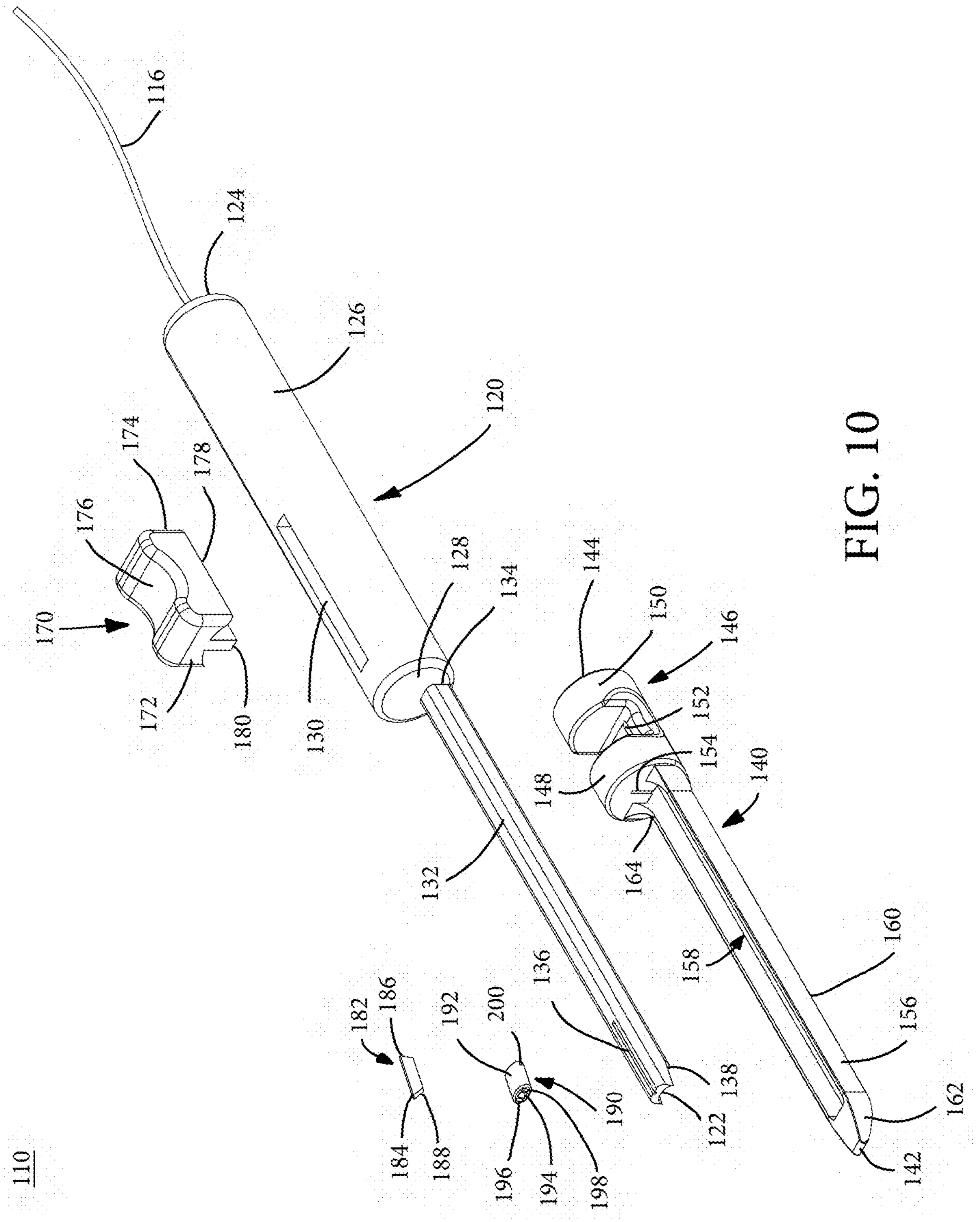
FIG. 10 is an exploded, perspective view of the release instrument of FIG. 2, in accordance with an aspect of the present disclosure.

The sheath 132 may include a coupling end or distal end 134 that engages the proximal end 128 of the body 126. The sheath 132 may be coupled to, for example, an outer portion of the proximal end 128 offset from the central axis of the body 126. As shown in FIG. 2, the coupling end 134 of the sheath 132 may be coupled to the body 126 and include at least one opening 135 to allow for, for example, at least one wire and/or cable to extend from the camera sensor 194 and/or light members 196, 198 through the body 126 to the cable 116 to transmit power to the camera sensor 194 and/or light members 196, 198 and/or video to a display or a processor of the video unit 102. The at least one wire and/or cable may be, for example, a single wire or separate wires for the camera sensor 194 and light members 196, 198. The sheath 132 may also include a second slot 136 positioned near the first end 122 of the handpiece 120. The second slot 136 may extend from the first end 122 toward the second end 124 along a longitudinal axis extending between the first end 122 and the second end 124. The second slot 136 may also extend into the sheath 132 from a top surface of the sheath 132 toward a bottom surface. As shown in FIG. 7, the sheath 132 may have, for example, a square or rectangular cross-section taken perpendicular to the longitudinal axis of the sheath 132 along a majority of the length of the sheath 132. The sheath 132 may have, for example, rounded corners along the length of the sheath 132. The sheath 132 may also have a leading end portion 138 at the first end 122 of the handpiece 120. The leading end portion 138 may be, for example, tapered, curved, or stepped as it extends from the bottom surface toward the top surface. In addition, the leading end portion 138 may be, for example, curved between a first or right side and a second or left side, as shown in FIGS. 7 and 10.

The cannula 140 may include a first end 142 and a second end 144 opposite the first end 142. The cannula 140 may also include a base 146 and an extension member 156 coupled to and extending from the base 146. The base 146 may include a first portion 148, a second portion 150, and a recessed region 152 positioned between the first portion 148 and the second portion 150. The second portion 150 may extend from the second end 144 toward the first end 142. The first and second portions 148, 150 may be shaped, for example, as a cylinder or elliptical cylinder. The recessed region 152 may have, for example, a half cylindrical or half elliptical cylinder shape. The first and second portions 148, 150 may have, for example, the same width as the portions 148, 150 extend along a direction from the first end 142 to the second end 144. In an alternative embodiment, the first and second portions 148, 150 may have different widths. The recessed region 152 may have, for example, a width that is the same, larger, or smaller than the width of the first and second portions 148, 150. The recessed region 152 may have, for example, a width that allows for the blade 182 to be fully positioned within the recessed region 152 when in the extended or deployed position. In an alternative embodiment, the recessed region 152 may be used, for example, to join the cannula 140 to the handpiece 120 and/or as a grip or pinch feature to facilitate separation of the cannula 140 from the handpiece 120. The first portion 148 may also have a cavity or slot 154 extending through the first portion 148 along the direction from the first end 142 to the second end 144, as shown in FIGS. 1, 2, 7-8 and 10-11. The cavity 154 may be, for example, an elongated rectangular shaped cavity 154. The cavity 154 may be, for example, sized and shaped to allow for the extended or deployed blade 182 to pass through during the release procedure.

The extension member 156 may be, for example, coupled to a lower portion of the first portion 148 of the base 146. The extension member 156 may be, for example, positioned aligned with the recessed region 152 of the base 146. The extension member 156 may extend from the first portion 148 to the first end 142 of the cannula 140. The extension member 156 may include a channel 158 extending into the extension member 156 from a top surface toward a bottom surface 160 of the extension member 156. The channel 158 may also extend from the first portion 148 to a positioned near the first end 142 of the cannula 140. The first end 142 of the cannula 140 may have a leading end 162. The leading end 162 may be, for example, tapered or curved from a bottom surface 160 toward the top surface and from the first and second side surfaces to a tip at the end of the first end 142. The extension member 156 may also include a coupling end or distal end 164 securing the extension member 156 to the base 146. The coupling end 164 may include, for example, a curve or taper from the exterior side surfaces of the extension member 156 to the first portion 148 of the base 146. The extension member 156 may have, for example, a width between the first side and the second side and the width of the extension member 156 may be smaller than the diameter of the first portion 148.

At least a portion of the cannula 140 may be, for example, clear or opaque. For example, the cannula 140 may be made of a transparent plastic, such as, polycarbonate or a more rigid opaque polyarylamide. When at least a portion of the cannula 140 is clear, the camera sensor 194 may allow for visualization not only through the channel 158 of the cannula 140, but also through that clear portion of the extension member 156.

Figure 9:
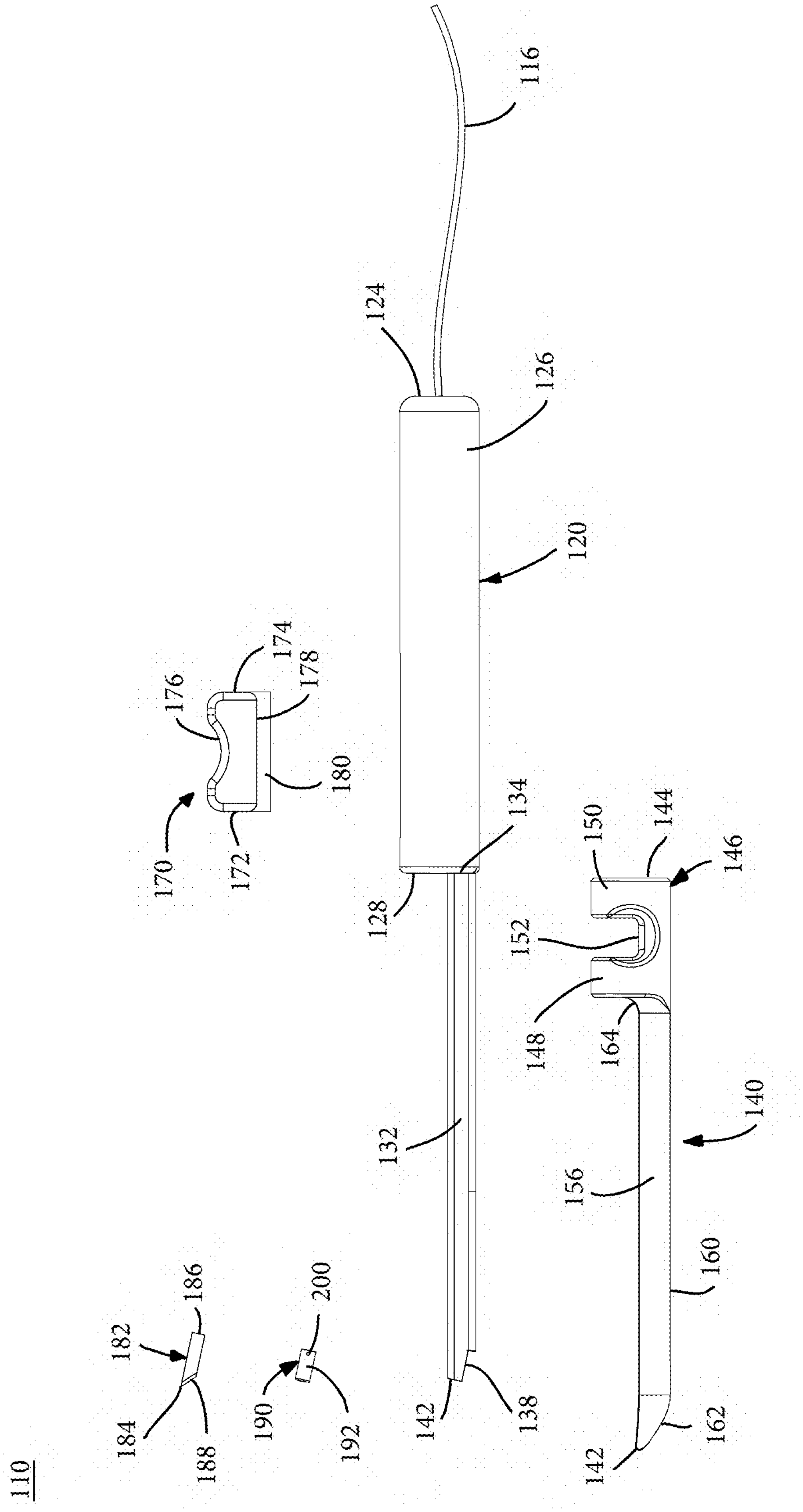
FIG. 9 is an exploded, side view of the release instrument of FIG. 2, in accordance with an aspect of the present disclosure.
Figure 11:
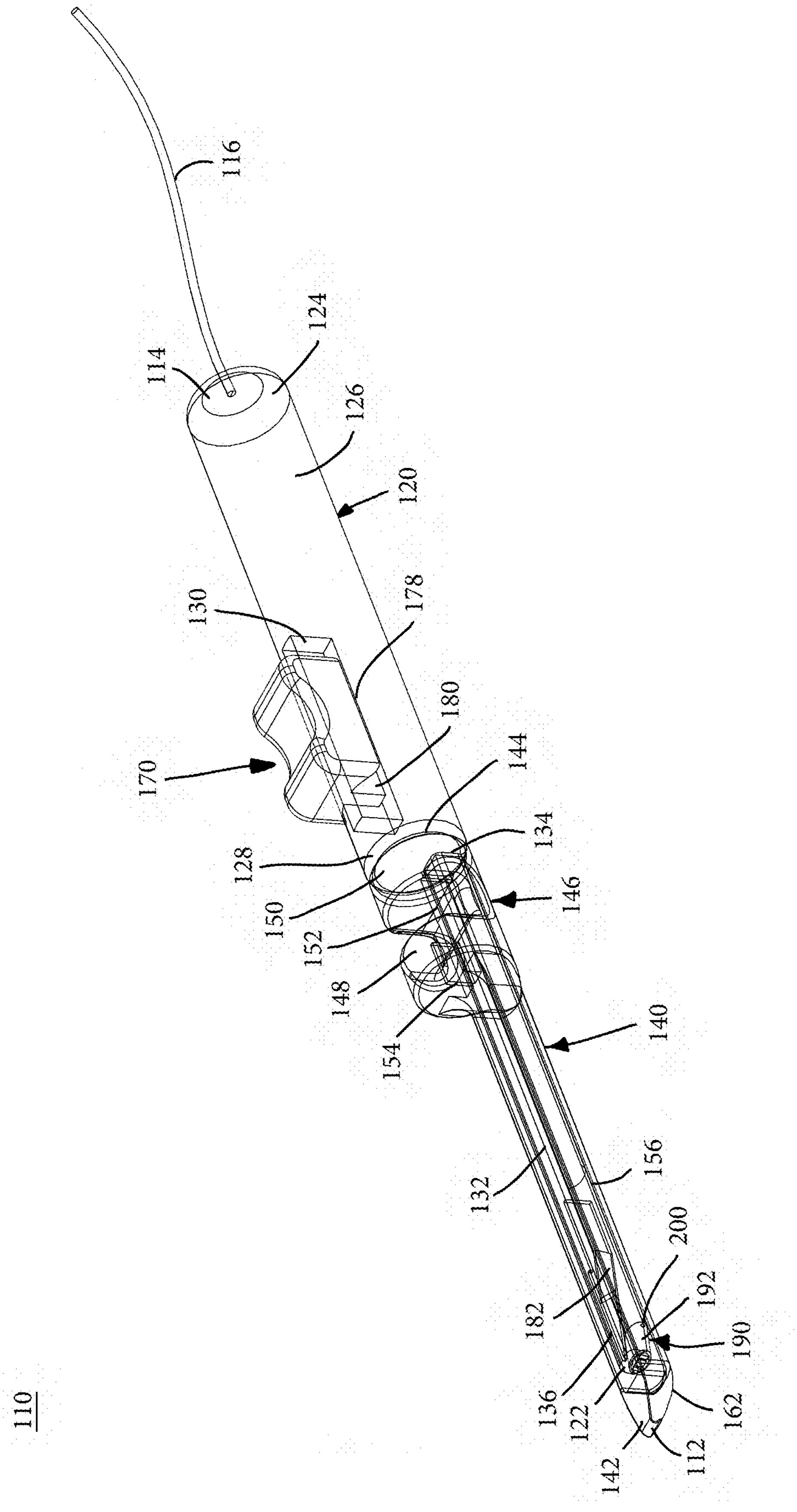
FIG. 11 is a perspective view of the release instrument of FIG. 2 with a transparent handpiece and a transparent cannula in an undeployed position, in accordance with an aspect of the present disclosure.

As shown in at least FIGS. 9-12, the blade switch or translating member 170 includes a first end 172 and a second end 174 opposite the first end 172. The translating member 170 may also include a top surface 176 with, for example, a grooved region or recessed region to assist with gripping and moving the translating member 170. The translating member 170 may also include a bottom surface 178 generally opposite the top surface 176. The bottom surface 178 may be, for example, curved or arced between a first side and a second side of the translating member 170. The curve or arc of the bottom surface 178 may be shaped, for example, to match the curve or arch of the exterior surface of the body 126 of the handpiece 120. The bottom surface 178 of the translating member 170 may also include a protrusion or fin 180 extending away from the bottom surface 178. The protrusion or fin 180 may extend, for example, from the first end 172 to the second end 174 of the translating member 170 along the entire length of the translating member 170. The protrusion 180 may, for example, extend beyond the lowest point of the bottom surface 178 of the translating member 178, as shown in FIGS. 9, 10, and 11. The protrusion 180 may be, for example, positioned midway between a first side and a second side of the translating member 170.

Figure 12:
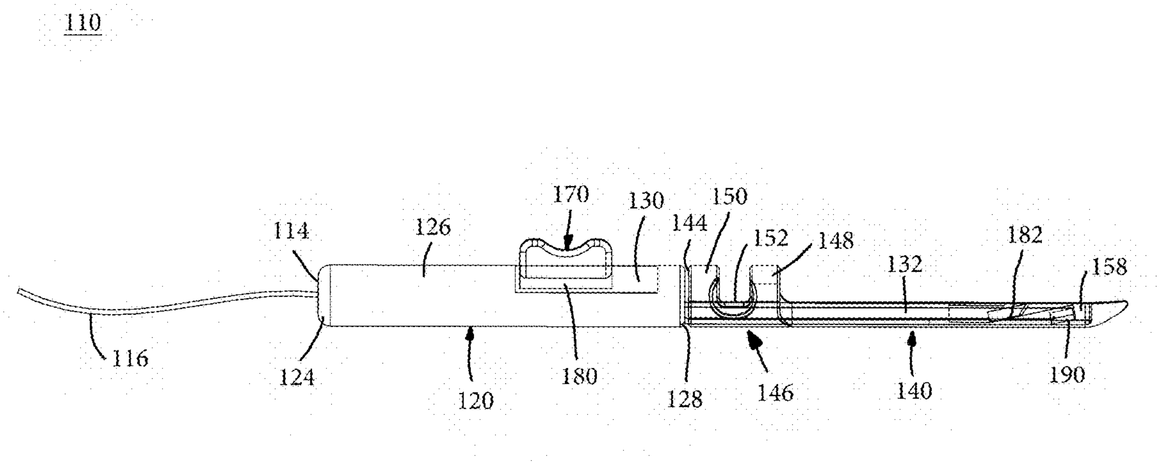
FIG. 12 is a side view of the release instrument of FIG. 11, in accordance with an aspect of the present disclosure.
Figure 13:
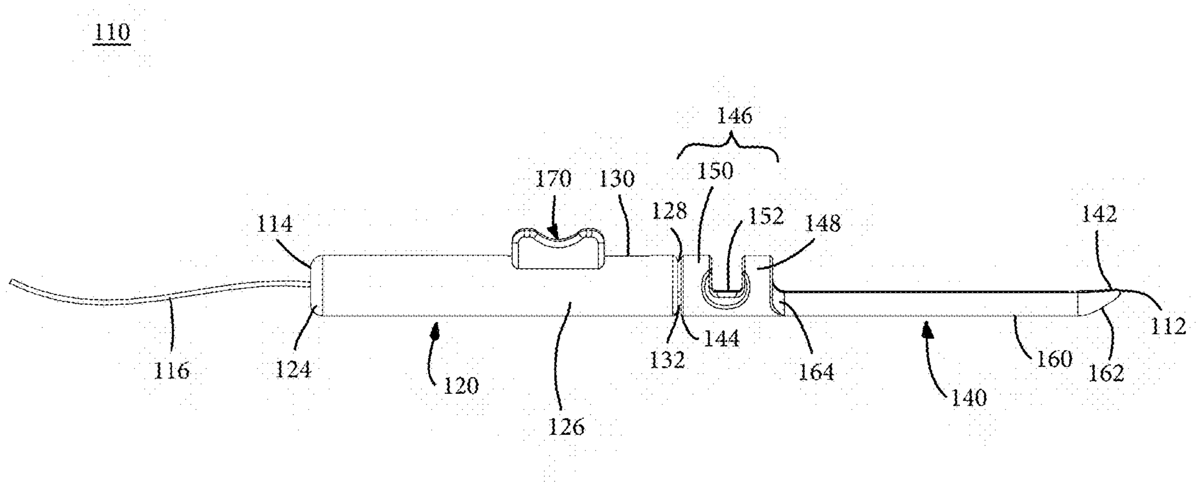
FIG. 13 is a side view of the release instrument of FIG. 2 in an undeployed position, in accordance with an aspect of the present disclosure.

As best seen in FIGS. 1-3 and 6-12, the blade 182 may include a first end 184 and a second end 186 opposite the first end 184. The blade 182 may include a cutting tip 188 at the first end 184. The cutting tip 188 may be, for example, angled from a top surface to a bottom surface of the blade 182. The blade 182 may be, for example, moveably positioned within the second slot 136 of the sheath 132 of the handpiece 120. The blade 182 may be coupled to the translating member 170 with, for example, a wire to allow for translation or sliding of the blade 182 within the second slot 136. The wire may be, for example, coupled to a portion of the blade 182 at one end and a second end of the wire may be directly or indirectly coupled to a portion of the protrusion 180. The blade 182 may move from a first insertion position with the blade 182 positioned fully within the second slot 136 and below a top surface of the sheath 132, as shown in FIGS. 12-13, to a second deployed position with at least a portion of the blade 182 extending above a top surface of the sheath 132, as shown in FIGS. 1-3 and 6-8. The translating member 170 may be, for example, slid toward the first end 112 of the release instrument 110 to deploy the blade 182 and extend at least a portion of the blade 182 above a top surface of the sheath 132, specifically, at least a portion of the cutting tip 188 of the blade 182. In addition, the translating member 170 may be, for example, slid toward the second end 114 of the release instrument 110 to retract the blade 182 back into the second slot 136 and position the entire cutting tip 188 of the blade 182 below the top surface of the sheath 132.

The camera unit 190 may be, for example, a singular integral or monolithic piece (i.e., of one-piece construction) with the handpiece 120, or the camera unit 190 may be formed with the sheath 132 as a plurality of components that are coupled (e.g., rigidly coupled) together to form a handpiece 120 with a camera unit 190. The camera unit 190 may be coupled to the sheath 132 at the leading end portion 138 on a bottom surface. The exterior surface of the camera unit 190 may be, for example, sized and shaped to match the bottom surface of the leading end portion 138. For example, the housing 192 of the camera unit 190 may have a coupling portion 200 for securing the camera unit 190 to the leading end portion 138 of the headpiece 120. The first end of the camera unit 190 may be positioned, for example, flush with or protruding from the first end 122 of the handpiece 120. In an alternative embodiment, the leading end portion 138 could include an opening for embedding the camera unit 190 into the first end 122 of the handpiece 120. The release instrument 110 may also include a rasp feature (not shown) positioned at the first end of the camera unit 190 to move fascia and other tissue away from the first end of the camera unit 190 and to maintain a clear visualization of the blade path.

The camera unit 190 may also have a camera sensor 194, such as a complementary metal-oxide-semiconductor ("CMOS") sensor positioned on a first end of the camera unit 190. In addition, the camera unit 190 may include, for example, at least one light member, illumination fibers, or illumination LED 196, 198. The at least one light member 196, 198 may be, for example, a first light member 196 positioned on a first side of the camera sensor 194 and a second light member 198 positioned on a second side of the camera sensor 194 at the first end of the camera unit 190. The camera sensor 194 and light members 196, 198 may be, for example, positioned adjacent to the blade 182 at the first end 122 of the handpiece 120, as best seen in FIG. 7. The coupling portion 200 may allow for the camera unit 190 to be fixed or to allow for movement of the camera unit 190, for example, rotation or pivoting of the camera unit 190 relative to the leading end portion 138 of the sheath 132. Alternative, coupling portions 200 are also contemplated to allow for rotation or pivoting of the camera unit 190 in all directions about the point of attachment of the coupling portion 200 to the sheath 132.

The release instrument 110 may be assembled by inserting the blade 182 into the second slot 136 of the sheath 132 in an undeployed position. The camera unit 190 may also be secured to the leading end portion 138 of the sheath 132. In addition, the translating member 170 may be inserted into the first slot 130 of the body 126 and the protrusion 180 coupled directly or indirectly to the blade 182 to allow for translation of the blade 182 as the translating member 170 is moved or translated. Then, the first end 122 of the sheath 132 of the handpiece 120 may be inserted into the second end 144 of the cannula 140. The sheath 132 may then be slid along the channel 158 of the cannula 140.

Referring now to FIGS. 14-26, a retrograde videoscopic arthroscopic system 250 is shown. One embodiment of the system 250 may include, for example, a release instrument 260 and a video unit 102. The release instrument 260 may be, for example, a videoscopic, single-use, disposable, arthroscopic instrument for minimally invasive, endoscopic, tissue release surgery in a patient's joints or limbs. Specifically, the instrument 260 may be used for tissue release procedures in the wrist, foot, and elbow for cutting tendinous, ligamentous, fibrous tissue, and the like. The release instrument 260 may include a first end 262 and a second end 264. The second end 264 of the release instrument 260 may include a cable 252 extending from the release instrument 260 to a video unit 102.

With continued reference to FIGS. 14-26, the instrument 260 may include a handpiece or housing 270 and a cannula 140. A portion of the handpiece 120 may be slidingly received within the cannula 140. The cannula 140 may be as described above with reference to release instrument 110 and which will not be described again here for brevity's sake. The handpiece 270 may include a first end 272 and a second end 274 opposite the first end 272. The cannula 140 may engage the handpiece 270 at the first end 272. The cable 252 of the system 250 may be coupled to and extend away from the second end 274 of the handpiece 270.

The handpiece 270 may also include a body 276 extending from the second end 274 toward the first end 272, an arm member or blade housing 282 extending from the body 276 to the first end 272, an actuating blade, blade switch or translating member 170 moveably coupled to the body 276, a blade 300 coupled near the first end 272 of the handpiece 270, and a camera or camera sensor 194 coupled near the first end 272 of the handpiece 270, as shown in FIGS. 19-21 and 24-25. The translating member 170 and camera unit 190 may be, for example, embedded into the handpiece 270. The translating member 170 and camera unit 190, including camera sensor 194 and light members 196, 198, may be as described in greater detail above with reference to release instrument 110, which will not be described again here for brevity's sake.

In addition, the body 276 may include a proximal end 278 at the end opposite the second end 274 of the handpiece 270. The body 276 may have, for example, a cylindrical shape or alternatively, the handpiece 270 may have a pencil shape, gun shape, or a shape to match the shape of a palm. The body 276 may be, for example, a singular integral or monolithic piece (i.e., of one-piece construction), or may be formed from a plurality of components that are coupled (e.g., rigidly coupled) together to form the body 276 of the handpiece 270. For example, the body 276 may include a first housing and a second housing coupled together to form the body 276. The body 276 may also include a first slot or interior track 280 positioned near the proximal end 278 of the body 276. The first slot 280 may, for example, extend along a portion of the longitudinal axis of the body 276, which extends between the proximal end 278 and the second end 274. The first slot 280 may extend, for example, only along a portion of the body 276 between the proximal end 278 and the second end 274. The first slot 280 may, for example, extend into the body 276, for example, toward a portion of the body 276 opposite the opening in the exterior surface of the body 276. The first slot 280 may extend, for example, from the exterior surface toward a central axis of the body 276. The first slot 280 may be, for example, sized and shaped to receive a portion of the blade switch or translating member 170.

Figure 21:
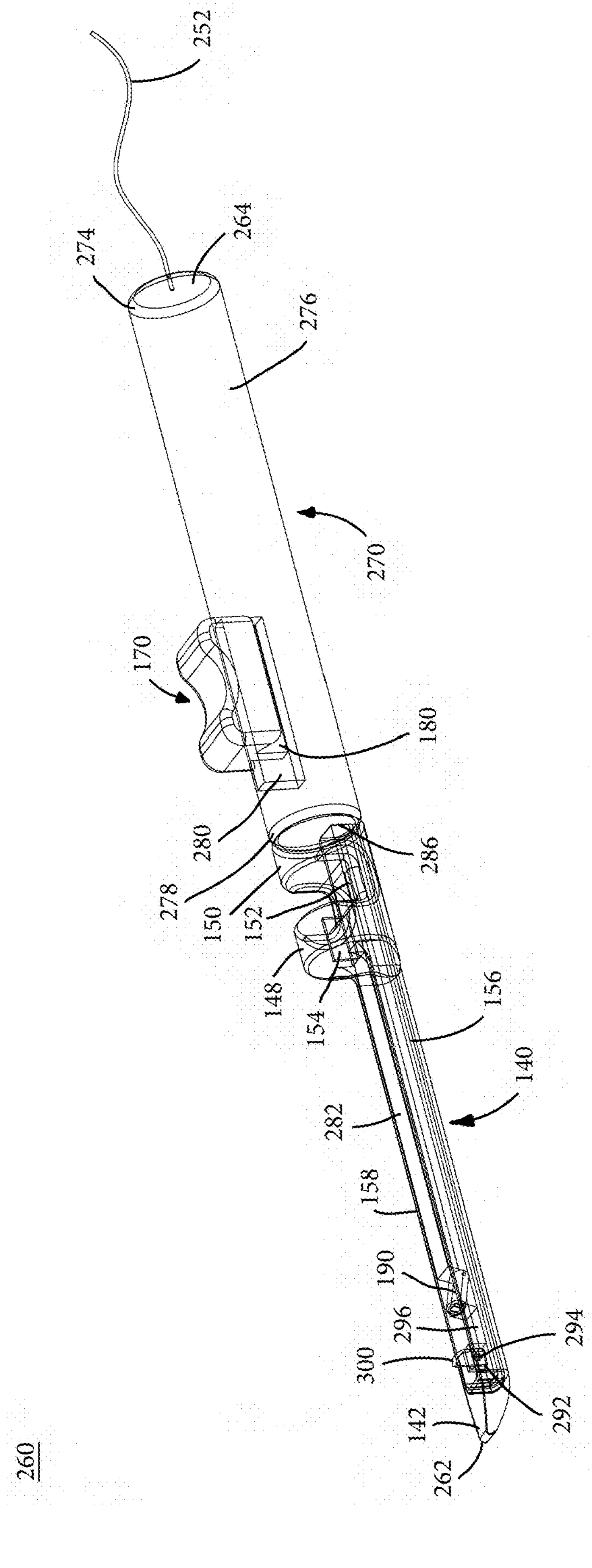
FIG. 21 is a perspective view of the release instrument of FIG. 15 with a transparent handpiece and cannula, in accordance with an aspect of the present disclosure.
Figure 22:
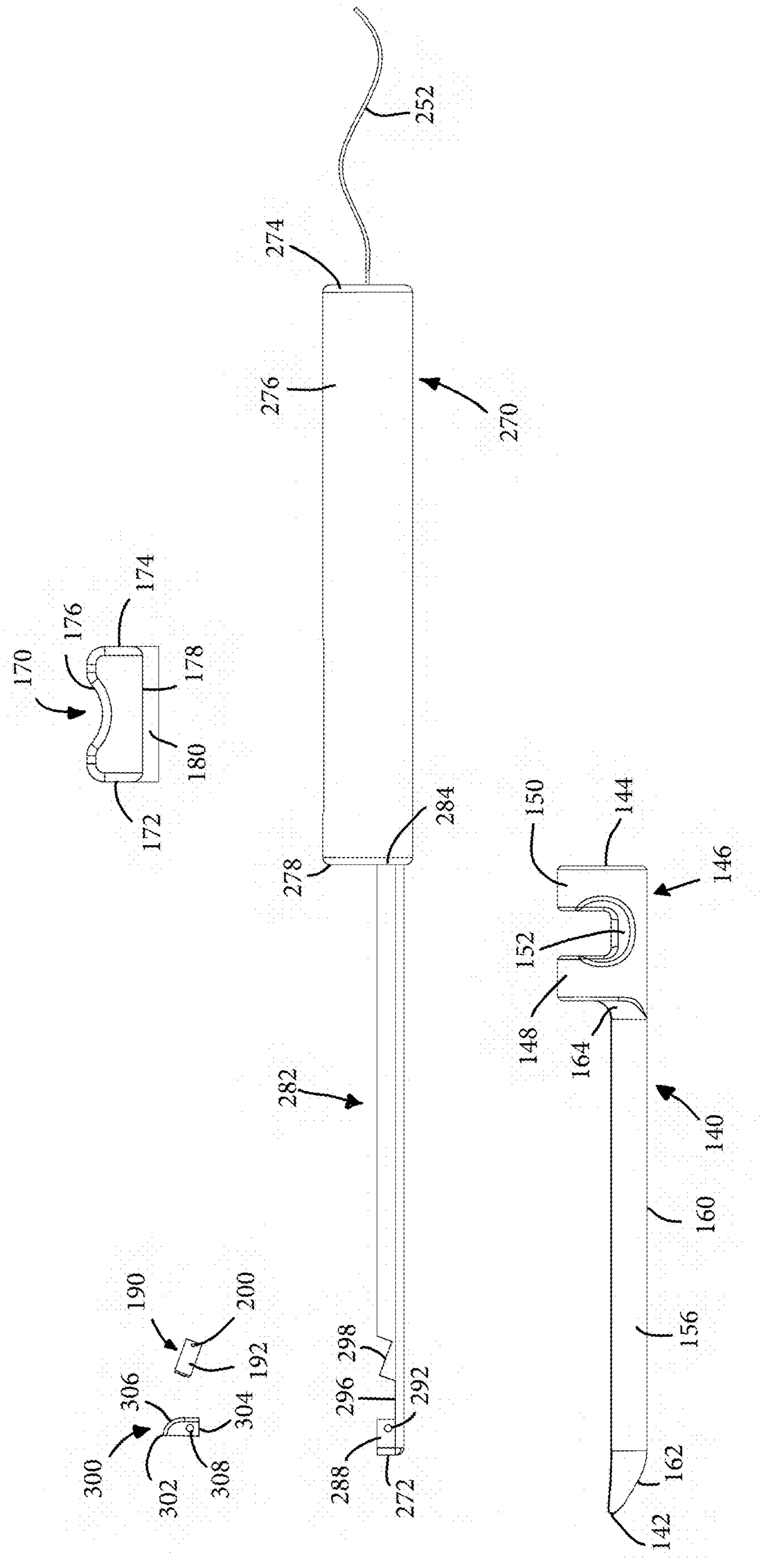
FIG. 22 is an exploded, side view of the release instrument of FIG. 15, in accordance with an aspect of the present disclosure.
Figure 23:
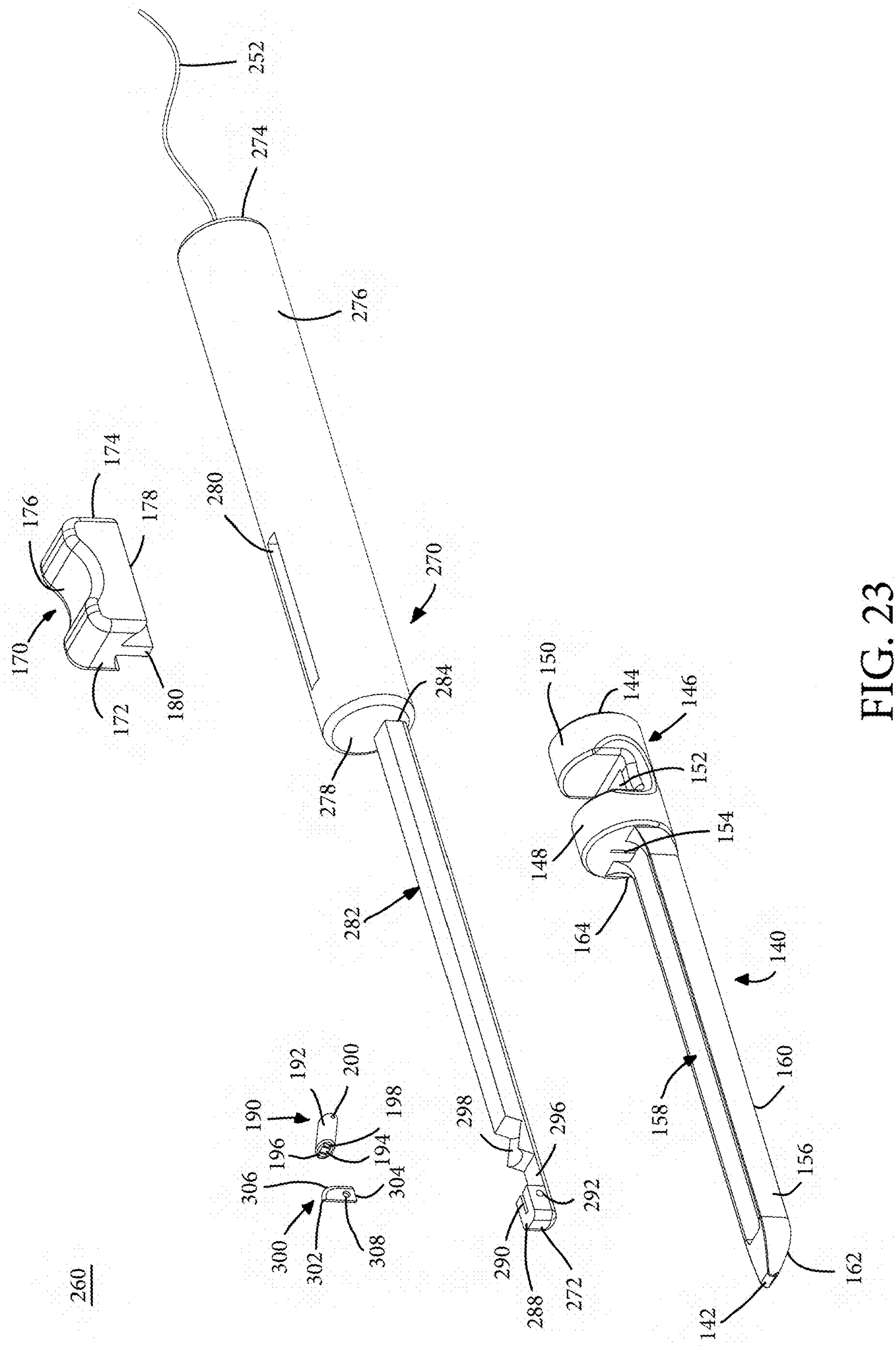
FIG. 23 is an exploded, perspective view of the release instrument of FIG. 15, in accordance with an aspect of the present disclosure.

As shown in FIGS. 22-23, the arm member 282 may include a coupling end or distal end 284 that engages the proximal end 278 of the body 276. The arm member 282 may be coupled to, for example, an outer portion of the proximal end 278 offset from the central axis of the body 276. As shown in FIG. 21, the coupling end 284 of the arm member 282 may be coupled to the body 276 and include at least one opening 286 to allow for, for example, at least one wire and/or cable to extend from the camera sensor 194 and/or light member 196, 198 through the body 276 to the cable 252 to transmit power to the camera sensor 194 and/or light members 196, 198 and/or video to a display or a processor of the video unit 102. The at least one wire and/or cable may be, for example, a single wire or separate wires for the camera sensor 194 and light members 196, 198. The arm member 282 may have, for example, a polygonal shape along a majority of its length, such as a rectangular or square shape. The arm member 282 may also include a blade housing 288 extending from the first end 272 of the handpiece 270 toward the distal end 284 of the arm member 282. The blade housing 288 may also have, for example, a polygonal cross-sectional shape, such as a rectangular or square cross-sectional shape.

Figure 24:
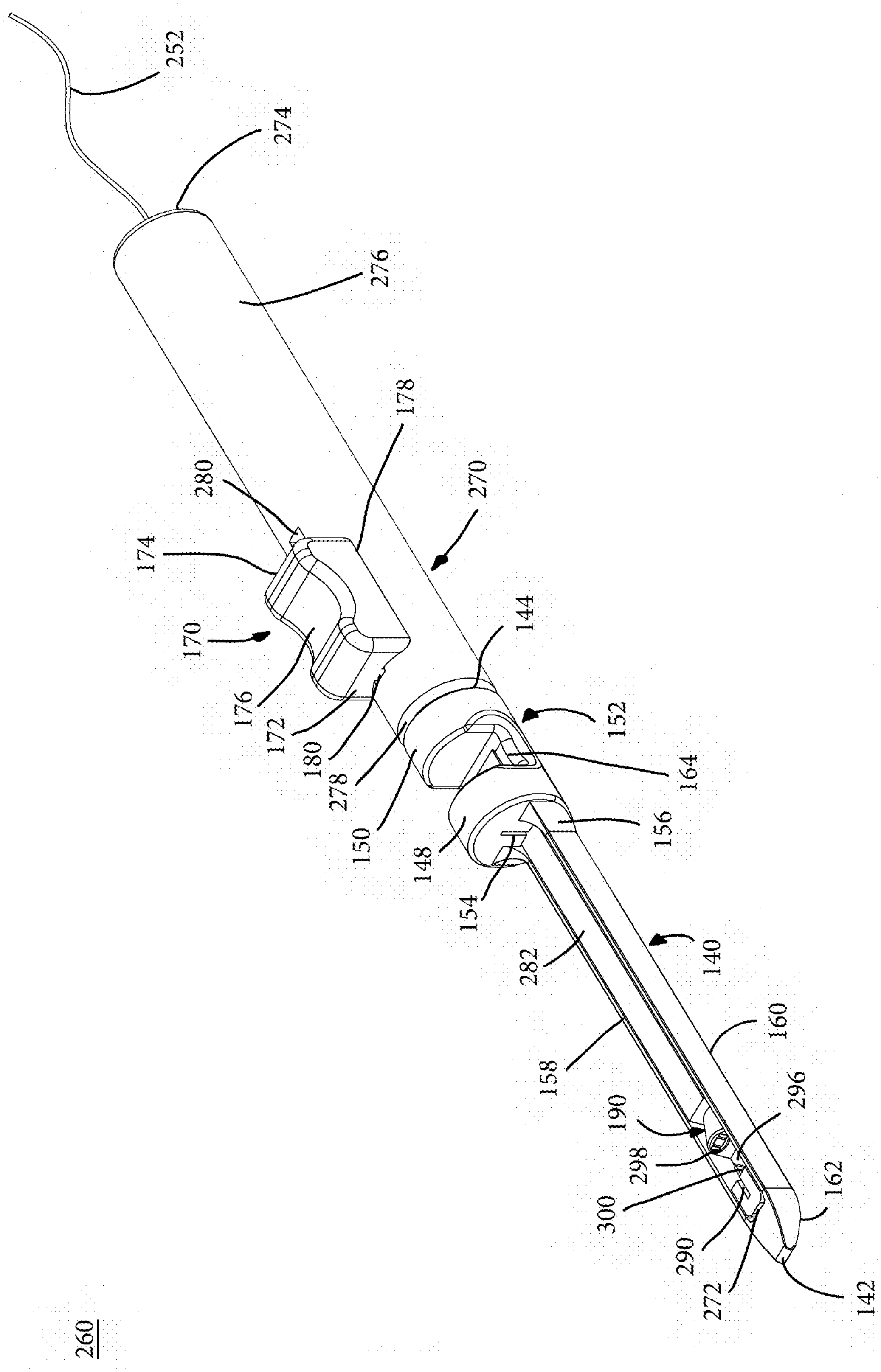
FIG. 24 is a perspective view of the release instrument of FIG. 15 in an undeployed position, in accordance with an aspect of the present disclosure.
Figure 25:
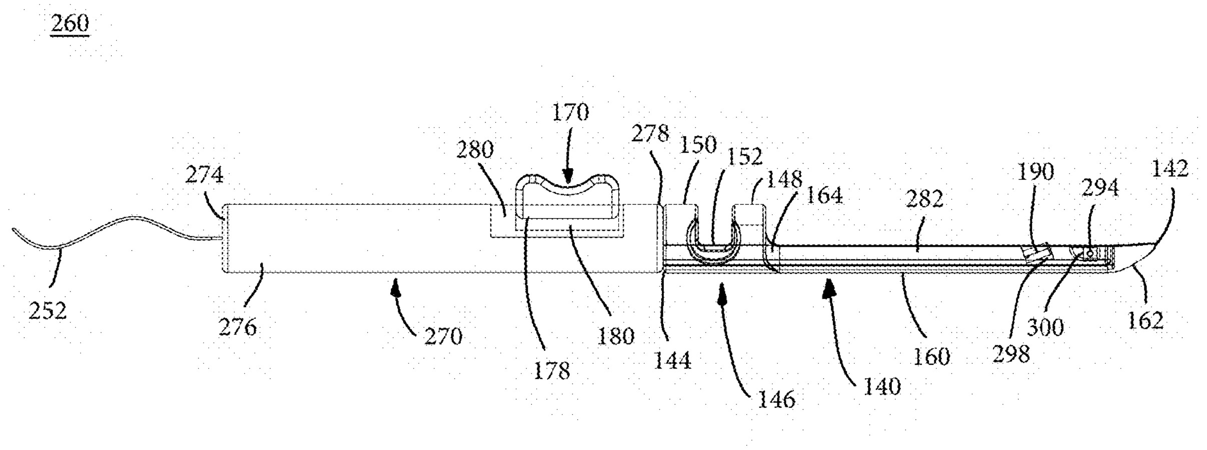
FIG. 25 is a side view of the release instrument of FIG. 24 with a transparent handpiece and transparent cannula, in accordance with an aspect of the present disclosure.

The blade housing 288 may also include a slot 290 extending into the blade housing 288 from a distal end of the blade housing 288 toward the first end 272 of the housing 270, as shown in FIGS. 19-21 and 23-25. The slot 290 may be, for example, sized and shaped to receive the blade 300 and allow the blade 300 to rotate from an undeployed position to a deployed position, as discussed in greater detail below. The blade housing 288 may also include an opening 292 extending across at least a portion of the blade housing 288 perpendicular to the longitudinal axis of the handpiece 270. The opening 292 may extend, for example, across the slot 290 to allow for insertion of a pin 294 through the opening 292 and the blade 300 to rotatably secure the blade 300 to the arm member 282, as shown in FIGS. 21 and 25. The arm member 282 may also include a recess or cutout 296 positioned adjacent to the blade housing 288, as shown in FIGS. 19 and 21-25. The recess 296 may extend from a top surface of the arm member 282 toward the bottom surface. The recess 296 may be, for example, sized and shaped to receive at least a portion of the blade 300 when positioned in an undeployed position. In addition, as shown in FIGS. 21-25, the arm member 282 may include a camera mounting surface 298 positioned adjacent to the recess 296 offset from the first end 272 of the handpiece 270. The mounting surface 298 may be, for example, angled from a first end of the mounting surface 298 to a second end of the mounting surface 298. The first end of the mounting surface 298 may be, for example, positioned below the top surface of the arm member 282. In addition, the mounting surface 298 may be, for example, curved or arced between a first or medial side and a second or lateral side of the arm member 298. The mounting surface 298 being inset or recessed allows for the coupled camera unit 190 to be positioned below the top surface of the arm member 282.

The first end 272 of the handpiece 270 may be inserted into the second end 144 of the cannula 140. The arm member 282 of the handpiece 270 may be slidingly received within the channel 158 of the cannula 140. The recessed region 152 of the cannula 140 may have, for example, a width that allows for the blade 300 to be fully positioned within the recessed region 152 when in the extended or deployed position. In an alternative embodiment, the recessed region 152 may be used, for example, to join the cannula 140 to the handpiece 120 and/or as a grip or pinch feature to facilitate separation of the cannula 140 from the handpiece 120. In addition, the cavity 154 may be, for example, an elongated rectangular shaped cavity 154. The cavity 154 may be, for example, sized and shaped to allow for the extended or deployed blade 300 to pass through during the release procedure.

Referring now to FIGS. 14-16 and 19-25, the blade 300 may include a first end 302 and a second end 304. The blade 300 may also include a cutting edge 306 extending from the first end 302 to the second end 304. The cutting edge 306 may be, for example, curved or arced from a first side across a top of the blade 300 to a second side and at least partially down the second side from the top toward the bottom of the blade 300. The first side of the blade 300 may have, for example, a straight edge that is dull, such that only the second side of the blade 300 is sharp for cutting. The blade 300 may be, for example, shaped similar to the blade of a sheepsfoot knife. The blade 300 may also include an opening 308 extending through the blade 300 in a direction perpendicular to a longitudinal axis and cutting edge 306 of the blade 300. The opening 308 may be, for example, sized and shaped to receive the pin 294 for coupling the blade 300 to the arm member 282.

Figure 26:
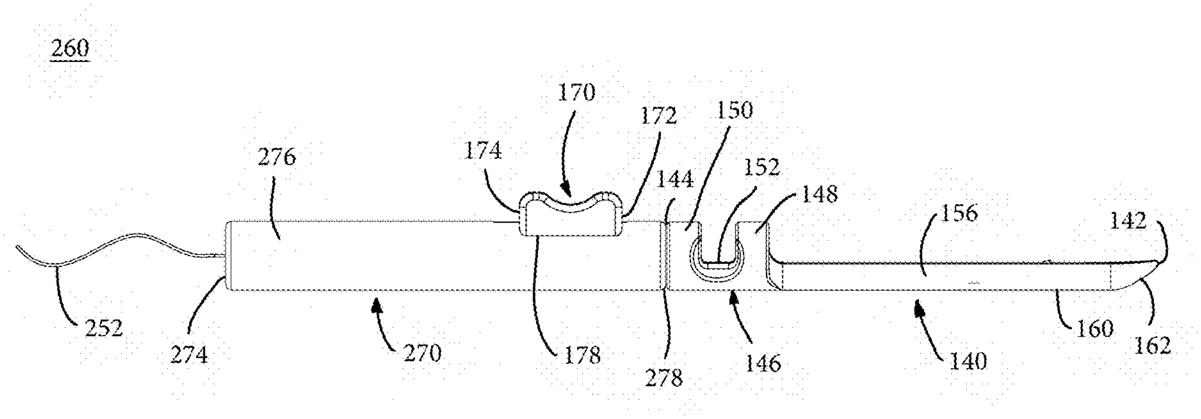
FIG. 26 is a side view of the release instrument of FIG. 15 in an undeployed position, in accordance with an aspect of the present disclosure.
Figure 27:
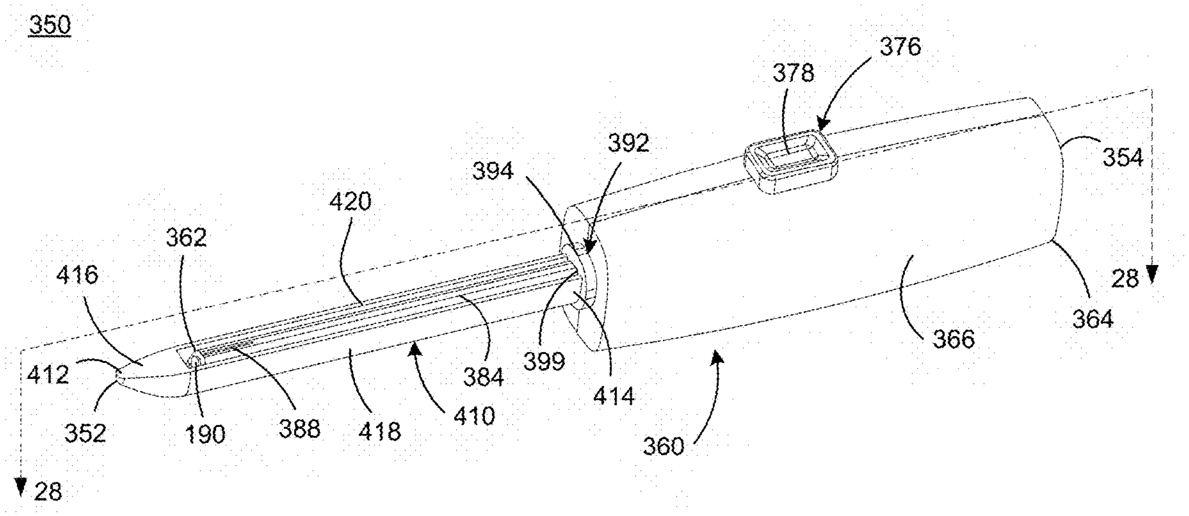
FIG. 27 is a perspective view of another embodiment of a release instrument for a videoscopic arthroscopic system, in accordance with an aspect of the present disclosure.

The blade 300 is inserted into the slot 290 and rotatably or pivotably coupled to the arm member 282 by the pin 294. The blade 300 may be inserted to position the cutting edge 306, such that, it may rotate or pivot between a position extending toward the distal end 284 of the arm member 282 and a position extending toward a bottom surface of the slot 290. The blade 300 may be, for example, coupled to the translating member 170. The blade 300 may be directly or indirectly coupled to the translating member 170 by a wire coupled to the blade 300 on one end and the translating member 170 on the other end. For example, as the translating member 170 is moved from a first position, as shown in FIGS. 24-26, to a second position, as shown in FIGS. 14-21, the blade 300 moves from a first insertion position or an undeployed position, as shown in FIGS. 24-26, to a second position or deployed position, as shown in FIGS. 14-21. The first insertion position includes the blade 300 positioned such that a first portion of the cutting edge 306 is positioned below a top surface of the arm member 282 and a second portion of the cutting edge 306 of the blade 300 is positioned pointing in the direction of the second end 274 of the handpiece 270 and a bottom surface 160 of the cannula 140. The blade 300 can then be moved to the second deployed position which rotates or pivots the blade 300 to a position where at least a portion of the blade 300 extends above a top surface of the arm member 282 and the first portion of the cutting edge 306 is positioned pointing in the direction away from the bottom surface 160 of the cannula 140 and the second portion of the cutting edge 306 is positioned pointing in the direction of the second end 274 of the handpiece 270. To move the blade 300, the translating member 170 may be, for example, slid from a position closer to the second end 274 of the handpiece 270 to a position closer to the first end 272 of the handpiece 270. As the translating member 170 is slid toward the first end 272 of the handpiece 270, the blade 300 rotates or pivots to extend at least a portion of the cutting edge 306 of the blade 300 above the top surface of the arm member 282. In addition, as the translating member 170 is slid toward the second end 274 of the handpiece 270, the blade 300 rotates or pivots back to a retracted position with the cutting edge 306 positioned completely below the top surface of the arm member 282.

As shown in FIGS. 15, 17, 19-21, 24 and 25, the camera unit 190 may be coupled to the mounting surface 298 of the arm member 282. The exterior surface of the camera unit 190 may be, for example, sized and shaped to match a top of the mounting surface 298. The coupling portion 200 of the camera unit 190 may be used to secure the camera unit 190 to the mounting surface 298. The first end of the camera unit 190 may be positioned, for example, flush with or protruding from the top surface of the handpiece 270. The coupling portion 200 may allow for the camera unit 190 to be fixed or to allow for movement of the camera unit 190, for example, rotation or pivoting of the camera unit 190 relative to the mounting surface 298 of the arm member 282. Alternative coupling portions 200 are also contemplated to allow for rotation or pivoting of the camera unit 190 in all directions about the point of attachment of the coupling portion 200 to the arm member 282. The camera sensor 194 and light members 196, 198 of the camera unit 190 may be, for example, positioned between the blade 300 and the distal end 284 of the arm member 282.

The release instrument 260 may be assembled by inserting the blade 300 into the slot 290 in an undeployed position and rotatably coupling the blade 300 to the arm member 282. The camera unit 190 may also be secured to the arm member 282. In addition, the translating member 170 may be inserted into the first slot 280 of the body 276 and the protrusion 180 directly or indirectly coupled to the blade 300 to allow for rotation of the blade 300 as the translating member 170 is moved or translated. Then, the first end 272 of the arm member 282 of the handpiece 270 may be inserted into the second end 144 of the cannula 140. The arm member 282 may then be slid along the channel 158 of the cannula 140.

Referring now to FIGS. 27-30, another release instrument 350 for a videoscopic arthroscopic system, such as system 100, is shown. The release instrument 350 includes a handpiece or housing 360 and a cannula 410 that slidingly receives a portion of the handpiece 360. The cannula 410 is positioned at a first end 352 of the release instrument 350 and the handpiece 360 is positioned at the second end 354 of the release instrument 350 and extends toward the first end 352.

Figure 28:
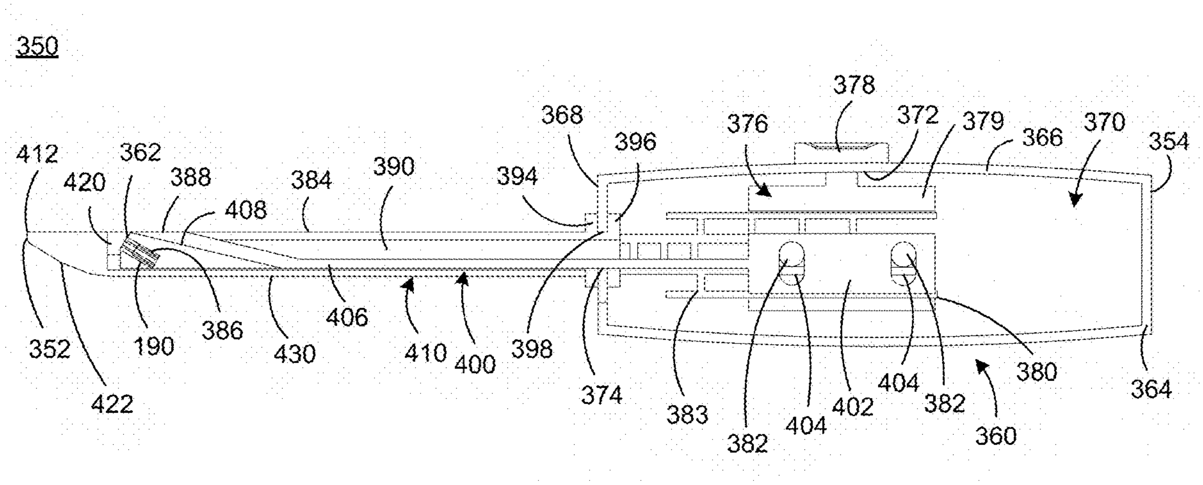
FIG. 28 is a cross-sectional side view of the release instrument of FIG. 27 taken along line 28-28 in FIG. 27 in a first undeployed position, in accordance with an aspect of the present disclosure.
Figure 29:
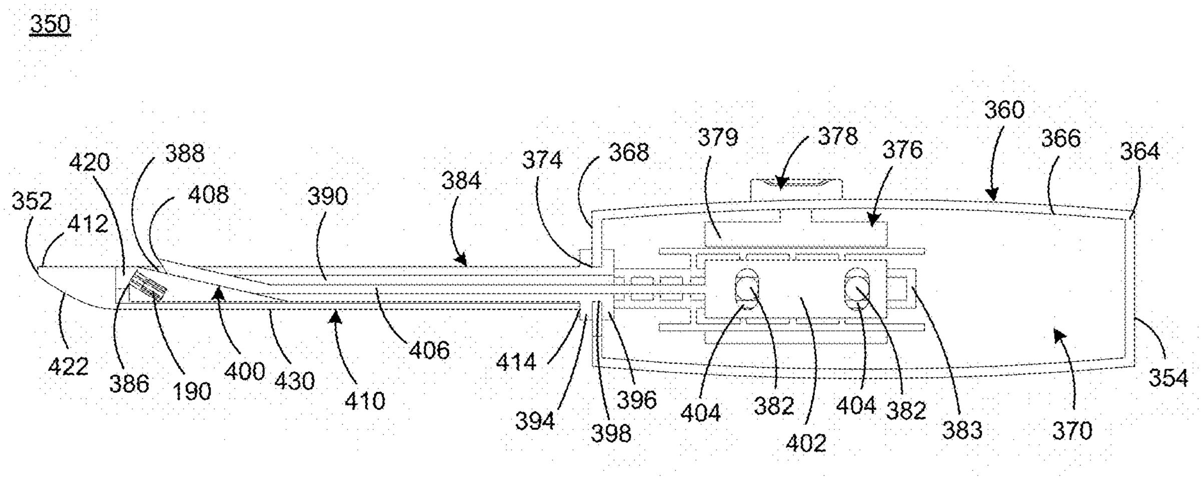
FIG. 29 is a cross-sectional side view of the release instrument of FIG. 27 taken along line 28-28 in FIG. 27 in a second partially deployed position, in accordance with an aspect of the present disclosure.
Figure 30:
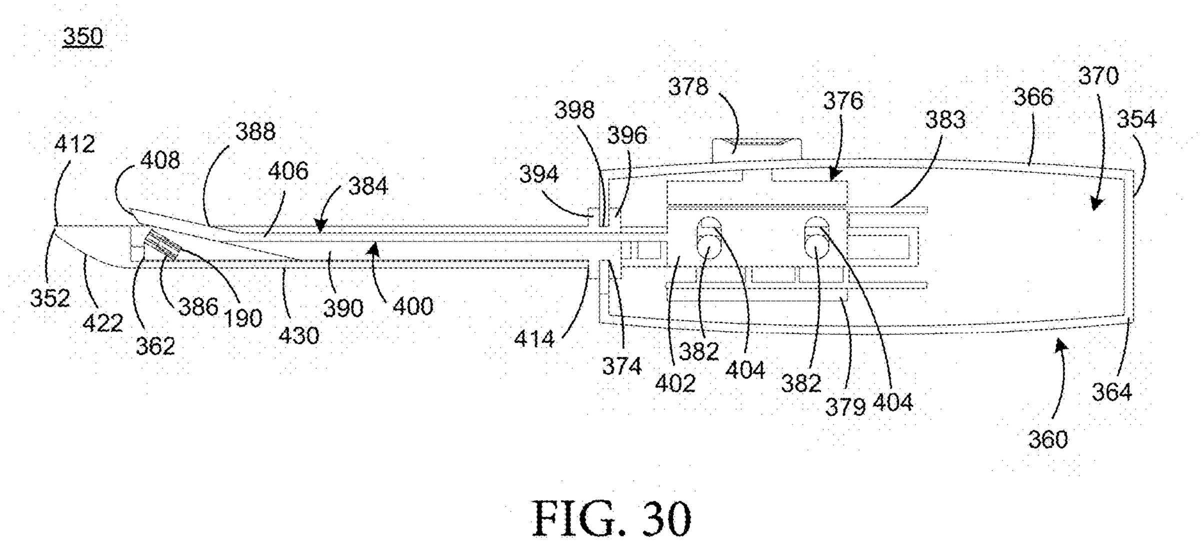
FIG. 30 is a cross-sectional side view of the release instrument of FIG. 27 taken along line 28-28 in FIG. 27 in a third fully deployed position, in accordance with an aspect of the present disclosure.
Figure 31:
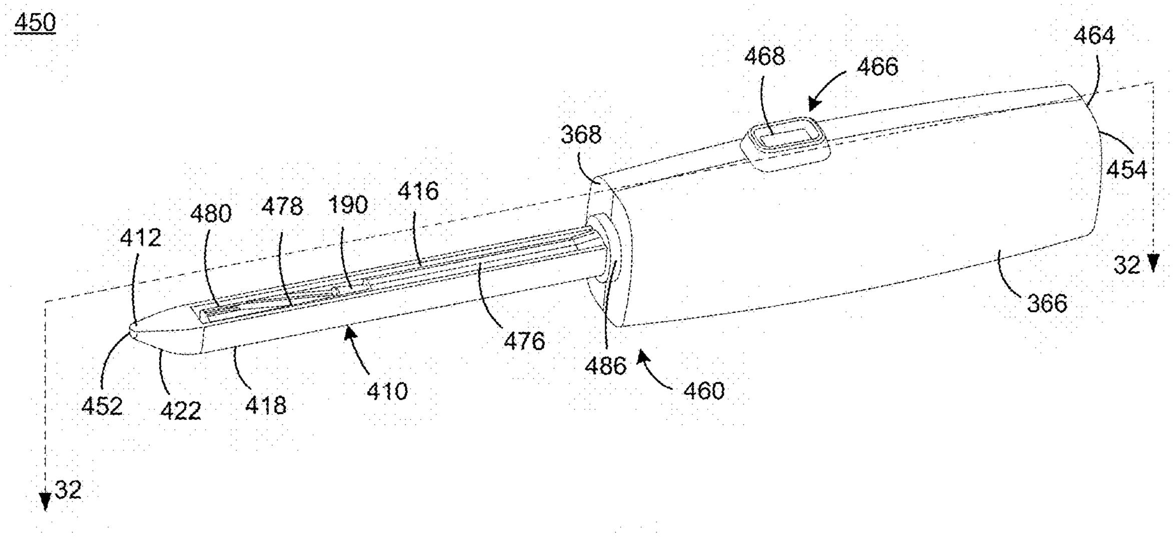
FIG. 31 is a perspective view of another embodiment of a release instrument for a retrograde videoscopic arthroscopic system, in accordance with an aspect of the present disclosure.

As shown in FIGS. 28-30, the handpiece 360 includes a first end 362 and a second end 364. The handpiece 360 includes a body 366 extending from the second end 364 toward the first end 362 and a blade holder 384 coupled to the body 366 at a proximal end 368 and extending toward the first end 352 of the release instrument 350. The body 366 may be, for example, a singular integral or monolithic piece (i.e., of one-piece construction), or may be formed from a plurality of components that are coupled (e.g., rigidly coupled) together to form the body 366 of the handpiece 360. The body 366 also includes an interior cavity 370 extending inside the body 366 from the proximal end 368 to the second end 364. The body 366 also includes a first slot 372 extending into the interior cavity 370 from an exterior surface on a top surface of the body 366. The body 366 further includes an opening 374 extending through the body 366 at the proximal end 368. The opening 374 receives a portion of the blade holder 384 to allow for the blade holder 384 to couple to the body 366. The handpiece 360 also includes a translating member 376 that extends from an exterior surface, through the first slot 372, and into the interior cavity 370. The translating member 376 includes a button 378 positioned on an exterior surface of the body 366 and a base 379 positioned in the interior cavity 370. The button 378 is coupled to the base 379 by a portion of the button 378 that is sized and shaped to extend through the first slot 372. The base 379 may also include a recessed region 380 inset into the base 379 and at least one pin 382 coupled to and extending away from the recessed region 380. As shown, the at least one pin 382 may be, for example, two pins 382 positioned spaced apart and adjacent to each other on the recessed region 380. In addition, the translating member 376 may be coupled to a spring unit 383 within the interior cavity 370 of the body 360 to assist with both deployment and undeployment of the blade member 400.

With continued reference to FIGS. 27-30, the blade holder 384 includes a first opening or camera opening 386 positioned at and extending into the first end 362 of the handpiece 360. The first opening 386 may receive, for example, a camera unit 190 as described in greater detail above and which will not be described again here for brevity's sake. The blade holder 384 also includes a second slot 388 extending from a top surface of and into the blade holder 384. In addition, the blade holder 384 includes a channel 390 extending from the second slot 388 through the blade holder 384 and out the second end of the blade holder 384. The blade holder 384 also includes a coupling portion 392 at the second end of the blade holder 384. The channel 390 also extends through the coupling portion 392, as shown in FIGS. 28-30. The coupling portion 392 may include a first portion 394, a second portion 396, and a recessed region 398 positioned between the first portion 394 and the second portion 396. The second portion 396 may be positioned at the second end of the blade holder 384 and the first portion 394 may be positioned spaced from the second portion 396 toward the first end 362 of the handpiece 360. The recessed region 398 may have, for example, the same exterior shape as the majority of the blade holder 384. For example, the recessed region 398 may have a height and a width that are the same size as a height and a width of the majority of the length of the blade holder 384. In addition, the first portion 394 and the second portion 396 may be, for example, larger than the recessed region 398 and the rest of the length of the blade holder 384. Further, the first portion 394 and the second portion 396 may each have a height and a width which may be larger than the height and width of the recessed region 398. When assembled the second portion 396 of the coupling portion 392 is positioned within the interior cavity 370 of the body 366, the recessed region 398 engages the opening 374 of the body 366, and the first portion 394 is positioned on the exterior surface of the body 366 surrounding the opening 374. The coupling portion 392 may also include a through hole 399 extending through the first portion 394, the recessed region 398, and the second portion 396. The through hole 399 may allow for the blade member 400 and at least one wire or cable to extend through the blade holder 384 and into the interior cavity 370 of the body 366.

The handpiece 360 also includes a blade member 400, as shown in FIGS. 28-30. The blade member 400 includes an engagement portion or engagement plate 402, a shaft 406 with a first end coupled to and extending out from the engagement portion 402, and a cutting edge 408 positioned at a second end of the shaft 406. The engagement portion 402 is sized and shaped to fit within the recessed region 380 of the translating member 376. The engagement portion 402 may have, for example, a generally rectangular shape. The engagement portion 402 may also include at least one engagement slot 404 extending through the engagement portion 402 from a first side to a second side. The at least one engagement slot 404 may be, for example, two slots 404 positioned adjacent to and spaced apart from each other. The slots 404 may be, for example, spaced apart the same distance as the two pins 382 of the translating member 376, as the pins 382 are configured to engage the slots 404. The coupling of the pins 382 into the slots 404 allows for the motion of the button 378 to be translated to motion of the blade member 400, specifically, motion of the cutting edge 408. The shaft 406 may be, for example, sized and shaped to have a height and width smaller than the height and width of the channel 390. In addition to the blade member 400 being coupled to the translating member 376, the shaft 406 and cutting edge 408 of the blade member 400 may be inserted into and extend through the channel 390 of the blade holder 384. Specifically, the shaft 406 may extend through the channel 390 from the second end of the blade holder 384 to the second slot 388. The shaft 406 may be, for example, angled or curved at the first end to allow for deployment of the cutting edge 408 from the second slot 388 as the translating member 376 is moved, as discussed in greater detail below. Likewise, the end of the channel 390 near the first end 362 of the handpiece 360 may be, for example, angled or curved from a bottom surface of the channel 390 to the second slot 388 to guide the cutting edge 408 out of the blade holder 384 through the second slot 388 as the blade member 400 is translated.

The cannula 410 may include a first end 412, a second end 414 opposite a first end 412, a top surface 416, and a bottom surface 418 generally opposite a top surface 416. The top surface 416 of the cannula 410 may be, for example, flat or planar from the first end 412 to the second end 414. The bottom surface 418 may be, for example, at least partially curved, such that the cannula 410 has a "U" shape along a majority of its length between the second end 414 and the leading end 422. The cannula 410 may also include a channel 420 extending into the cannula 410 from a top surface 416 toward a bottom surface 418 and from the second end 414 toward the first end 412. The channel 420 may be, for example, sized and shaped to receive at least a portion of the blade holder 384. In addition, the channel 420 allows for the blade holder 384 to translate along the length of the channel 420 between the second end 414 and a position slightly offset from the first end 412 of the cannula 410. The cannula 410 may also include a leading end 422 at the first end 412. The leading end 422 may be, for example, curved, arced, or angled to allow for insertion of the cannula 410 into a patient. At least a portion of the cannula 410 may be, for example, clear or opaque. For example, the cannula 410 may be made of a transparent plastic, such as, polycarbonate or a more rigid opaque polyarylamide. When at least a portion of the cannula 410 is clear, the camera sensor 194 may allow for visualization not only through the channel 420 of the cannula 410, but also through that clear portion of the cannula 410.

With continued reference to FIGS. 28-30, translation of the blade member 400 is shown. The blade member 400 may translate from a first, undeployed position, as shown in FIG. 28, with the cutting edge 408 of the blade member 400 positioned fully or completely below a top surface of the blade holder 384. As the button 378 is moved toward a first end 352 of the release instrument 350, the base 379 of the translating member 376 also moves toward the first end 352 thereby moving the coupled engagement portion 402 of the blade member 400 toward the first end 352 and translating the shaft 406 to position the cutting edge 408 at least partially above the top surface of the blade holder 384, as shown in FIG. 29. As the button 378 is moved completely to the end of the first slot 372, toward the proximal end 368 of the body 366, the cutting edge 408 of the blade member 400 will be fully deployed above the top surface of the blade holder 384 through the second slot 388, as shown in FIG. 30.

Referring now to FIGS. 31-34, another release instrument 450 for a retrograde videoscopic arthroscopic system, such as system 250, is shown. The release instrument 450 includes a handpiece or housing 460 and a cannula 410 that slidingly receives a portion of the handpiece 460. The cannula 410 is positioned at a first end 452 of the release instrument 450 and the handpiece 460 is positioned at the second end 454 of the release instrument 450 and extends toward the first end 452. The cannula 410 is as described in greater detail above with reference to release instrument 350 and which will not be described again here for brevity's sake.

As shown in FIGS. 31-34, the handpiece 460 includes a first end 462 and a second end 464. The handpiece 460 includes a body 366 extending from the second end 464 toward the first end 462 and a blade holder 476 coupled to the body 366 at a proximal end 368 and extending toward the first end 452 of the release instrument 450. The body 366 is as described in greater detail above with reference to handpiece 360 and which will not be described again here for brevity's sake. The opening 374 of the body 366 receives a portion of the blade holder 476 to allow for the blade holder 476 to couple to the body 366. The handpiece 460 also includes a translating member 466 that extends from an exterior surface, through the first slot 372, and into the interior cavity 370. The translating member 466 includes a button 468 positioned on an exterior surface of the body 366 and a base 470 positioned in the interior cavity 370. The button 468 is coupled to the base 470 by a portion of the button 468 that is sized and shaped to extend through the first slot 372. The base 470 may also include an engagement surface 472 positioned on the base 470 and at least one pin 474 coupled to and extending away from the engagement surface 472. As shown, the at least one pin 474 may be, for example, one pin 474. In addition, the translating member 466 may be coupled to a spring unit 475 within the interior cavity 370 of the body 360 to assist with both deployment and undeployment of the blade member 492.

Figure 32:
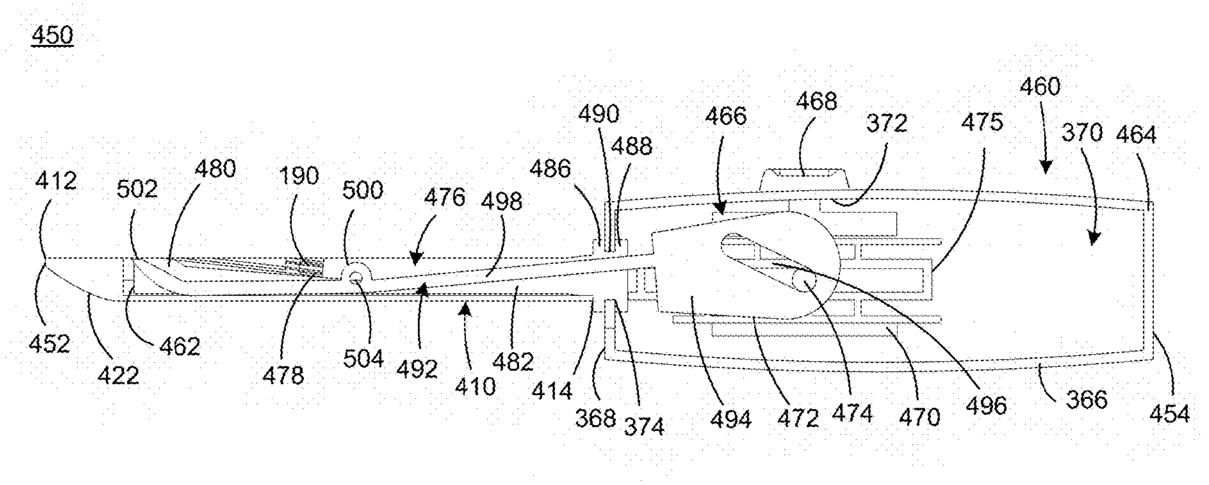
FIG. 32 is a cross-sectional side view of the release instrument of FIG. 31 taken along line 32-32 in FIG. 31 in a first undeployed position, in accordance with an aspect of the present disclosure.
Figure 33:
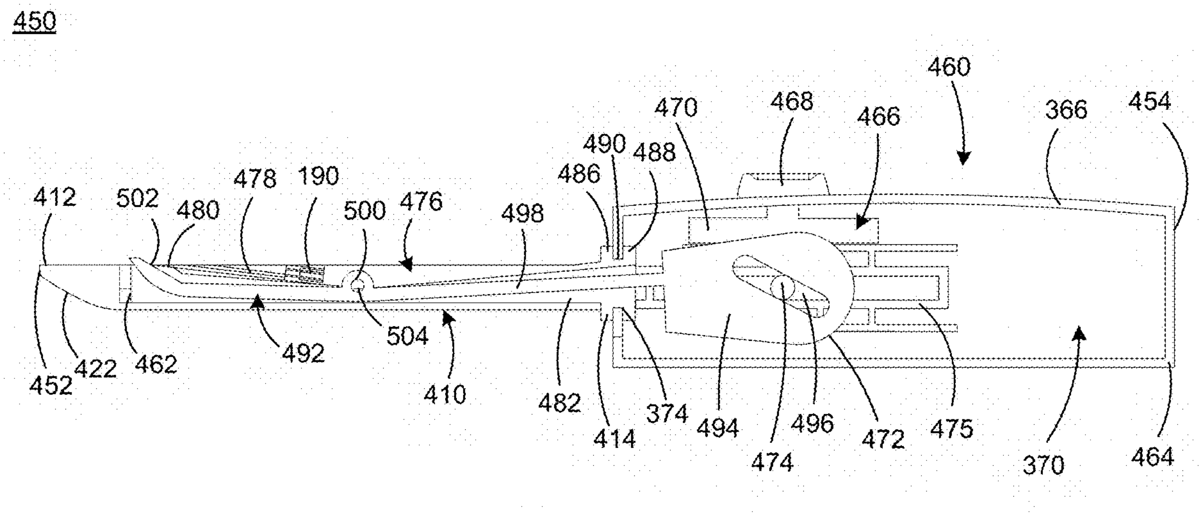
FIG. 33 is a cross-sectional side view of the release instrument of FIG. 31 taken along line 32-32 in FIG. 31 in a second partially deployed position, in accordance with an aspect of the present disclosure.
Figure 34:
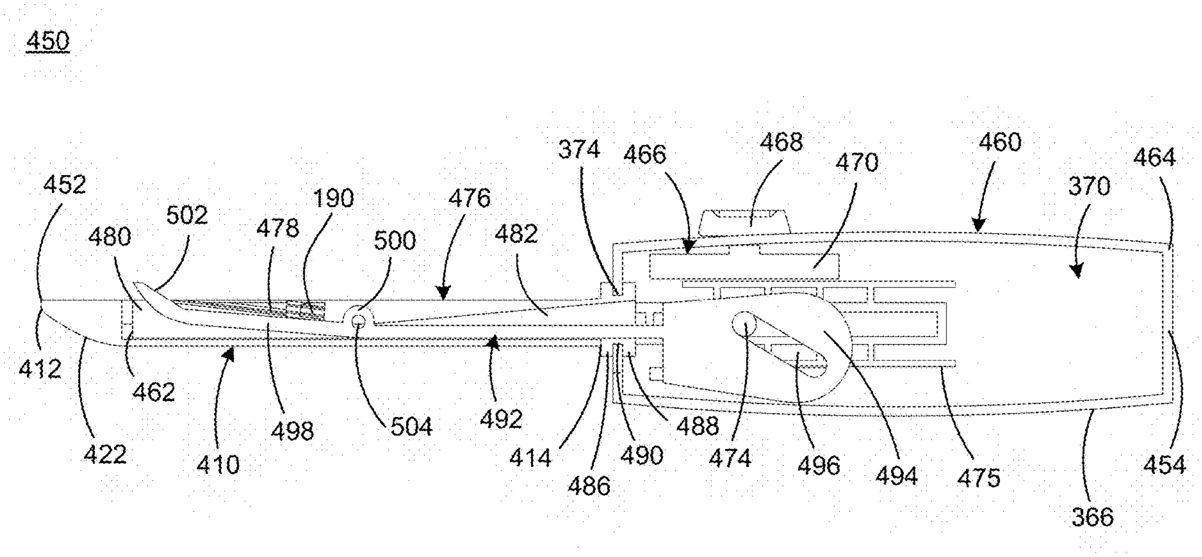
FIG. 34 is a cross-sectional side view of the release instrument of FIG. 31 taken along line 32-32 in FIG. 31 in a third fully deployed position, in accordance with an aspect of the present disclosure.
Figure 35:
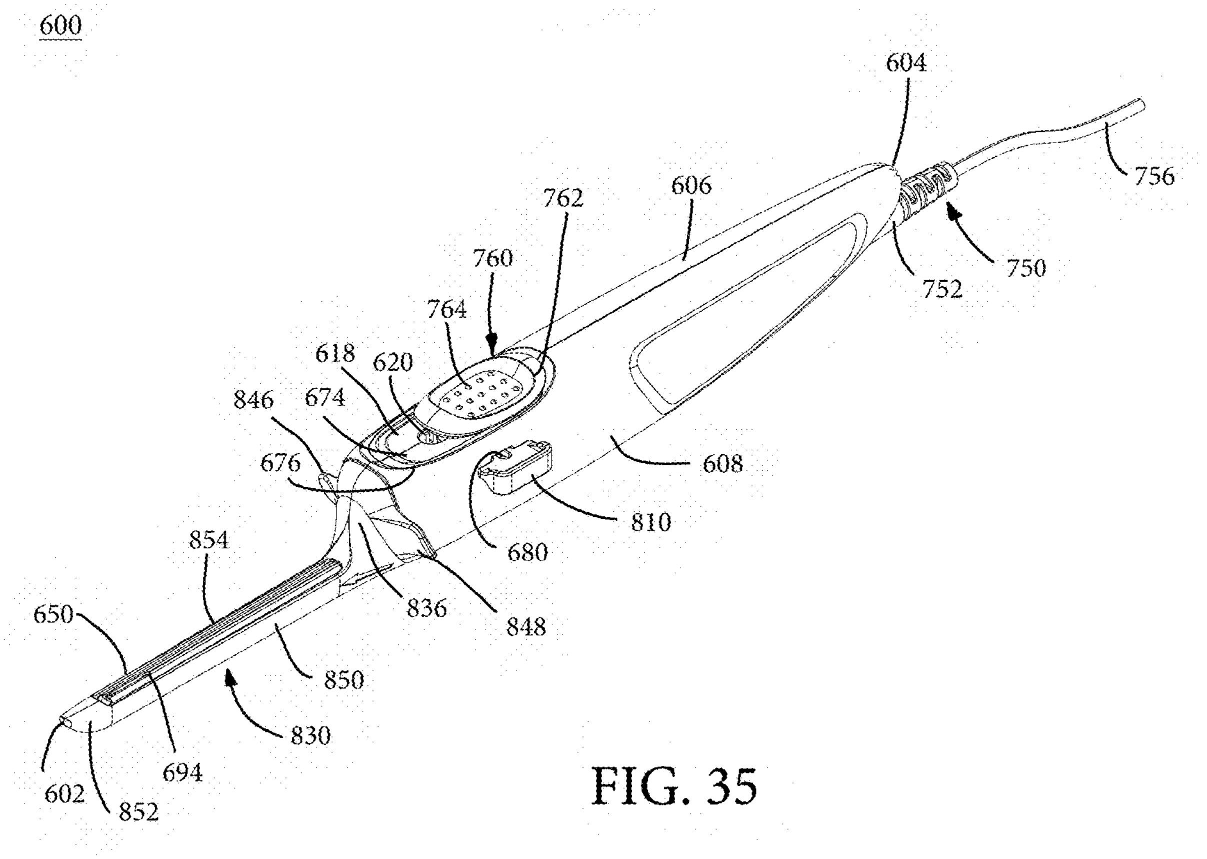
FIG. 35 is a first perspective view of another release instrument, in accordance with an aspect of the present disclosure.
Figure 36:
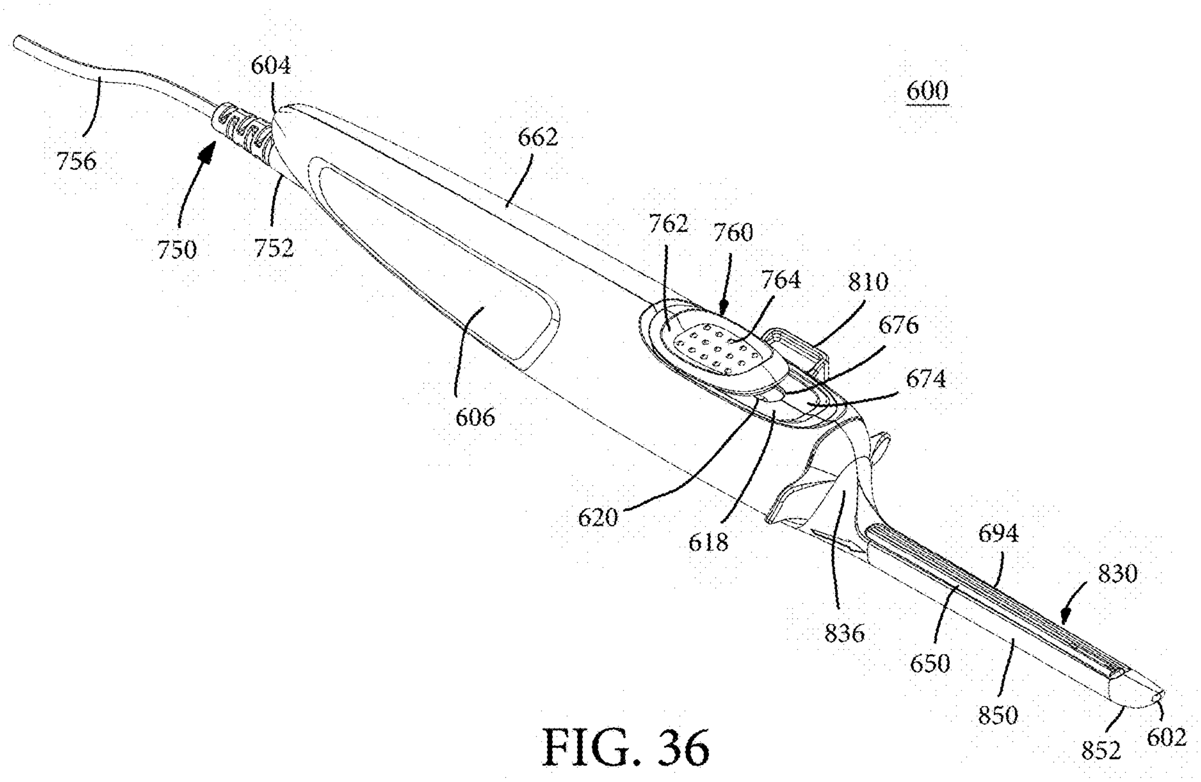
FIG. 36 is a second perspective view of the release instrument of FIG. 35, in accordance with an aspect of the present disclosure.
Figure 37:
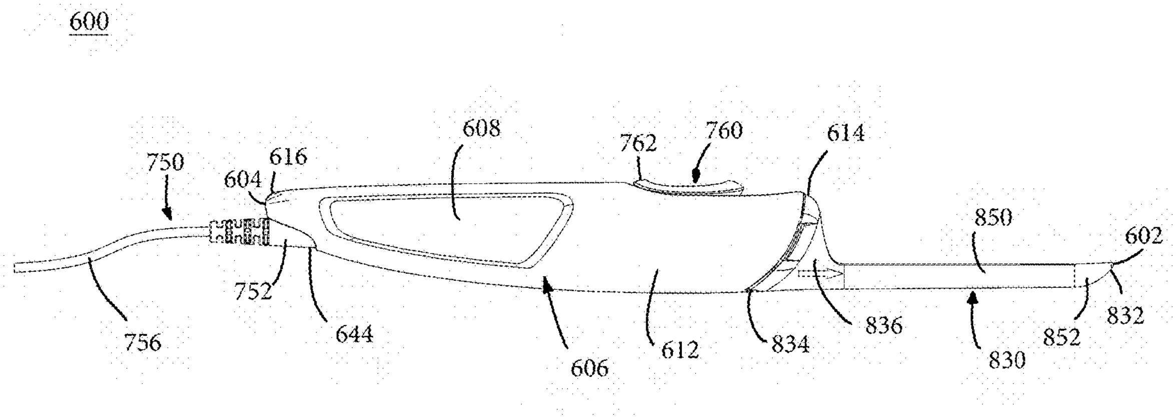
FIG. 37 is a first side view of the release instrument of FIG. 35, in accordance with an aspect of the present disclosure.
Figure 38:
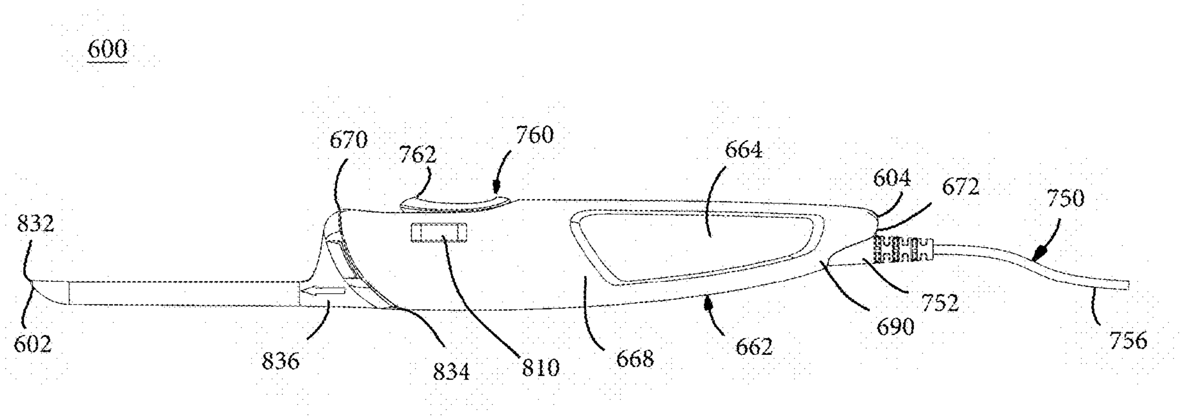
FIG. 38 is a second side view of the release instrument of FIG. 35, in accordance with an aspect of the present disclosure.
Figure 39:
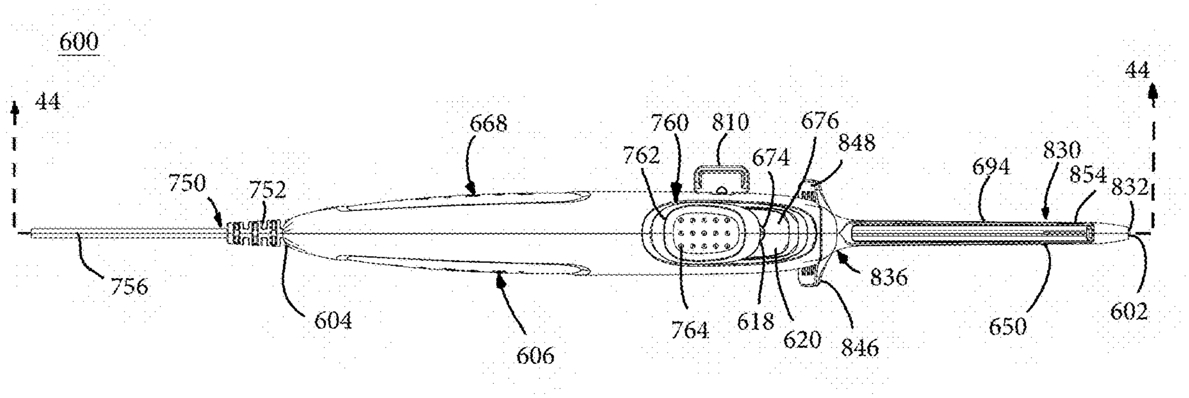
FIG. 39 is a top view of the release instrument of FIG. 35, in accordance with an aspect of the present disclosure.
Figure 40:
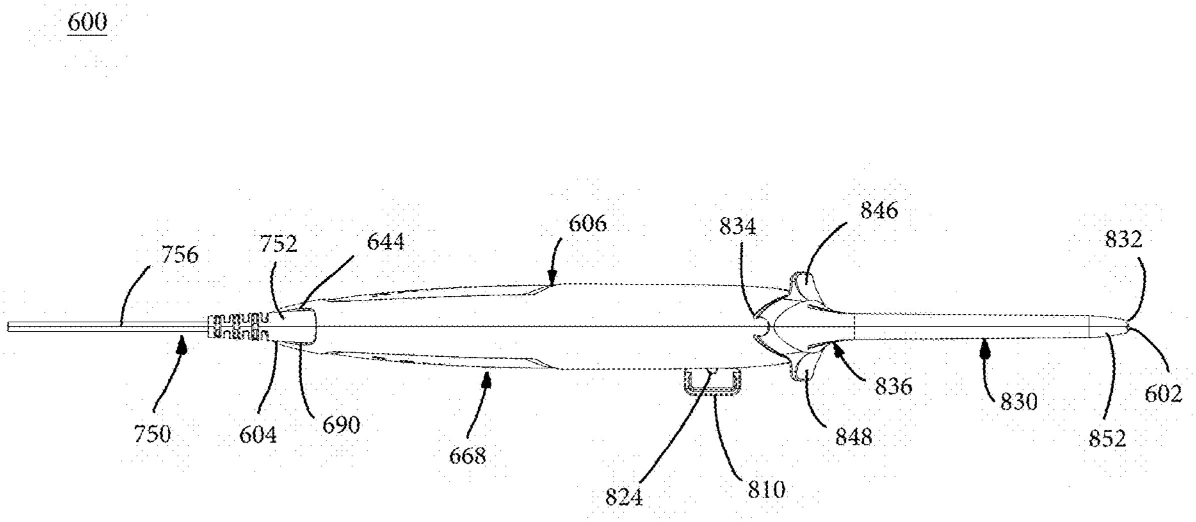
FIG. 40 is a bottom view of the release instrument of FIG. 35, in accordance with an aspect of the present disclosure.
Figure 41:
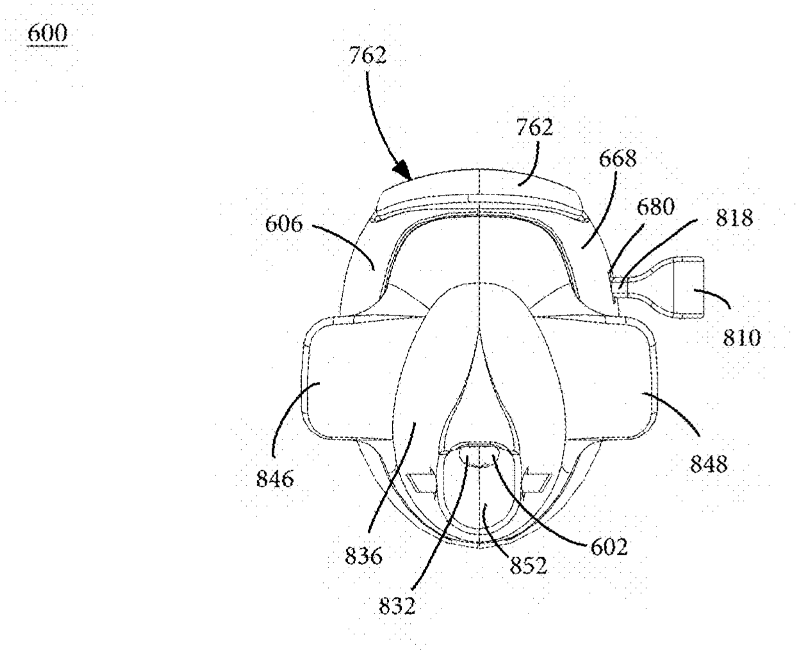
FIG. 41 is a first end view of the release instrument of FIG. 35, in accordance with an aspect of the present disclosure.
Figure 42:
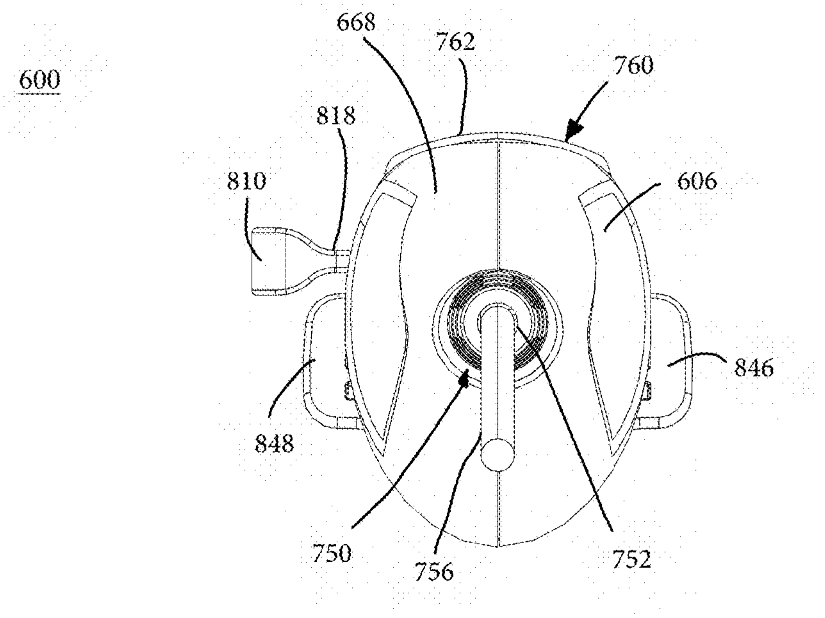
FIG. 42 is a second end view of the release instrument of FIG. 35, in accordance with an aspect of the present disclosure.
Figure 43:
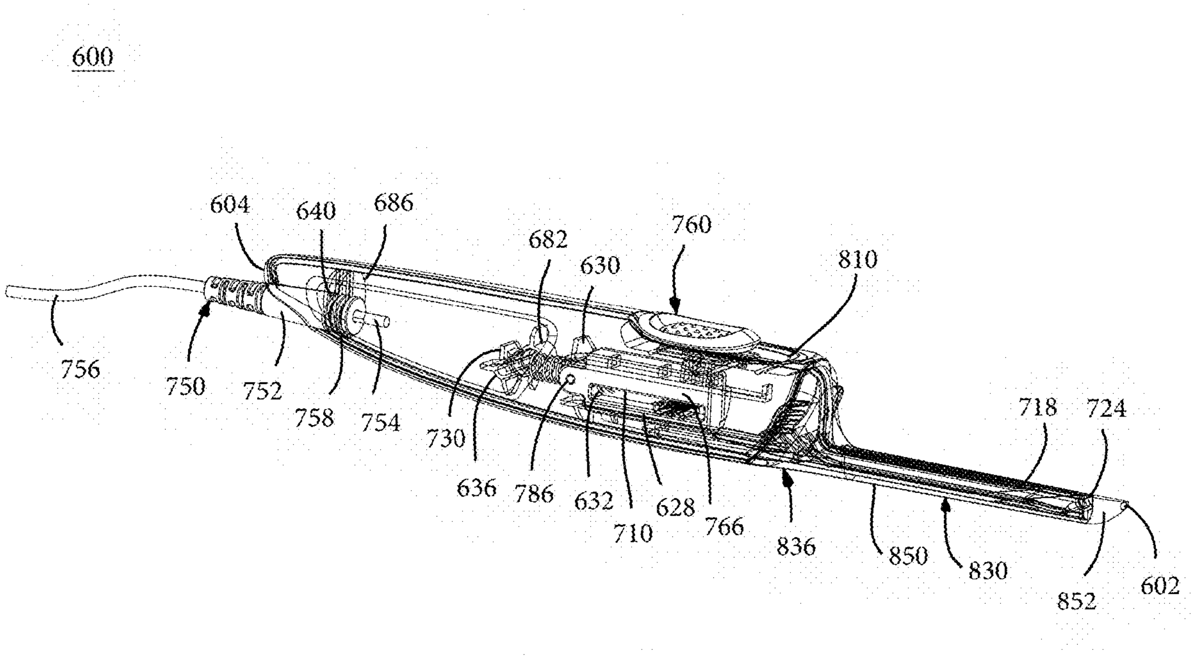
FIG. 43 is a perspective view of the release instrument of FIG. 35 with a transparent first housing and cannula, in accordance with an aspect of the present disclosure.
Figure 44:
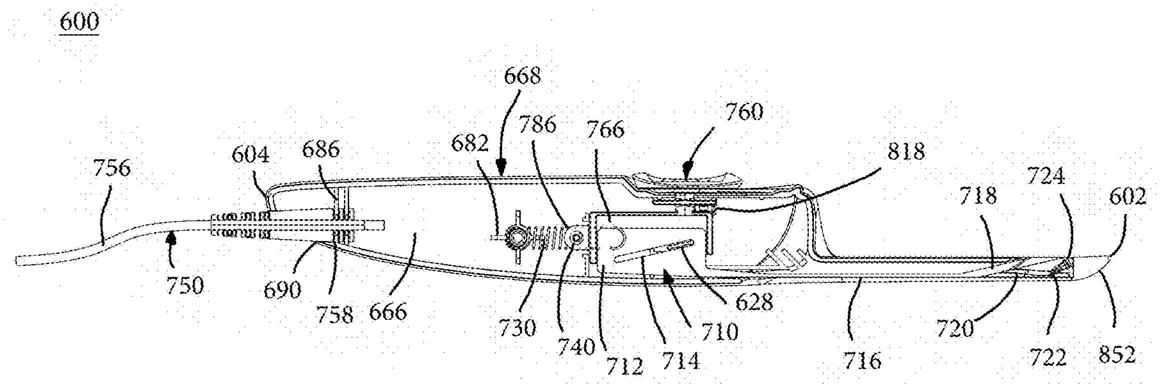
FIG. 44 is a cross-sectional side view of the release instrument of FIG. 35 taken along line 44-44 in FIG. 39, in accordance with an aspect of the present disclosure.
Figure 45:
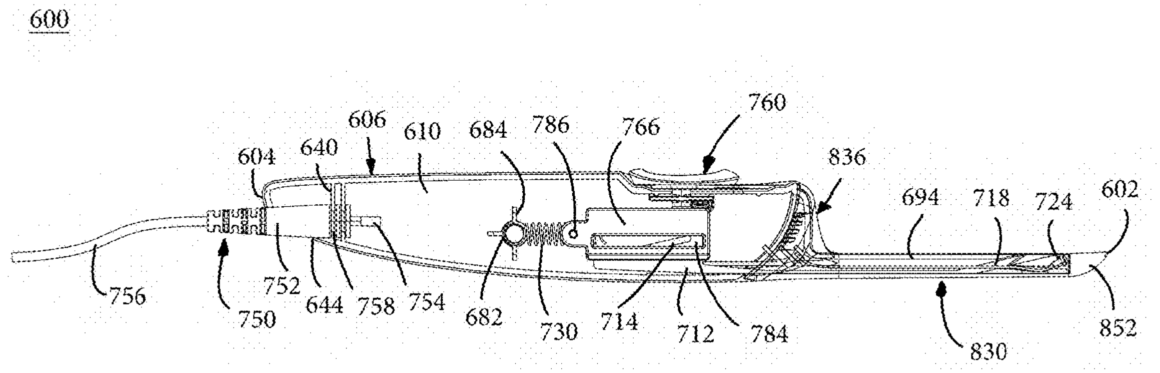
FIG. 45 is a side view of the release instrument of FIG. 35 with the first housing removed and a transparent cannula, in accordance with an aspect of the present disclosure.

The blade holder 476 includes a camera mounting surface 478 offset from a first end 462 of the handpiece 460. The mounting surface 478 may be, for example, angled as the mounting surface 478 extends from a top surface of the blade holder 476 toward a bottom surface. The mounting surface 478 may be sized and shaped to receive a camera unit 190, as described in greater detail above and which will not be described again here for brevity's sake. The blade holder 476 also includes a slot 480 extending from a top surface of and into the blade holder 476. The slot 480 may be positioned, for example, between a first end 462 of the handpiece 460 and the mounting surface 478. In addition, the blade holder 476 includes a channel 482 extending from the slot 480 through the blade holder 476 and out the second end of the blade holder 476. The blade holder 476 also includes a coupling portion 484 at the second end of the blade holder 476. The channel 482 also extends through the coupling portion 484, as shown in FIGS. 32-34. The coupling portion 484 may include a first portion 486, a second portion 488, and a recessed region 490 positioned between the first portion 486 and the second portion 488. The second portion 488 may be positioned at the second end of the blade holder 476 and the first portion 486 may be positioned spaced from the second portion 488 toward the first end 462 of the handpiece 460. The recessed region 490 may have, for example, the same exterior shape as the majority of the blade holder 476. For example, the recessed region 490 may have a height and a width that are the same size as a height and a width of the majority of the length of the blade holder 476. In addition, the first portion 486 and the second portion 488 may be, for example, larger than the recessed region 490 and the rest of the length of the blade holder 476. Further, the first portion 486 and the second portion 488 may each have a height and a width which may be larger than the height and width of the recessed region 490. When assembled the second portion 488 of the coupling portion 484 is positioned within the interior cavity 370 of the body 366, the recessed region 490 engages the opening 374 of the body 366, and the first portion 486 is positioned on the exterior surface of the body 366 surrounding the opening 374. The coupling portion 484 may also include a through hole 491 extending through the first portion 486, recessed region 490, and second portion 488. The through hole 491 may allow for the blade member 492 and at least one wire or cable to extend through the blade holder 476 and into the interior cavity 370 of the body 366.

The handpiece 360 also includes a blade member 492, as shown in FIGS. 31-34. The blade member 492 includes an engagement portion or engagement plate 494, a shaft 498 with a first end coupled to and extending out from the engagement portion 494, and a cutting edge 502 positioned at a second end of the shaft 498. The engagement portion 494 is sized and shaped to couple to the engagement surface 472 of the translating member 466. The engagement portion 494 may have, for example, a truncated oval or teardrop shape. The engagement portion 494 may include at least one engagement slot 496 extending through the engagement portion 494 from a first side to a second side. The at least one engagement slot 496 may be, for example, one slot 496 extending across the engagement portion 494 at an angle. The slot 496 may extend, for example, from a top surface closer to the proximal end 368 of the body 366 to a bottom surface closer to the second end 464 of the handpiece 460. The pin 474 may be, for example, configured to engage the slot 496. The coupling of the pin 474 into the slot 496 allows for the motion of the button 468 to be translated to motion of the blade member 492, specifically, motion of the cutting edge 502. The shaft 498 may be, for example, sized and shaped to have a height and width smaller than the height and width of the channel 482. In addition to the blade member 492 being coupled to the translating member 466, the shaft 498 and cutting edge 502 of the blade member 492 may be inserted into and extend through the channel 482 of the blade holder 476. Specifically, the shaft 498 may extend through the channel 482 from the second end of the blade holder 476 to the slot 480. The shaft 498 may be, for example, angled or curved at the first end to allow for deployment of the cutting edge 502 from the slot 480 as the translating member 466 is moved, as discussed in greater detail below. Likewise, the end of the channel 482 near the first end 462 of the handpiece 460 may be, for example, angled or curved from a bottom surface of the channel 482 to the slot 480. The shaft 498 may also include a pivot member 500 positioned between a first end and a second end. The shaft 498 may have a first portion extending from a first end to the pivot member 500 and a second portion extend from the pivot member 500 to the engagement portion 494. The first portion of the shaft 498 may be, for example, angled relative to the second portion of the shaft 498 at the pivot member 500, as shown in FIGS. 32-34. The blade member 492 may be, for example, pivotally secured to the blade holder 476 by a pivot pin 504 inserted through the pivot member 500 to allow for the cutting edge 502 to be pivotally deployed from the slot 480. The channel 420 of the cannula 410 may be, for example, sized and shaped to receive at least a portion of the blade holder 476. In addition, the channel 420 allows for the blade holder 476 to translate along the length of the channel 420 between the second end 414 and a position slightly offset from the first end 412 of the cannula 410.

With continued reference to FIGS. 31-34, movement of the blade member 492 is shown. The blade member 492 may translate from a first, undeployed position, as shown in FIG. 32, with the cutting edge 502 of the blade member 492 positioned fully or completely below a top surface of the blade holder 476. As the button 468 is moved toward a first end 452 of the release instrument 450, the base 470 of the translating member 466 also moves toward the first end 452 thereby moving the coupled engagement portion 494 of the blade member 492 down toward a bottom of the body 366 and pivoting the shaft 498 to position the cutting edge 502 at least partially above the top surface of the blade holder 476, as shown in FIG. 33. As the button 468 is moved completely to the end of the first slot 372, toward the proximal end 368 of the body 366, the blade member 492 moves down further toward a bottom of the body 366 continuing to pivot the shaft 498 to position the cutting edge 502 of the blade member 492 in a fully deployed position above the top surface of the blade holder 476 and extending through the slot 480, as shown in FIG. 34.

A surgical method for using the videoscopic arthroscopic systems 100, 250 may include obtaining a release instrument 110, 350, 260, 450. The release instruments 110, 350, 260, 450 may then be coupled to the video unit and/or a power source by a cable 116, 252. In embodiments where the release instruments 110, 350, 260, 450 are coupled to a video unit, the cable 116, 252 may transmit images of the surgical site to a video processor and/or video monitor, such as video unit 102. The video processor and monitor may be, for example, separate or combined, such as a combined processor and tablet display. After the release instruments 110, 350, 260, 450 are connected to a power source and video unit, the first end 112, 352, 262, 452 of the release instruments 110, 350, 260, 450 may be inserted into the surgical site of a patient. The blade 182, 400, 300, 492 of the release instruments 110, 350, 260, 450 will be positioned in the undeployed position during insertion. The camera unit 190 may be used to visualize the path of the release instruments 110, 350, 260, 450 as the surgeon inserts the instruments 110, 350, 260, 450 into the patient to the position where tissue release is desired. The instruments 110, 350, 260, 450 may be moved in order to position the cannula 140, 410 under the tissue to be released. Once the surgeon positions the cannula 140, 410 under the tissue to be released, the blade holder 132, 384, 282, 476 may be positioned to allow for cutting the tissue and the blade 182, 400, 300, 492 may be moved to a deployed position.

For example, for the insertion instrument 110, the sheath 132 may be moved to position the first end 122 of the handpiece adjacent to the tissue to be released. The blade 182 may then be translated out from the second slot 136 to a position where the cutting tip 188 is positioned at least partially above the top surface of the sheath 132 using the translating member 170. Then, the sheath 132 of the handpiece 120 may be moved through the channel 158 toward the first end 142 of the cannula 140 and the tissue may be cut. Once the cut is complete, the blade 182 may be retracted back to an undeployed position and the insertion instrument 110 removed from the patient.

In another example, for the insertion instrument 260, the arm member 282 may be moved to position the first end 272 of the arm member 282 at the end of the channel 158 closest to the first end 142 of the cannula 140. The insertion instrument 260, with the arm member 282 fully inserted into the cannula 140, will be inserted into the patient to position the first end 142 of the cannula 140 and the first end 272 of the handpiece past the tissue to be released. Once in position, the blade 300 may be translated out from the slot 290 to a position where at least a portion of the cutting edge 306 is positioned above the top surface of the arm member 282 using the translating member 170. Then, the arm member 282 of the handpiece 270 may be moved through the channel 158 toward the second end 144 of the cannula 140 and the tissue may be cut. Once the cut is complete, the blade 182 may be retracted back to an undeployed position and the insertion instrument 260 removed from the patient.

In yet another example, for the insertion instrument 350, the blade holder 384 may be moved to position the first end 362 of the handpiece 360 adjacent to the tissue to be released. The blade member 400 may then be translated out from the second slot 388 to a position where the cutting edge 408 is positioned at least partially above the top surface of the blade holder 384 using the translating member 376. Then, the blade holder 384 of the handpiece 360 may be moved through the channel 420 toward the first end 352 of the cannula 410 and the tissue may be cut. Once the cut is complete, the blade member 400 may be retracted back to an undeployed position and the insertion instrument 350 removed from the patient.

In a further example, for the insertion instrument 450, the blade holder 476 may be moved to position the first end 462 of the handpiece 460 at the end of the channel 420 closest to the first end 412 of the cannula 410. The insertion instrument 450, with the blade holder 476 fully inserted into the cannula 410, will be inserted into the patient to position the first end 412 of the cannula 410 and the first end 462 of the handpiece 460 past the tissue to be released. Once in position, the blade member 492 may be pivoted out from the slot 480 to a position where at least a portion of the cutting edge 502 is positioned above the top surface of the blade holder 476 using the translating member 466. Then, the blade holder 476 may be moved through the channel 420 toward the second end 414 of the cannula 410 and the tissue may be cut. Once the cut is complete, the blade member 492 may be retracted back to an undeployed position and the insertion instrument 450 removed from the patient.

Figure 14:
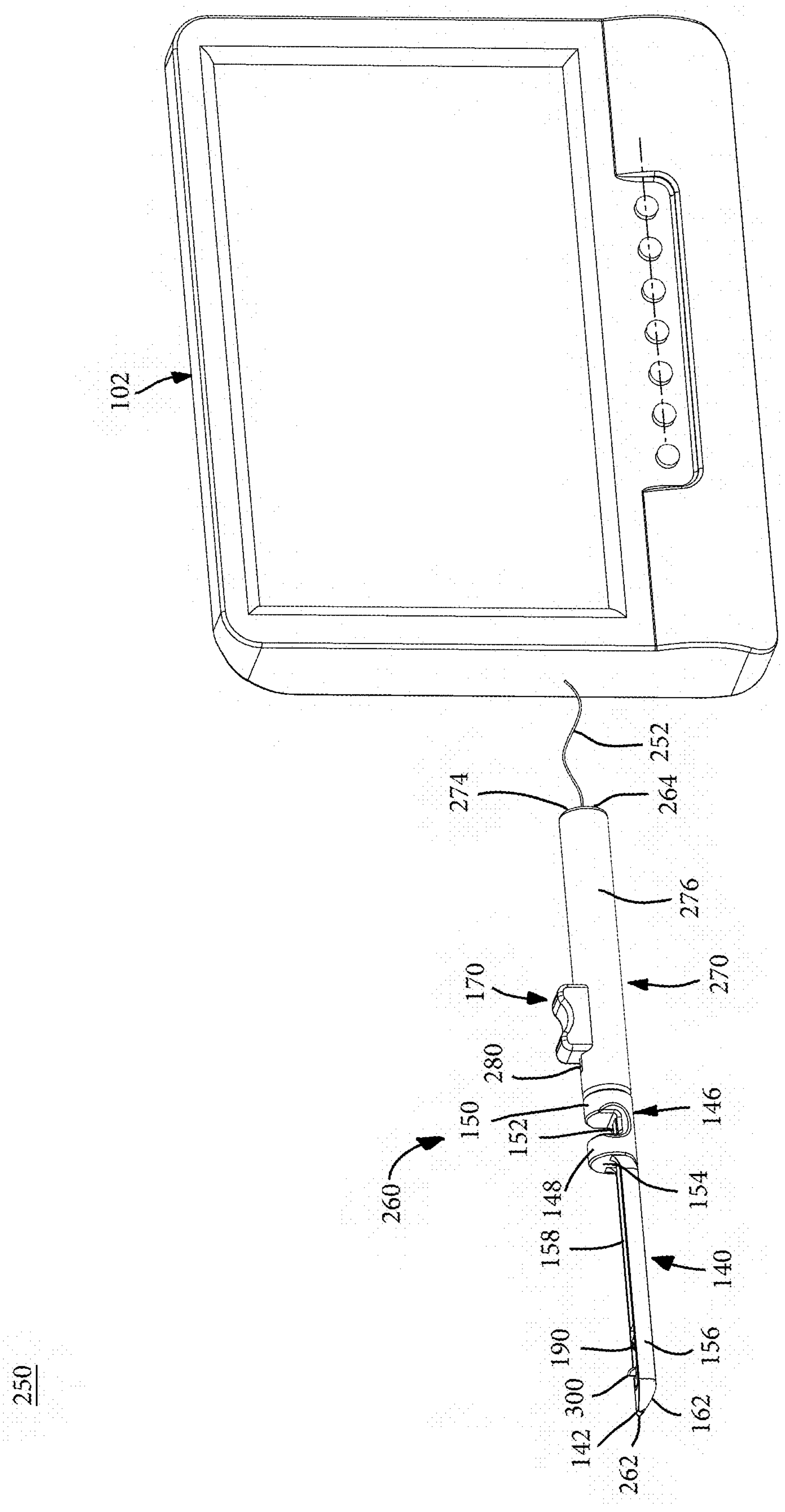
FIG. 14 is a perspective view of an embodiment of a retrograde videoscopic arthroscopic system, in accordance with an aspect of the present disclosure.
Figure 15:
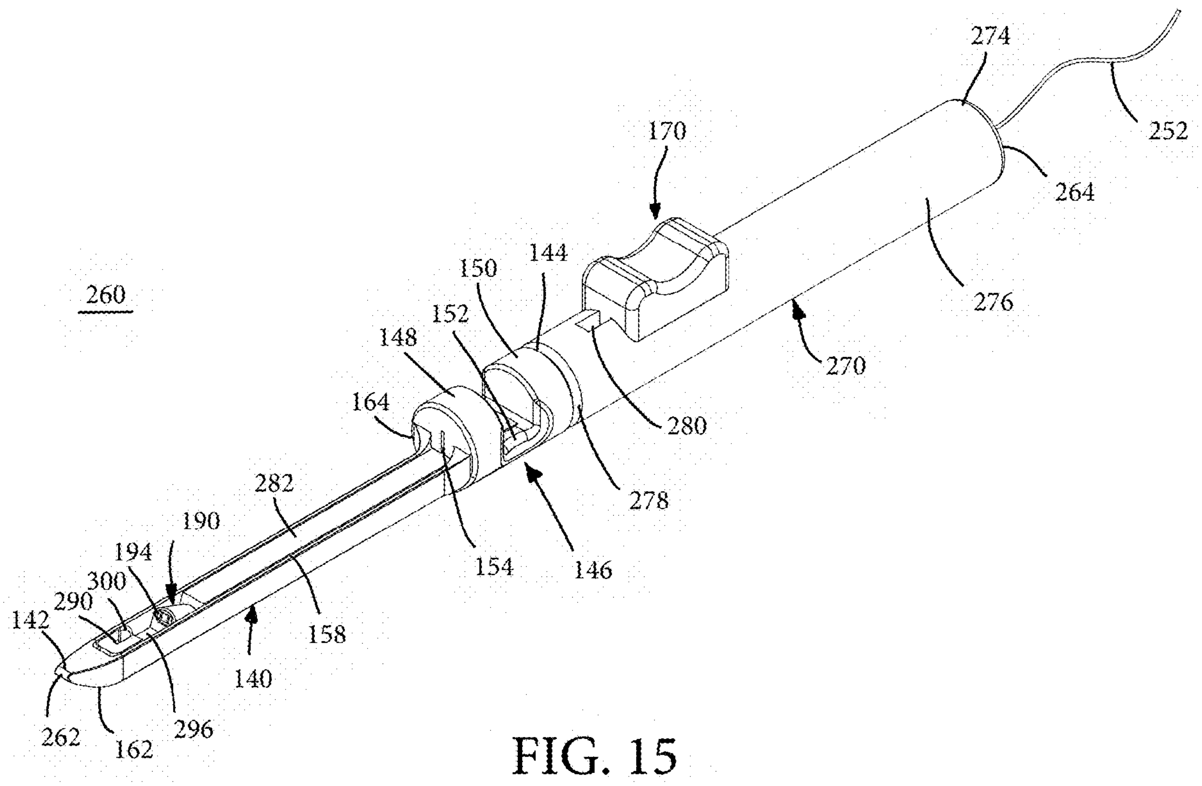
FIG. 15 is a perspective view of a release instrument of the videoscopic arthroscopic system of FIG. 14 in a deployed position, in accordance with an aspect of the present disclosure.
Figure 16:
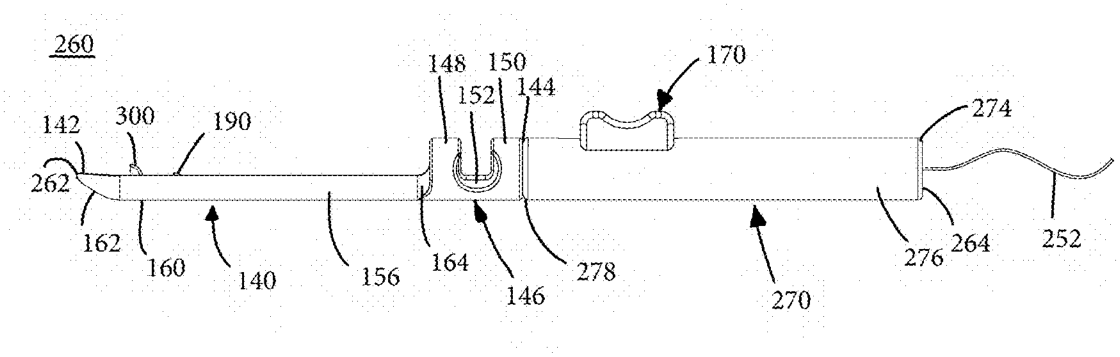
FIG. 16 is a side view of the release instrument of FIG. 15, in accordance with an aspect of the present disclosure.
Figure 17:
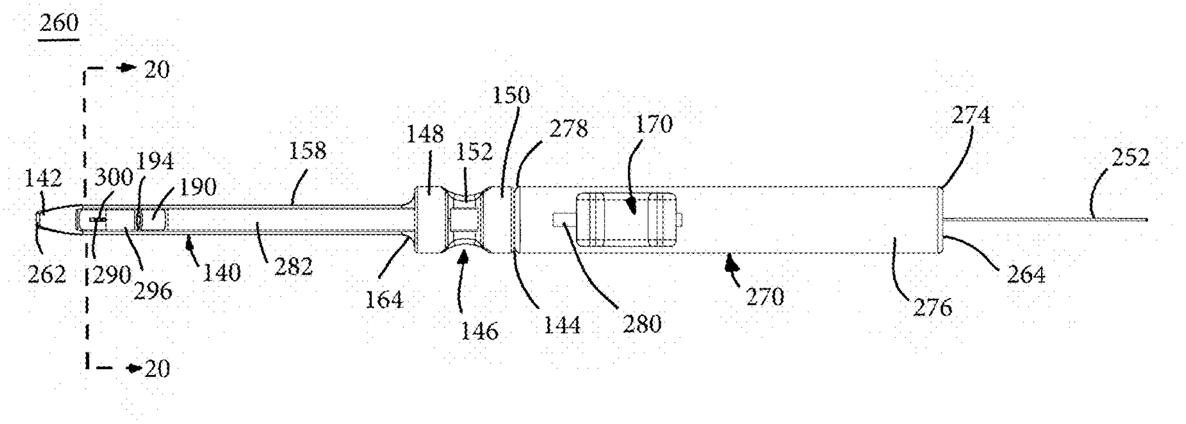
FIG. 17 is a top view of the release instrument of FIG. 15, in accordance with an aspect of the present disclosure.
Figure 18:
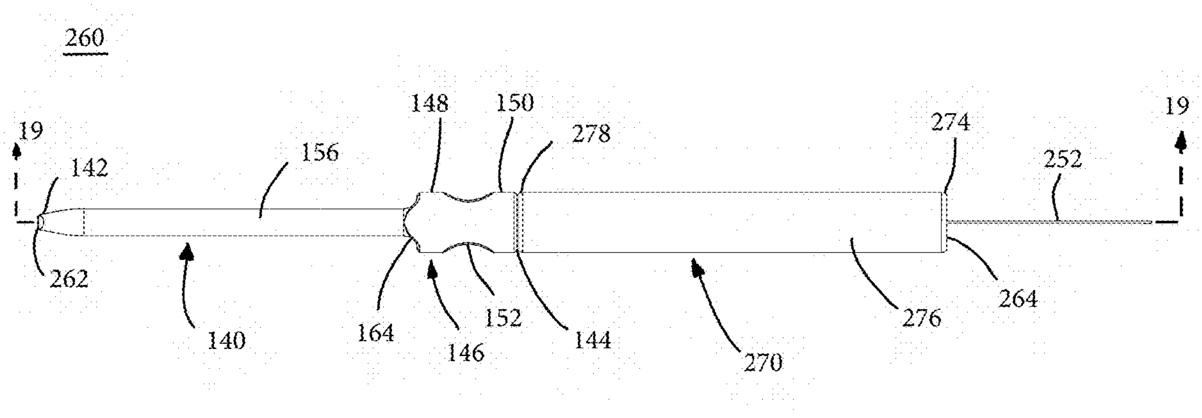
FIG. 18 is a bottom view of the release instrument of FIG. 15, in accordance with an aspect of the present disclosure.
Figure 19:
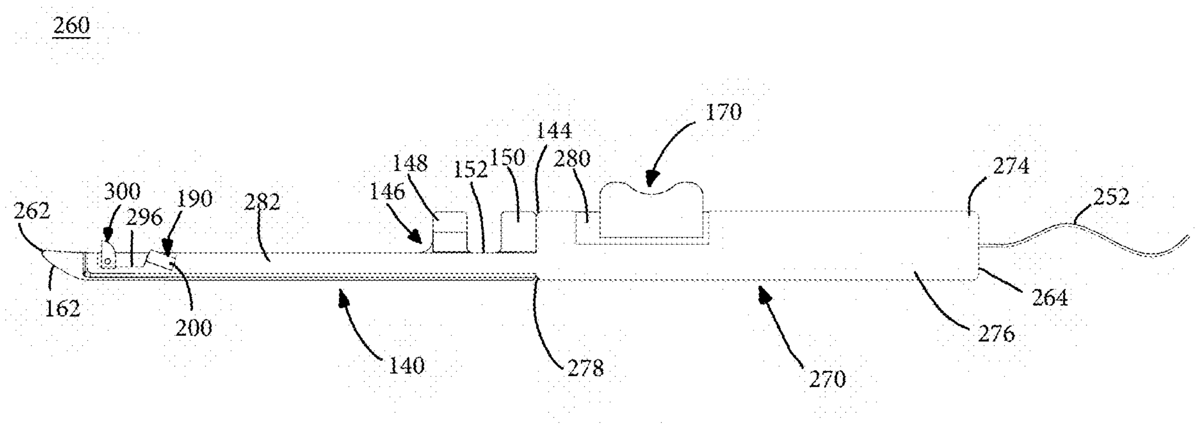
FIG. 19 is a cross-sectional side view of the release instrument of FIG. 15 taken along line 19-19 in FIG. 18, in accordance with an aspect of the present disclosure.
Figure 20:
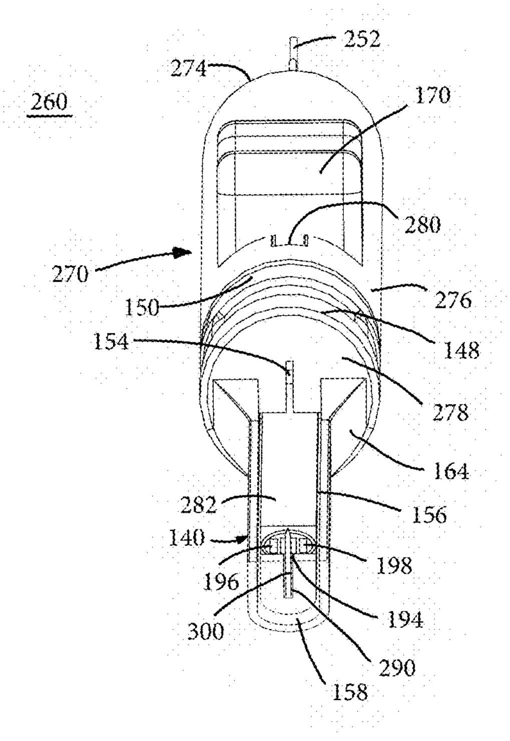
FIG. 20 is a cross-sectional front view of the release instrument of FIG. 15 taken along line 20-20 in FIG. 17, in accordance with an aspect of the present disclosure.

Referring now to FIGS. 35-53, another videoscopic arthroscopic system including a video unit 102 and a release instrument or instrument 600, is shown. The release instrument 600 may be, for example, a videoscopic, single-use, disposable, arthroscopic instrument for minimally invasive, endoscopic, tissue release surgery in a patient's joints or limbs. Specifically, the instrument 600 may be used for tissue release procedures in the wrist, foot, and elbow for cutting tendinous, ligamentous, fibrous tissue, and the like. The release instrument 600 may include a first end 602 and a second end 604 opposite the first end 602. The second end 604 of the release instrument 600 may include a cable attachment member or strain relief member 750 extending from the release instrument 600 and a cable 756 that extends from the interior of the release instrument 600 to the video unit 102. The video unit 102 may be, for example, a video display, such as a tablet, video screen, television, and the like, or a video processor that may be separate from or integral with a video display, such as shown in FIGS. 1 and 14.

With continued reference to FIGS. 35-53, the instrument 600 may include a handpiece or housing 606, 662 and a cannula 830. The handpiece 606, 662 may include a first or right housing 606 and a second or left housing 662 coupled together to form the handpiece 606, 662. A portion of the handpiece 606, 662 may be slidingly received within the cannula 830. The first housing 606 may include an exterior surface 608 and an interior surface 610. The first housing 606 includes a handle portion 612 extending from the second end 604 of the instrument 600 towards the first end 602. The handle portion 612 includes a first end 614 and a second end 616. The first end 614 engages a sheath portion or blade holder 650. The sheath portion 650 extends from the first end 614 of the handle portion 612 to the first end 602 of the release instrument 600. The first housing 606 may be, for example, a singular integral or monolithic piece (i.e., of one-piece construction), or may be formed from a plurality of components that are coupled (e.g., rigidly coupled) together to form the coupled handpiece 606, 662. The first housing 606 may also include a recessed region 618 extending into a top surface of the first housing 606. The first housing 606 may further include an opening 620 extending from the exterior surface 608 of the first housing 606 into the interior surface 610 through the recessed region 618. A switch 760 may be positioned to engage the recessed region 618 and the opening 620.

Figure 48:
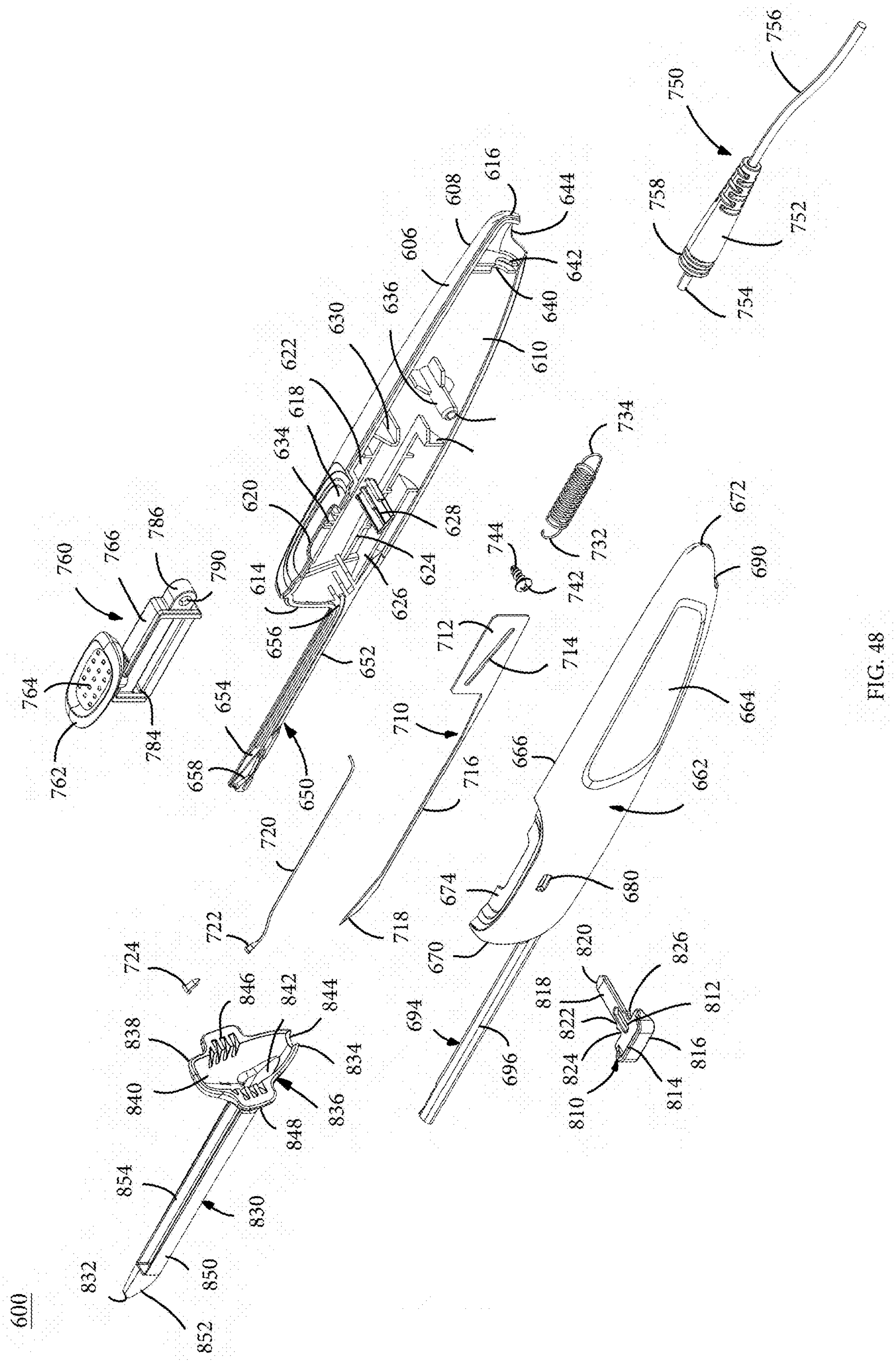
FIG. 48 is a second exploded, perspective view of the release instrument of FIG. 35, in accordance with an aspect of the present disclosure.
Figure 49:
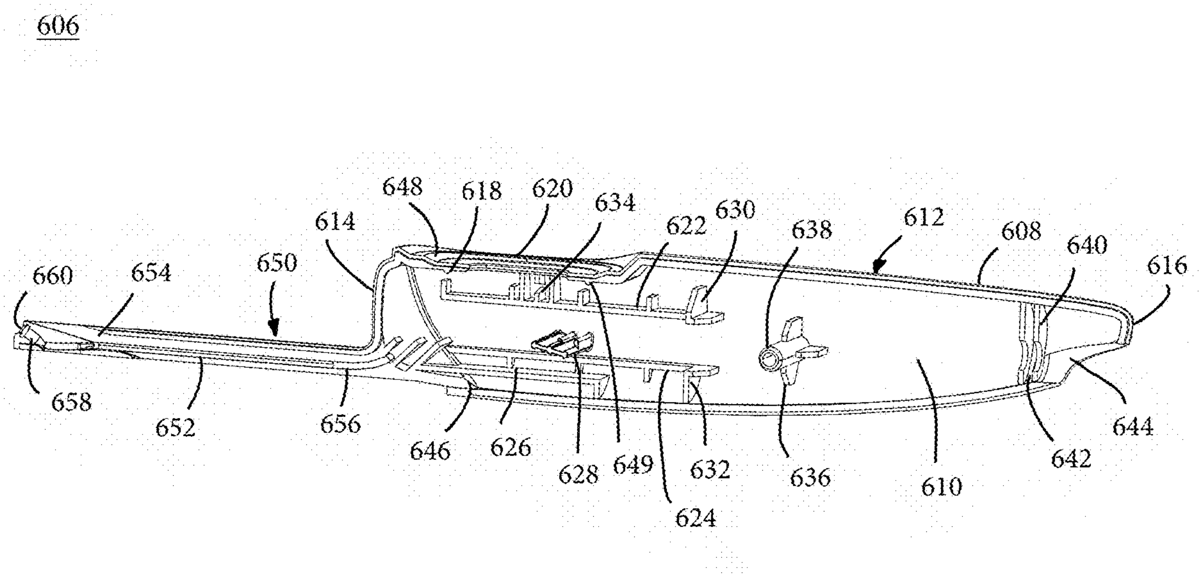
FIG. 49 is a perspective view of the first housing of the release instrument of FIG. 35, in accordance with an aspect of the present disclosure.

As shown in FIGS. 48-49, the interior surface 610 of the first housing 606 may include a plurality of support structures or frames 622, 624, 626. The plurality of support structures or supports 622, 624, 626 provide a guide or track for assisting with translation of the switch 760. The plurality of support structures or supports 622, 624, 626 include a first support structure or upper support 622 positioned on the interior surface 610 inferior to the opening 620. The upper support 622 may be positioned near a top surface of the handle portion 612. The upper support 624 has a length extending between the first end 614 and the second end 616 of the first housing 606. The length may be, for example, longer than the recessed region 618. The upper support 622 may have a first end positioned near the first end 614 of the first housing 606 and the first end of the upper support 622 may be positioned inferior to a first end of the recessed region 618. The upper support 622 may include a horizontal member and a plurality of vertical members extending away from a top surface of the horizontal member. At least two of the vertical members of the upper support 622 may form a locking slot 634 for receiving a safety tab or locking member 810. In addition, at least one vertical member may be separated into two portions by the locking slot 634. A first portion of the at least one vertical member may have an angled upper or top surface and a second portion of the at least one vertical member may have an angled lower or bottom surface, for example to correspond to an engagement surface of the safety tab 810. The locking slot 634 may be positioned adjacent to at least a portion of the opening 620. The upper support 622 may also include a first switch stop member or stop member 630 positioned at the second end of the upper support 622. The first stop member 630 may be, for example, coupled to or integral with the upper support 622 at a second end. The stop member 630 may be positioned, for example, near a midpoint of the handle portion 612 between the first end 614 and the second end 616. The stop member 630 may include a horizontal base member and a vertical member. The vertical member may extend away from a top surface of the horizontal base member and may be configured or sized and shaped to engage a second end of the switch base 766.

With continued reference to FIGS. 48-49, the plurality of support structures 622, 624, 626 also include a second support structure or lower support 624 positioned on the interior surface 610 inferior to the upper support 622. The lower support 624 may be positioned near a bottom surface of the handle portion 612. The lower support 624 has a length extending between the first end 614 and the second end 616 of the first housing 606. The length may be, for example, longer than the recessed region 618. The lower support 624 may have a first end positioned near the first end 614 of the first housing 606 and the first end of the lower support 624 may be positioned inferior to the first end of the recessed region 618. The lower support 624 may include a horizontal member and a plurality of vertical members extending away from a bottom surface of the horizontal member. The lower support 624 may also include a second switch stop member or stop member 632 positioned at the second end of the lower support 624. The second stop member 632 may be, for example, coupled to or integral with the lower support 624 at a second end. The stop member 632 may be positioned, for example, near a midpoint of the handle portion 612 between the first end 614 and the second end 616. The stop member 632 may include a horizontal base member and a vertical member. The vertical member may extend away from the bottom surface of the horizontal base member and may be configured or sized and shaped to engage a second end of the switch base 766.

The plurality of support structures 622, 624, 626 also includes a third support structure or bottom support 626 positioned on the interior surface 610 inferior to the lower support 624, as shown in FIGS. 48-49. The bottom support 626 may be, for example, positioned between the vertical members of the lower support 624 and a bottom surface of the handle portion 612. The bottom support 626 has a length extending between the first end 614 and the second end 616 of the first housing 606. The length of the bottom support 626 may be, for example, shorter than the lengths of the upper and lower supports 622, 624. The bottom support 626 may include a horizontal member and a vertical member. The horizontal member of the bottom support 626 may, for example, extend away from the interior surface 610 farther than the horizontal members of the upper support 622 and lower support 624. The horizontal member of the bottom support 626 may, for example, in one embodiment provide additional support for the switch base 766 during translation of the switch 760. In alternative embodiments, the horizontal member of the bottom support 626 does not contact the switch base 766 and only provides additional support to the first housing 626.

A blade support member or frame 628 is also shown in FIGS. 48-49. The blade support member 628 is positioned between the upper support 622 and lower support 624. The support member 628 extends away from the interior surface 610 of the first housing 606. The support member 628 has a width extending from the interior surface 610 of the first housing 606 toward an interior surface 666 of the second housing 662. The width of the support member 628 is larger than the width of the first housing 606. The support member 628 extends beyond the walls of the first housing 606, for example, to allow for engagement with a portion of the second housing 662. The support member 628 is also angled or slanted as it extends between the first end 614 and the second end 616 of the first housing 606. The support member 628 is, for example, angled such that the first end of the support member 628 is positioned closer to the top surface the first housing 606 than the second end of the support member 628. The support member 628 may also include a plurality of protrusions and/or surface textures extending away from the support member 628 to assist with engaging and positioning of the blade member 710. For example, the support member 628 may include protrusions extending away from the interior surface 610 of the first housing 606 to position the blade member 710 a desired distance from the interior surface 610 for positioning the blade member 710 to translate within the sheath portion 650.

The interior surface 610 of the first housing 606 may also include a male coupling member 636, as shown in FIGS. 48-49. The male coupling member 636 extends away from the interior surface 610 of the first housing 606 toward the interior surface 666 of the second housing 662. The male coupling member 636 may have, for example, a cylindrical shape and leg members extending away from an exterior surface 638 of the male coupling member 636. The coupling member 636 has a width extending from the interior surface 610 of the first housing 606 toward an interior surface 666 of the second housing 662. The width of the coupling member 636 is larger than the width of the first housing 606. The coupling member 636 extends beyond the walls of the first housing 606, for example, to allow for engagement with a portion of the second housing 662.

Further, the interior surface 610 includes at least one cable support member 640, as shown in FIGS. 48-49. The at least one cable support member 640 may be, for example, two support members 640. Each of the at least one cable support members 640 may extend away from the interior surface 610 of the first housing 606 near the second end 616. The support members 640 may include a recess 642 inset into a portion of the support members 640 from the open side of the first housing 606 toward the interior surface 610 of the first housing 606. The recesses 642 may be, for example, configured or sized and shaped to couple to a portion of the cable attachment member 750. The second end 616 of the first housing 606 may also include a cable opening 644 positioned adjacent to the at least one support member 640. The opening 644 may extend through the first housing 606 from an exterior surface 608 to an interior surface 610 allowing for the cable attachment member 750 to pass from the interior of the release instrument 600 to the exterior of the release instrument 600.

With continued reference to FIGS. 48-49, the first housing 606 also includes a blade arm opening 646. The opening 646 is positioned near a first end 614 of the first housing 606. In addition, the opening 646 is positioned near a bottom surface of the first housing 606. The opening 646 is, for example, configured or sized and shaped to receive a portion of the blade arm 716 as the blade arm 716 extends from the handle portion 612 of the first housing 606 to the sheath portion 650 of the first housing 606. In addition, the interior surface 610 of the handle portion 612 of the first housing 606 includes a first tab 648 and a second tab 649 extending away from the interior surface 610 inferior to the recessed region 618. The first tab 648 is positioned near a first end of the opening 620 and the second tab 649 is positioned near a second end of the opening 620. The tabs 648, 649 may have, for example, a semi-circular shape and may extend the entire width of the wall at the top of the first housing 606. The tabs 648, 649 may be, for example, configured or sized and shaped to engage a portion of the switch 760.

The sheath portion or blade holder 650 may also be seen in FIGS. 48-49. The sheath portion 650 is coupled to and extends from the first end 614 of the handle portion 612. The sheath portion 650 may include a blade arm channel 652 inset into a portion of the interior of the sheath portion 650. The channel 652 may extend from the opening 646 to a first end 602 of the release instrument 600. The channel 652 may be, for example, inset into the sheath portion 650 of the first housing 606 the entire width of the blade member 710 or only a portion of the width of the blade member 710. The sheath portion 650 may also include a blade slot 654 extending from the channel 652 at a bottom of the sheath portion 650 to a top of the sheath portion 650. The blade slot 654 is angled as it extends from the channel 652 to a position near the first end of the sheath portion 650. The blade slot 654 may be, for example, configured or size and shaped to correspond to the shape of the blade 718. The sheath portion 650 may also include a cable channel 656 extending through the first end 614 of the first housing 606 and inset into the sheath portion 650. The cable channel 656 may be inset into the sheath portion 650 more than the blade channel 652. A portion of the cable channel 656 may overlap with a portion of the blade channel 652 where the blade 718 is deployed from the sheath portion 650 of the first housing 606. The sheath portion 650 also includes a camera slot 658 for receiving a camera connector 722 and a camera 724. The slot 658 may be, for example, configured or sized and shaped to correspond the camera 724 being used in the release instrument 600. The sheath portion 650 further includes a camera opening 660 at the first end extending from an exterior surface of the sheath portion 650 into the camera slot 658. The opening 660 provides a window for the camera 724 to view the surrounding tissues and other structures during surgery.

Figure 47:
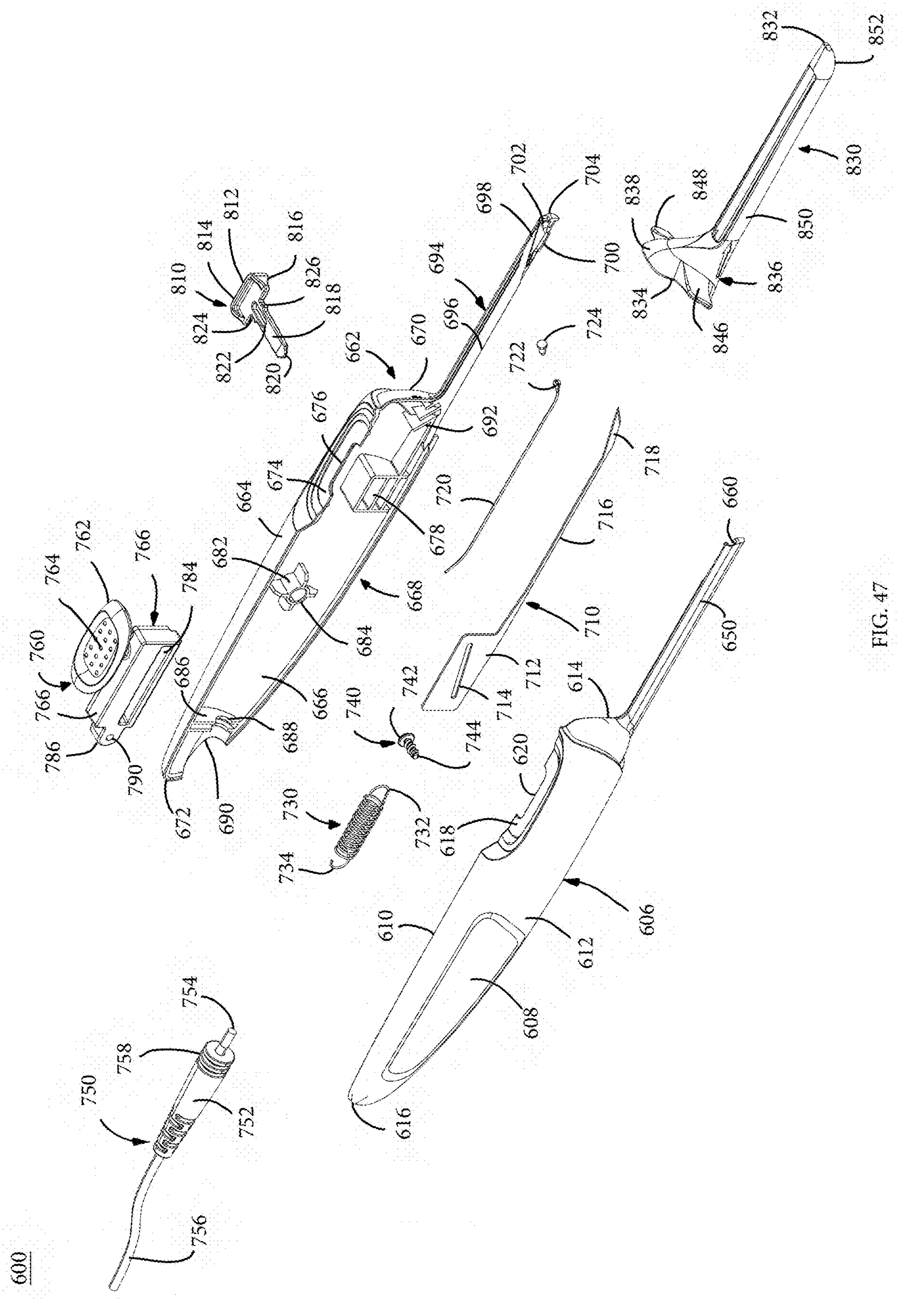
FIG. 47 is a first exploded, perspective view of the release instrument of FIG. 35, in accordance with an aspect of the present disclosure.
Figure 50:
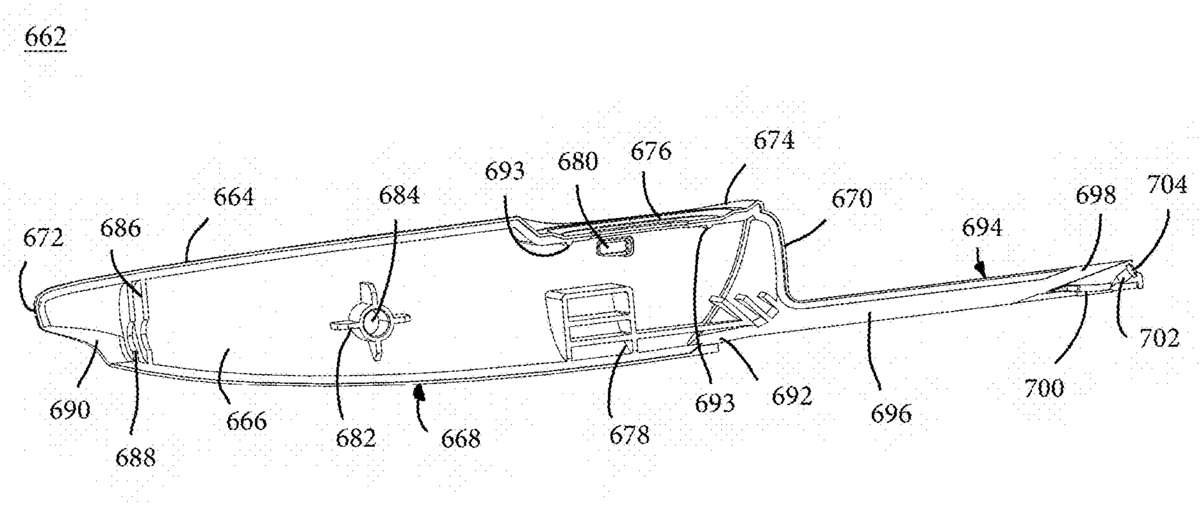
FIG. 50 is a perspective view of the second housing of the release instrument of FIG. 35, in accordance with an aspect of the present disclosure.

Referring now to FIGS. 47 and 50, the second housing 662 is shown. The second housing 662 includes an exterior surface 664 and an interior surface 666. The second housing 662 also includes a handle portion 668 and a sheath portion 694 coupled to and extending away from the handle portion 668. The handle portion 668 may include a first end 670 and a second end 672 opposite the first end 670. The sheath portion 694 may extend away from the first end 670 of the handle portion 668. The second housing 662 may be, for example, a singular integral or monolithic piece (i.e., of one-piece construction), or may be formed from a plurality of components that are coupled (e.g., rigidly coupled) together to form the second housing 662. The second housing 662 may also include a recessed region 674 extending into a top surface of the second housing 662. The second housing 662 may further include an opening 676 extending from the exterior surface 664 of the second housing 662 into the interior surface 666 through the recessed region 674. The recessed region 674 and opening 676 are mirror images of the recessed region 618 and opening 620, respectively, of the first housing 606. The recessed region 674 and recessed region 618 couple together to form a single recessed region 618, 674 for receiving a portion of the switch 760. The opening 676 and opening 620 couple together to form a single opening 620, 676 for receiving a portion of the switch 760 as it extends from the exterior surfaces 608, 664 to the interior surfaces 610, 666 of the release instrument 600. The switch 760 may be positioned to engage the recessed regions 618, 674 and the openings 620, 676.

The interior surface 666 also includes a support structure or frame 678, as shown in FIGS. 47 and 50. The support structure 678 includes horizontal and vertical members. For example, the support structure 678 includes three horizontal members and two vertical members. The three horizontal members may include a first horizontal member that is longer than the second and third horizontal members. The horizontal members may be connected by two vertical members to form two slots positioned superior to the first horizontal member. The superior most slot may be, for example, configured or sized and shaped to receive a portion of the blade support member 628. Additionally, the support structure 678 may engage the base 712 of the blade member 710 to maintain the coupling of the blade member 710 with the blade support member 628. The blade member 710 may translate relative to the support structure 678 to deploy and retract the blade 718 from the cannula 830 of the release instrument 600. The support structure 678 may be positioned near a bottom of the second housing 662.

With continued reference to FIGS. 47 and 50, the second housing 662 includes a through hole or safety tab hole 680 extending through the second housing 662 from the exterior surface 664 to the interior surface 666. The through hole 680 may be positioned inferior to the recessed region 674 and opening 676. The through hole 680 may be, for example, configured or sized and shaped to receive a shaft 818 of the safety tab 810. In addition, the second housing 662 includes a female coupling member 682 positioned on and extending away from the interior surface 666 of the second housing 662 toward the interior surface 610 of the first housing 606. The coupling member 682 may have, for example, a cylindrical shape and leg members extending away from an exterior surface of the female coupling member 682. The coupling member 682 may also include an opening 684 extending into the female coupling member 682 from the open side of the second housing 662. The opening 684 may be, for example, configured or sized and shaped to receive a portion of the male coupling member 636. The coupling member 682 has a width extending from the interior surface 666 of the second housing 662 toward an interior surface 610 of the first housing 606. The width of the coupling member 682 is smaller than the width of the second housing 662.

Further, the interior surface 666 includes at least one cable support member 686, as shown in FIGS. 47 and 50. The at least one cable support member 686 may be, for example, two support members 686. Each of the at least one cable support members 686 may extend away from the interior surface 666 of the second housing 662 near the second end 672. The support members 686 may include a recess 688 inset into a portion of the support members 686 from the open side of the second housing 662 toward the interior surface 666 of the second housing 662. The recesses 688 may be, for example, configured or sized and shaped to couple to a portion of the cable attachment member 750. The second end 672 of the second housing 662 may also include a cable opening 690 positioned adjacent to the at least one support member 686. The cable opening 690 may extend through the second housing 662 from an exterior surface 664 to an interior surface 666 allowing for the cable attachment member 750 to pass from the interior of the release instrument 600 to the exterior of the release instrument 600.

With continued reference to FIGS. 47 and 50, the second housing 662 also includes a blade arm opening 692. The opening 692 is positioned near a first end 670 of the second housing 662. In addition, the opening 692 is positioned near a bottom surface of the second housing 662. The opening 692 is, for example, configured or sized and shaped to receive a portion of the blade arm 716 as the blade arm 716 extends from the handle portion 612 of the second housing 662 to the sheath portion 694 of the second housing 662. In addition, the interior surface 666 of the handle portion 668 of the second housing 662 includes at least one tab 693 extending away from the interior surface 666 inferior to the recessed region 674. The at least one tab 693 may include a first tab 693 positioned toward the first end 670 and a second tab 693 positioned toward the second end 672. In addition, the first tab 693 is positioned near a first end of the opening 676 and the second tab 693 is positioned near a second end of the opening 676. The tabs 693 may have, for example, a semi-circular shape and may extend the entire width of the wall at the top of the second housing 662. The tabs 693 may be, for example, configured or sized and shaped to engage a portion of the switch 760.

The sheath portion or blade holder 694 may also be seen in FIGS. 47 and 50. The sheath portion 694 is coupled to and extends from the first end 670 of the handle portion 668. The sheath portion 694 may include a blade arm channel 696 inset into a portion of the interior of the sheath portion 694. The channel 696 may extend from the opening 692 to a first end 602 of the release instrument 600. The channel 696 may be, for example, inset into the sheath portion 694 of the second housing 662 the entire width of the blade member 710 or only a portion of the width of the blade member 710. When assembled the channels 652, 696 combine together to form a channel 652, 696 that is at least as large as the width of the blade member 710 to allow for translation of the blade arm 716 through the channel 652, 696. The sheath portion 694 may also include a blade slot 698 extending from the channel 696 at a bottom of the sheath portion 694 to a top of the sheath portion 694. The blade slot 698 is angled as it extends from the channel 696 to a position near the first end of the sheath portion 694. The blade slot 698 may be, for example, configured or size and shaped to correspond to the shape of the blade 718. The sheath portion 694 may also include a cable channel inset into a portion of the sheath portion 694. The blade channel 696 may be inset into the sheath portion 694 more than the cable channel 700. A portion of the cable channel 700 may overlap with a portion of the blade channel 696 where the blade 718 is deployed from the sheath portion 694 of the second housing 662. The sheath portion 694 also includes a camera slot 702 for receiving a camera connector 722 and a camera 724. The slot 702 may be, for example, configured or sized and shaped to correspond the camera 724 being used in the release instrument 600. The sheath portion 694 further includes a camera opening 704 at the first end extending from an exterior surface of the sheath portion 694 into the camera slot 702. The opening 704 provides a window for the camera 724 to view the surrounding tissues and other structures during surgery.

Referring now to FIGS. 43-48, the blade member 710 is shown. The blade member 710 includes a base 712, an arm 716 coupled to the base 712 on a first end, and a blade 718 coupled to the arm 716 on a second end. The base 712 may have, for example, a rectangular shape. The base 712 may also include a slot 714 extending through the base 712 from a first side to a second side. The slot 714 may be, for example, angled or slanted as it extends from a first end to a second end. The angle of the slot 714 may, for example, correspond to the angle of the blade support member 628. The slot 714 may also be configured or sized and shaped to receive at least a portion of the blade support member 628 of the first housing 606. The blade member 710 may also include an arm 716 extending away from the first end of the base 712. The arm 716 may be, for example, positioned at and coupled to a bottom or inferior end of the base 712. The blade member 710 may also include a blade or cutting end 718 coupled to and extending from a second end of the arm 716. The cutting end 718 may extend from the arm 716 at an angle greater than 0° and less than 90°, more preferably the angle is between 25° and 40°, and most preferably the angle is between 30° and 35°. The cutting end 718 includes a sharp surface for cutting through tendinous, ligamentous, fibrous tissue, and the like. The cutting end 718 may have, for example, a larger height and a smaller length than the arm 716. The blade member 710 may be, for example, a singular integral or monolithic piece (i.e., of one-piece construction), or may be formed from a plurality of components that are coupled (e.g., rigidly coupled) together to form the blade member 710.

With continued reference to FIGS. 43-48, the camera cable 720, camera connector 722 and camera 724 are shown. The camera cable 720 is coupled to the camera connector 722 on a first end and the cable attachment member 750 on a second end. The cable 720 extends from the camera slots 660, 702 through the channels 656, 700, into and through the handle portions 612, 668, and finally couples to the cable attachment member 750 at a second end 604 of the release instrument 600. As the cable 720 extends through the handle portions 612, 668 the cable 720 is positioned to prevent engagement with the other components positioned inside the handle portions 612, 668 of the release instrument 600. The cable 720 may be, for example, at least one wire and/or cable to transmit power to the camera 724 and/or video to a display or a processor of the video unit 102. The at least one wire and/or cable 720 may be, for example, a single wire or separate wires for the camera 724. The camera connector 722 is positioned in the camera slot 658, 702 and couples to a camera 724 also positioned in the camera slot 658, 702. The camera 724 is positioned to align the lens of the camera with the openings 660, 704 to allow for visualization of the surgical field during a procedure. The images collected by the camera 724 are transmitted to a video output through the cables 720, 756.

Also shown in FIGS. 43-48 is a spring 730 with a first end 732 and a second end 734. The first end 732 of the spring 730 has a first hook that is coupled to a portion of the switch 760 by a screw 740. The second end 734 of the spring 730 has a second hook that is coupled to an exterior surface 638 of the male coupling member 636. The spring 730 expands and compresses during translation of the switch 760. The screw 740 includes a head 742 and a shaft or threaded shaft 744. The head 742 engages the first end 732 of the spring 730 to secure the first end 732 of the spring 730 between the head 742 and the switch 760. The shaft 742 of the screw 740 is coupled to an opening 790 in the switch 760.

The cable attachment member 750 is shown in FIGS. 35-40 and 42-48. The attachment member 750 includes a housing or strain relief portion 752 including a plurality of recesses 758 inset into the exterior surface of the housing 752. The plurality of recesses 758 with a shape to correspond to the shapes of the recesses 642, 688 in the cable support portions 640, 686 of the housings 606, 662 of the release instrument 600. For example, the recesses 642, 688 may have circular shapes to correspond to the semi-circular shapes of the recesses 642, 688 of the cable supports 640, 686. The attachment member 750 also includes a connector 754 coupled to and extending from a first end of the housing 752. The attachment member 750 further includes a cable 756 coupled to and extending from the second end of the housing 752. A portion of the housing 752 may be positioned in the cable opening 644, 690.

Referring now to FIGS. 35-53, and more particularly to FIGS. 47, 48 and 51-53, the switch 760 is shown. The switch 760 includes a button 762 coupled to a base 766 by a stem or connecting member 792. The button 762 includes a recessed region 764 on a top surface that may include a textured region. The button 762 and recessed region 764 are, for example, configured or sized and shaped to receive a user's finger to translate the button 762 and in turn deploy and retract the blade 718 from the insertion instrument 600. The connecting member 792 extends through the openings 620, 676 in the housings 606, 662. The button 762 is coupled to a first end of the connecting member 792 to position the button 762 over the recessed regions 618, 674 and spaced apart from the exterior surfaces 608, 664 the housings 606, 662. The base 766 is coupled to a second end of the connecting member 792. The base 766 is also positioned within the interior surfaces 610, 666 of the housings 606, 662. The base 766 includes a first side 768 opposite a second side 770, a first end 772 opposite a second end 774, and a top 776 opposite a bottom 778. The first side 768 includes a recessed region 780 extending from an exterior surface into a portion of the base 766. The recessed region 780 may be, for example, configured or sized and shaped to receive the base 712 of the blade member 710. The recessed region 780 may form a rim or wall around a portion of the first side 768 to assist with retaining the blade member 710 within the recessed region 780. The first side 768 may also include a cutout 782 on a first end near a bottom of the base 766. The cutout 782 is inset into the rim surrounding the recessed region 780. The cutout 782 may be, for example, configured or sized and shaped to receive the arm 716 of the blade member 710.

The base 766 may further include a slot 784 extending through the base 766 from a first side 768 to a second side 770, as shown in FIGS. 47, 48, 51 and 52. The slot 784 may have, for example, a rectangular shape that extends from a position near the first end 772 to a position near the second end 774. The slot 784 allows for the blade support member 628 to pass through the base 766 and engage the slot 714 of the blade member 710. In addition, the base 766 may include a tab 786 extending away from the second end 774 of the base 766. The tab 786 may include an exterior surface 788 and a through hole 790. The through hole 790 extending through the tab 786 from the exterior surface 788 on a first side to the exterior surface 788 on a second side. The through hole 790 may be, for example, threaded to receive the threaded shaft 744 of the screw 740 to secure the first end of the spring 730 to the tab 786 of the base 766. The head 742 of the screw 740 may engage a portion of the first side of the exterior surface 788 and secure the first hook on the first end 732 of the spring 730 between the head 742 and the first side of the tab 786.

In addition, the connecting member 792 of the switch 760 may include a first arm or wing 794 and a second arm or wing 798, as shown in FIGS. 47, 48, 51 and 52. The first arm 794 extends from the connecting member 792 in the direction of the first end 772 of the base 766. The first arm 794 may be, for example, positioned near a midpoint between a top surface 776 of the base 766 and a bottom surface of the button 762. The first arm 794 may also include a first projection 796 extending away from a top surface of the first arm 794. The first projection 796 may extend the entire width of the first arm 794. The first projection 796 may be, for example, semi-circular or round shaped. The first projection 796 may be, for example, configured or sized and shaped to engage the first tabs 648, 693 on the interior surface 610, 666 of the housings 606, 662. The tabs 648, 693 and projection 796 assist with retaining the switch 760 within the desired range of translation.

The second arm 798 extends from the connecting member 792 in the direction of the second end 774 of the base 766. The second arm 798 may be, for example, positioned near a midpoint between the top surface 776 of the base 766 and the bottom surface of the button 762. The second arm 798 may also include a second projection 800 extending away from a top surface of the second arm 798. The second projection 800 may extend the entire width of the second arm 798 between the first side and the second side of the second arm 798. The second projection 899 may be, for example, semi-circular or round shaped. The second projection 800 may be, for example, configured or sized and shaped to engage the second tabs 649, 693 on the interior surface 610, 666 of the housings 606, 662. The tabs 649, 693 and projection 800 assist with retaining the switch 760 within the desired range of translation.

Figure 51:
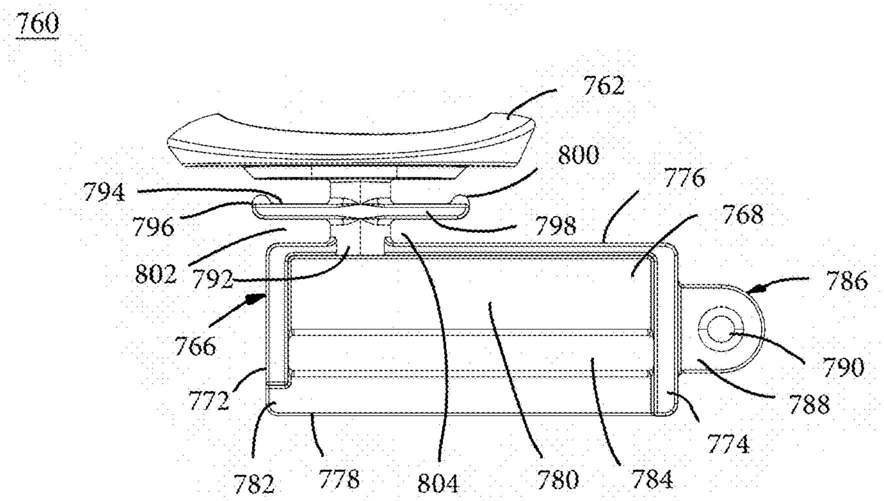
FIG. 51 is a first side view of a switch of the release instrument of FIG. 35, in accordance with an aspect of the present disclosure.
Figure 52:
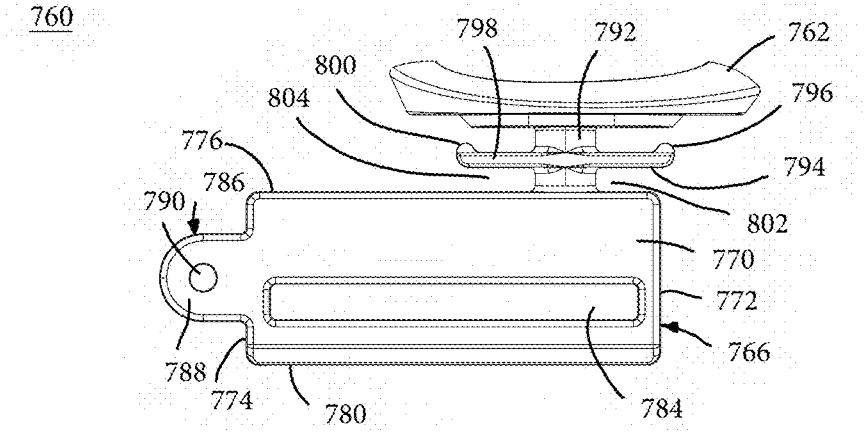
FIG. 52 is a second side view of the switch of the release instrument of FIG. 35, in accordance with an aspect of the present disclosure.
Figure 53:
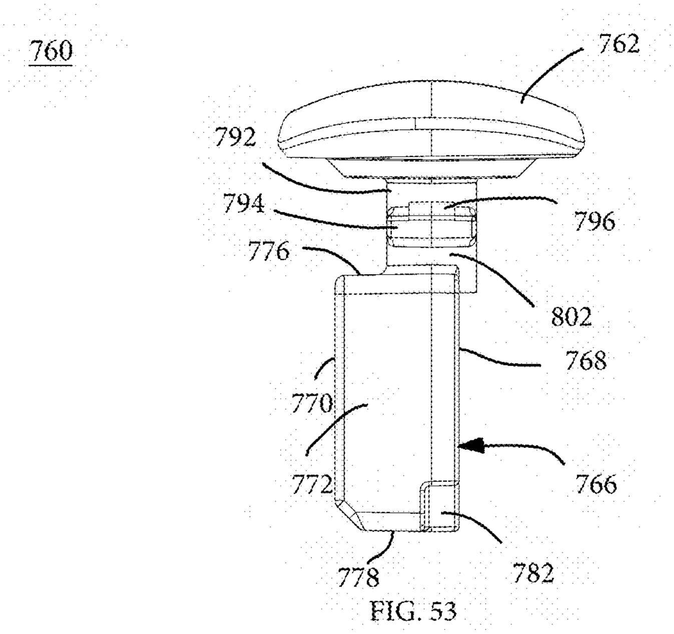
FIG. 53 is a first end view of the switch of the release instrument of FIG. 35, in accordance with an aspect of the present disclosure.
Figure 54:
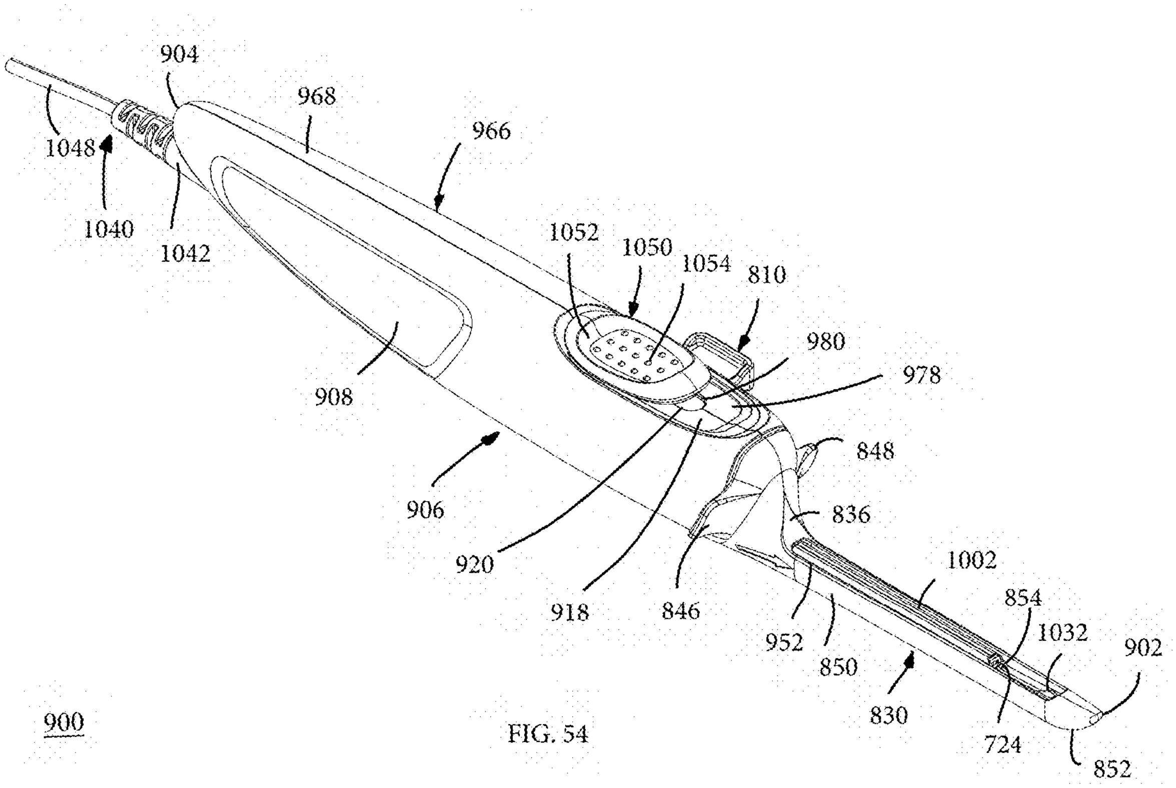
FIG. 54 is a first perspective view of yet another release instrument, in accordance with an aspect of the present disclosure.
Figure 55:
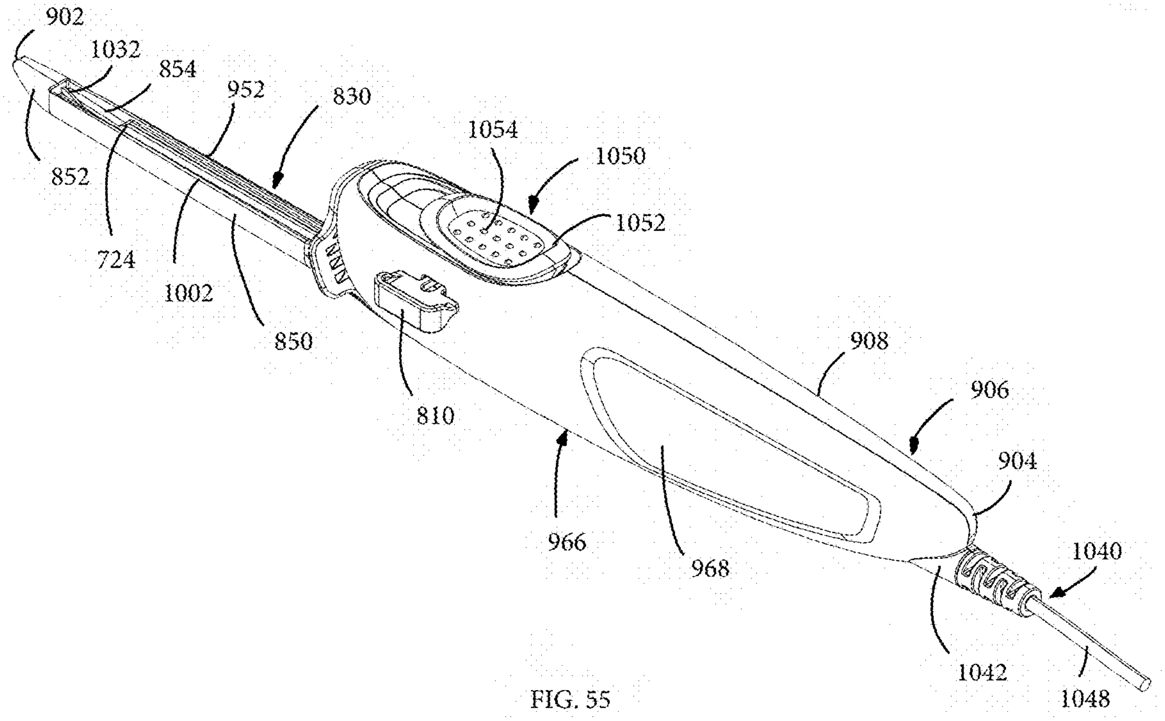
FIG. 55 is a second perspective view of the release instrument of FIG. 54, in accordance with an aspect of the present disclosure.
Figure 56:
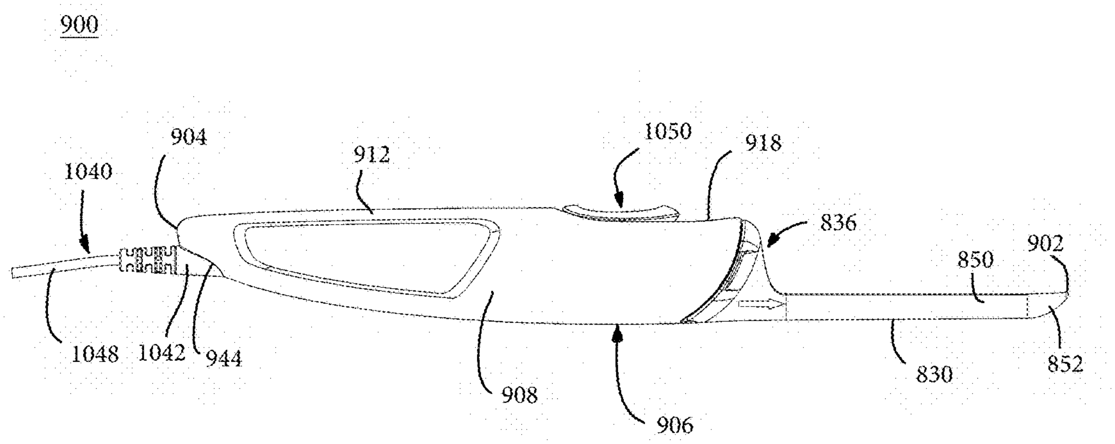
FIG. 56 is a first side view of the release instrument of FIG. 54, in accordance with an aspect of the present disclosure.

With continued reference to FIGS. 51 and 52, the switch 760 may also include a first locking channel or undeployed channel 802 and a second locking channel or deployed locking channel 804. The first and second locking channels 802, 804 are configured and/or sized and shaped to receive a portion of the shaft 818 of the safety tab 810. The first locking channel 802 is positioned between the top surface 776 of the base 766 and a bottom surface of the first arm 794. The second locking channel 804 is positioned between the top surface 776 of the base 766 and a bottom surface of the second arm 798. When the safety tab 810 is inserted into the first locking channel 802 the switch 760 is secured in a first position or undeployed position. When the safety tab 810 is inserted into the second locking channel 804 the switch 760 is secured in a second position or deployed position.

Figure 46:
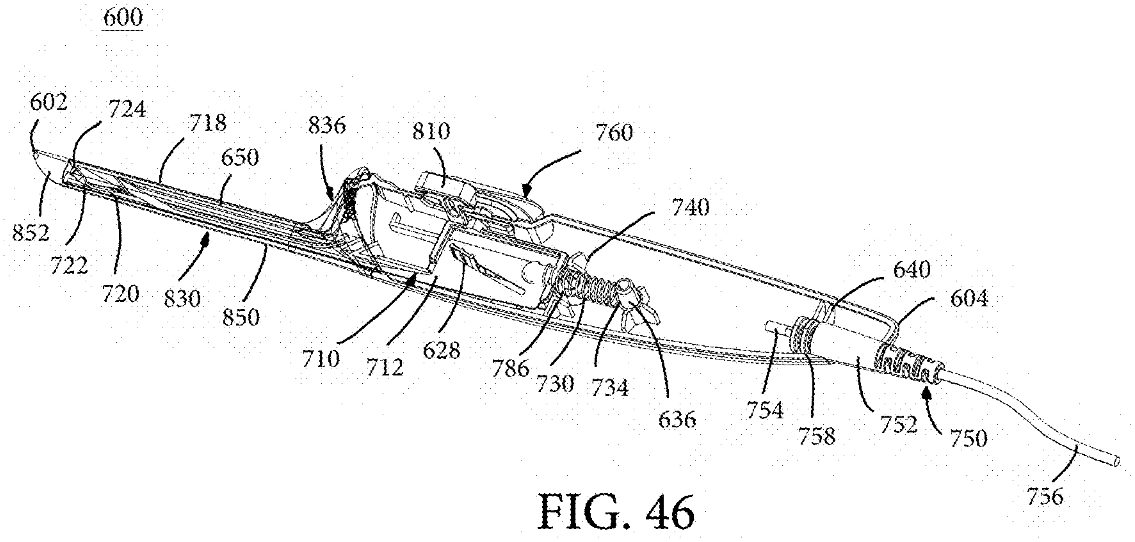
FIG. 46 is a perspective, side view of the release instrument of FIG. 35 with the second housing removed and a transparent cannula, in accordance with an aspect of the present disclosure.

Referring now to FIGS. 46-48, the safety tab or locking member 810 is shown. The safety tab 810 includes a base 812 and a shaft 818 coupled to and extending from the base 812. The base 812 may have, for example, a generally rectangular shape. The base 812 may also include a first wall 814 coupled to and extending away from a top surface of the base 812 around at least a portion of three sides of the base 812. The base 812 may also include a second wall 816 coupled to and extending away from a bottom surface of the base 812 around at least a portion of three sides of the base 812. The first and second walls 814, 816 may each include a portion on the first end of the base 812, a first side portion extending along at least a portion of the first side of the base 812, and a second side portion extending along at least a portion of the second side of the base 812. The wall portion on the first end of the base 812 extends from the first side to the second side of the base 812. The first side portion of the walls 814, 816 may be tapered or angled as the first side portion extends from the wall portion on the first end of the base 812 toward the second end. The second side portion of the walls 814, 816 may also be tapered or angled as the second side portion extends from the wall portion on the first end of the base 812 toward the second end.

The shaft 818 of the safety tab 810 may include an engagement end 820 at the second end of the shaft 818. The engagement end 820 may be tapered, for example, to form a triangularly shaped end. The shaft 818 may also include a through hole 822 extending through the shaft 818 from a top surface to a bottom surface. The through hole 822 may have, for example, an oval shape. In addition, the shaft 818 may include a first protrusion 824 extending away from a first side surface of the shaft 818. Further, the shaft 818 may include a second protrusion 826 extending away from a second side surface of the shaft 818.

Referring now to FIGS. 35-48, the cannula 830 is shown. The cannula 830 may include a first end or insertion end 832 and a second end 834. The second end 834 is configured and/or sized and shaped to couple to the first and second housings 606, 662. The cannula 830 may include a base 836 position at the second end 834 of the cannula 830 and an extension member 850 coupled to and extending from the base 836 to the insertion end 832. The base 836 includes an exterior surface 838 that may engage or contact the patient's skin and an interior surface 840 that engages or contacts the coupled housings 606, 662. The base 836 may also include a through hole 842 extending through the base 836 from the interior surface 840 to the exterior surface 838 and into extension member 850. The base 836 may further include a recess 844 inset into a bottom portion of the base 836 and extending through the base 836 from the interior surface 840 to the exterior surface 838. The recess 844 may be, for example, configured and/or sized and shaped to receive a corresponding protrusion of the coupled housings 606, 662 of the release instrument 600. The base 836 may further include a first wing 846 and a second wing 848 positioned on opposite sides of the base 836. The first wing 846 may be coupled to and extend away from a first side of the base 836. The second wing 848 may be coupled to and extend away from a second side of the base 836. The wings 846, 848 may, for example, provide for a position to place the user's fingers during insertion, as well as assist with insertion and removal of the cannula 830 onto the coupled housings 606, 662. The extension member 850 may include a leading end 852 at the first end 832. The leading end 852 may be, for example, tapered, curved, or stepped from a bottom surface toward the top surface and from the first and second side surfaces to a tip at the end of the first end 832. The leading end 852 may also be, for example, curved between a first or right side and a second or left side of the cannula 830. The extension member 850 may also include channel 854 recessed into a top surface of the cannula 830. The channel 854 may extend into the cannula 830, for example, to give the cannula 830 a U-shaped cross-section along a majority of the length of the cannula 830. The cannula 830 may have, for example, rounded edges along the length of the cannula 830. The channel 854 may extend from the base 836 to a position adjacent to the leading end 852. The channel 854 may open into the through hole 842 to allow for insertion of the coupled sheath portions 650, 694 for deployment of the blade 718 for cutting tendinous, ligamentous, fibrous tissue, and the like. At least a portion of the cannula 830 may be, for example, clear or opaque. For example, the cannula 830 may be made of a transparent plastic, such as, polycarbonate or a more rigid opaque polyarylamide. When at least a portion of the cannula 830 is clear, the camera 724 may allow for visualization not only through the channel 854 of the cannula 830, but also through that clear portion of the extension member 850.

With continued reference to FIGS. 35-53, the camera cable 720 is positioned within the cable channel 656 and the camera slot 658, extends through the handle portion 612 of the first housing 606, and couples to the connector 754 of the cable attachment member 750. The camera or camera sensor 724 is coupled to the camera connector 722 and positioned within the camera slot 658. The camera cable 720 may be, for example, directly coupled to the connector 754 or indirectly coupled to the connector 754 with additional electrical components, such as, additional cables, circuit boards, bridge circuit boards, and the like. The cable attachment member 750 is positioned to engage the at least one cable support 640 and extend out of the release instrument 600 through the cable opening 644, 690 formed by the coupled housings 606, 662. The switch or translating member 760 is positioned within the first housing 606. The slot 784 of the switch 760 is moveably coupled to the blade support member 628. The stem 792 of the switch 760 is positioned within the opening 620 of the first housing 606 to position the base 766 of the switch 760 to engage the upper support 622, lower support 624, and the bottom support 626. The tab 786 of the switch 760 may receive the screw 740 to couple the first end 732 of the spring 730 to the switch 760 to allow for the spring to expand and contract when the switch 760 is translated. The second end 734 of the switch 760 engages the male coupling member 636 of the housing 606 to secure the second end 734 to the housing 606. The blade member 710 is positioned adjacent to the base 766 of the switch 760 in the recessed region 780. The blade support member 628 is inserted into the slot 714 of the blade member 710 and the arm 716 is positioned in the blade arm channel 652. When the spring is in an undeployed position the cutting end 718 is also undeployed. The second housing 662 is coupled to the first housing 606 by aligning and engaging the male coupling member 636 with the female coupling member 682. Specifically, the exterior surface 638 of the male coupling member 636 is inserted into the opening 684 of the female coupling member 682. Once the first housing 606 is coupled to the second housing 662, the connecting member 792 of the switch 760 is positioned in the opening 676 of the switch 760. The safety tab 810 is then inserted into the through hole 680 of the second housing 662 and engages the locking slot 634 of the first housing 606. The shaft 818 of the safety tab 810 also engages the first locking channel 802 in the undeployed position. The safety tab 810 may be partially removed from the coupled housings 606, 620 to disengage the shaft 818 from the first locking channel 802. The switch 760 may be translated to deploy at least a portion of the cutting end 718 of the blade member 710 above cannula 830. Then, the safety tab 810 may be released to engage the shaft 818 with the second locking channel 804. After the cutting is complete, the safety tab 810 may be removed from the second locking channel 804 and the switch 760 translated back to retract the blade member 710 to the undeployed position. Once in the undeployed position, the safety tab 810 may be reinserted into the first locking channel 802.

Referring now to FIGS. 54-72, another insertion instrument 900 is shown for use in a retrograde videoscope arthroscopic system. The system may also include a video unit 102, as described in greater detail above and which will not be described again here for brevity's sake. The insertion instrument 900 may be, for example, a videoscopic, single-use, disposable, arthroscopic instrument for minimally invasive, endoscopic, tissue release surgery in a patient's joints or limbs. Specifically, the instrument 900 may be used for tissue release procedures in the wrist, foot, and elbow for cutting tendinous, ligamentous, fibrous tissue, and the like. The release instrument 900 may include a first end 902 and a second end 904 opposite the first end 902. The second end 904 of the release instrument 900 may include a cable attachment member or strain relief member 1040 extending from the release instrument 900 to a video unit 102. The cable member 1040 may include a cable 1048 extending from the release instrument 900 and the cable member 1040 to the video unit 102. The video unit 102 may be, for example, a video display, such as a tablet, video screen, television, and the like, or a video processor that may be separate from or integral with a video display, such as described in greater detail above with reference to FIGS. 1 and 14, which will not be described again here for brevity's sake.

With continued reference to FIGS. 54-72, the instrument 900 may include a handpiece or housing 906, 966 and a cannula 830. The cannula 830 is as described in greater detail above and will not be described again here for brevity's sake. The handpiece 906, 966 may include a first or right housing 906 and a second or left housing 966 coupled together to form the handpiece 906, 966. A portion of the handpiece 906, 966 may be slidingly received within the cannula 830. The first housing 906 may include an exterior surface 908 and an interior surface 910. The first housing 906 includes a handle portion 912 extending from the second end 904 of the instrument 900 towards the first end 902. The handle portion 912 includes a first end 914 and a second end 916. The first end 914 engages a sheath portion or blade holder 952. The sheath portion 952 extends from the first end 914 of the handle portion 912 to the first end 902 of the release instrument 900. The first housing 906 may be, for example, a singular integral or monolithic piece (i.e., of one-piece construction), or may be formed from a plurality of components that are coupled (e.g., rigidly coupled) together to form the first housing 906. The first housing 906 may also include a recessed region 918 extending into a top surface of the first housing 906. The first housing 906 may further include an opening 920 extending from the exterior surface 908 of the first housing 906 into the interior surface 910 through the recessed region 918. A switch 1050 may be positioned to engage the recessed region 918 and the opening 920.

Figure 67:
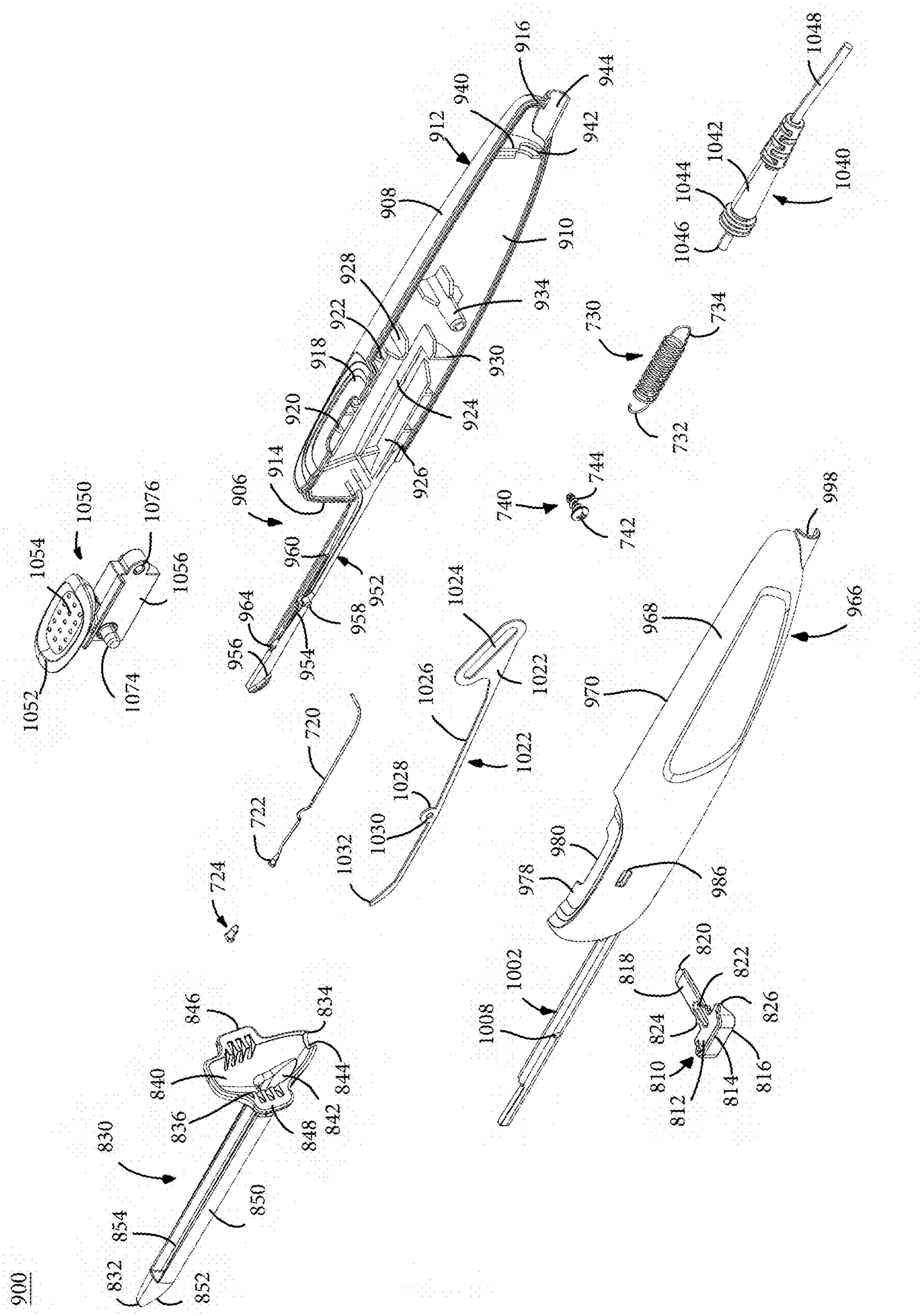
FIG. 67 is a second exploded, perspective view of the release instrument of FIG. 54, in accordance with an aspect of the present disclosure.
Figure 68:
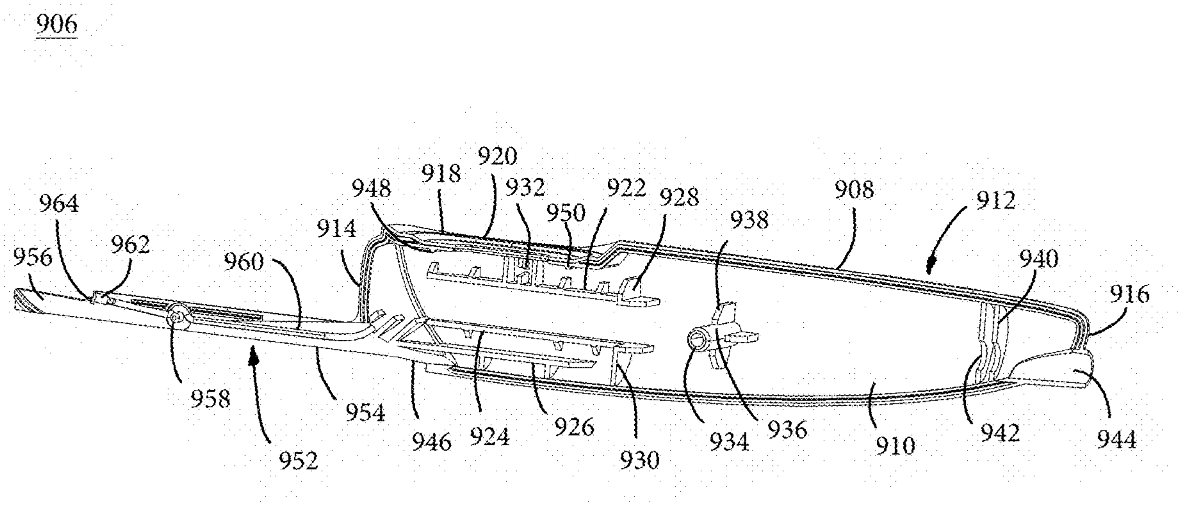
FIG. 68 is a perspective, side view of the first housing of the release instrument of FIG. 54, in accordance with an aspect of the present disclosure.

As shown in FIGS. 67-68, the interior surface 910 of the first housing 906 may include a plurality of support structures or frames 922, 924, 926. The plurality of support structures or supports 922, 924, 926 provide a guide or track for assisting with translation of the switch 1050. The plurality of support structures or supports 922, 924, 926 include a first support structure or upper support 922 positioned on the interior surface 910 inferior to the opening 920. The upper support 922 may be positioned near a top surface of the handle portion 912. The upper support 924 has a length extending between the first end 914 and the second end 916 of the first housing 906. The length may be, for example, longer than the recessed region 918. The upper support 922 may have a first end positioned near the first end 914 of the first housing 906 and the first end of the upper support 922 may be positioned inferior to a first end of the recessed region 918. The upper support 922 may include a horizontal member and a plurality of vertical members extending away from a top surface of the horizontal member. At least two of the vertical members of the upper support 922 may form a locking slot or opening 932 for receiving a safety tab or locking member 810. In addition, at least one vertical member may be separated into two portions by the locking slot 932. A first portion of the at least one vertical member may have an angled upper or top surface and a second portion of the at least one vertical member may have an angled lower or bottom surface, for example to correspond to an engagement surface of the safety tab 810. The locking slot 932 may be positioned adjacent to at least a portion of the opening 920. The upper support 922 may also include a first switch stop member or stop member 928 positioned at the second end of the upper support 922. The first stop member 928 may be, for example, coupled to or integral with the upper support 922 at a second end. The stop member 928 may be positioned, for example, near a midpoint of the handle portion 912 between the first end 914 and the second end 916. The stop member 928 may include a horizontal base member and a vertical member. The vertical member may extend away from a top surface of the horizontal base member and may be configured or sized and shaped to engage a second end of the switch base 1056.

With continued reference to FIGS. 67-68, the plurality of support structures 922, 924, 926 also include a second support structure or lower support 924 positioned on the interior surface 910 inferior to the upper support 922. The lower support 924 may be positioned near a bottom surface of the handle portion 912. The lower support 924 has a length extending between the first end 914 and the second end 916 of the first housing 906. The length may be, for example, longer than the recessed region 918. The lower support 924 may have a first end positioned near the first end 914 of the first housing 906 and the first end of the lower support 924 may be positioned inferior to the first end of the recessed region 918. The lower support 924 may include a horizontal member and a plurality of vertical members extending away from a bottom surface of the horizontal member. The lower support 924 may also include a second switch stop member or stop member 930 positioned at the second end of the lower support 924. The second stop member 930 may be, for example, coupled to or integral with the lower support 924 at a second end. The stop member 930 may be positioned, for example, near a midpoint of the handle portion 912 between the first end 914 and the second end 916. The stop member 930 may include a horizontal base member and a vertical member. The vertical member may extend away from the bottom surface of the horizontal base member and may be configured or sized and shaped to engage a second end of the switch base 1056.

The plurality of support structures 922, 924, 926 also includes a third support structure or bottom support 926 positioned on the interior surface 910 inferior to the lower support 924, as shown in FIGS. 67-68. The bottom support 926 may be, for example, positioned between the vertical members of the lower support 924 and a bottom surface of the handle portion 912. The bottom support 926 has a length extending between the first end 914 and the second end 916 of the first housing 906. The length of the bottom support 926 may be, for example, shorter than the lengths of the upper and lower supports 922, 924. The bottom support 926 may include a horizontal member and a vertical member. The horizontal member of the bottom support 926 may, for example, extend away from the interior surface 910 farther than the horizontal members of the upper support 922 and lower support 924. The horizontal member of the bottom support 926 may, for example, in one embodiment provide additional support for the switch base 1056 during translation of the switch 1050. In alternative embodiments, the horizontal member of the bottom support 926 does not contact the switch base 1056 and only provides additional support to the first housing 906.

The interior surface 910 of the first housing 906 may also include a male coupling member 934, as shown in FIGS. 67-68. The male coupling member 934 extends away from the interior surface 910 of the first housing 906 toward the interior surface 970 of the second housing 966. The male coupling member 934 may have, for example, a cylindrical shape and leg members 938 extending away from an exterior surface 936 of the male coupling member 934. The coupling member 934 has a width extending from the interior surface 910 of the first housing 906 toward an interior surface 970 of the second housing 966. The width of the coupling member 934 is larger than the width of the first housing 906. The coupling member 934 extends beyond the walls of the first housing 906, for example, to allow for engagement with a portion of the second housing 966.

Further, the interior surface 910 includes at least one cable support member 940, as shown in FIGS. 67-68. The at least one cable support member 940 may be, for example, two support members 940. Each of the at least one cable support members 940 may extend away from the interior surface 910 of the first housing 906 near the second end 916. The support members 940 may include a recess 942 inset into a portion of the support members 940 from the open side of the first housing 906 toward the interior surface 910 of the first housing 906. The recesses 942 may be, for example, configured or sized and shaped to couple to a portion of the cable attachment member 1040. The second end 916 of the first housing 906 may also include a cable opening 944 positioned adjacent to the at least one support member 940. The opening 944 may extend through the first housing 906 from an exterior surface 908 to an interior surface 910 allowing for the cable attachment member 1040 to pass from the interior of the release instrument 900 to the exterior of the release instrument 900.

With continued reference to FIGS. 67-68, the first housing 906 also includes a blade arm opening 946. The opening 946 is positioned near a first end 914 of the first housing 906. In addition, the opening 946 is positioned near a bottom surface of the first housing 906. The opening 946 is, for example, configured or sized and shaped to receive a portion of the blade arm 1026 as the blade arm 1026 extends from the handle portion 912 of the first housing 906 to the sheath portion 952 of the first housing 906. In addition, the interior surface 910 of the handle portion 912 of the first housing 906 includes a first tab 948 and a second tab 950 extending away from the interior surface 910 inferior to the recessed region 918. The first tab 948 is positioned near a first end of the opening 920 and the second tab 950 is positioned near a second end of the opening 920. The tabs 948, 950 may have, for example, a semi-circular shape and may extend the entire width of the wall at the top of the first housing 906. The tabs 948, 950 may be, for example, configured or sized and shaped to engage a portion of the switch 1050.

Figure 57:
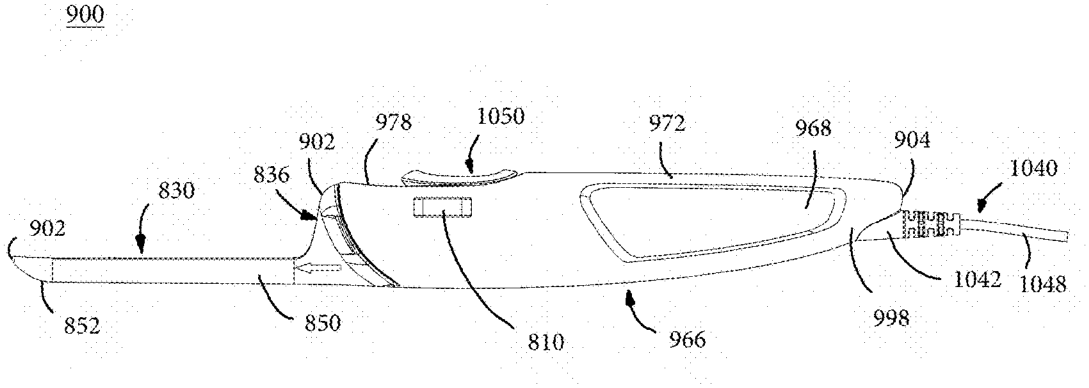
FIG. 57 is a second side view of the release instrument of FIG. 54, in accordance with an aspect of the present disclosure.
Figure 58:
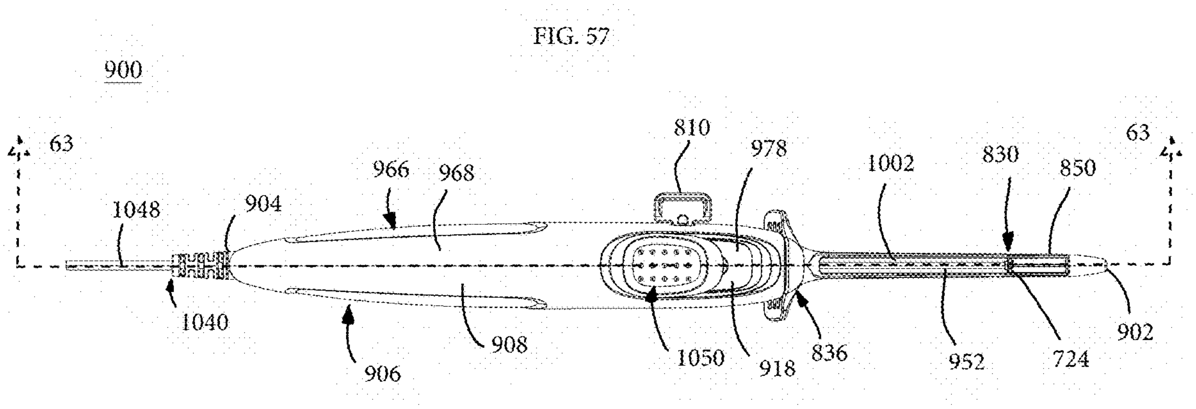
FIG. 58 is a top view of the release instrument of FIG. 54, in accordance with an aspect of the present disclosure.
Figure 59:
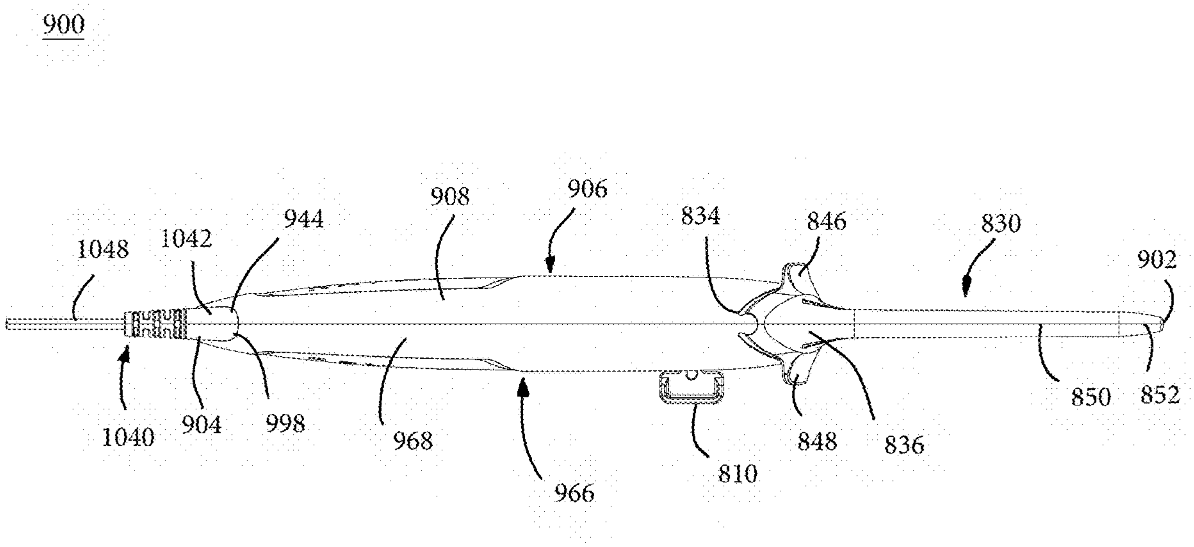
FIG. 59 is a bottom view of the release instrument of FIG. 54, in accordance with an aspect of the present disclosure.
Figure 60:
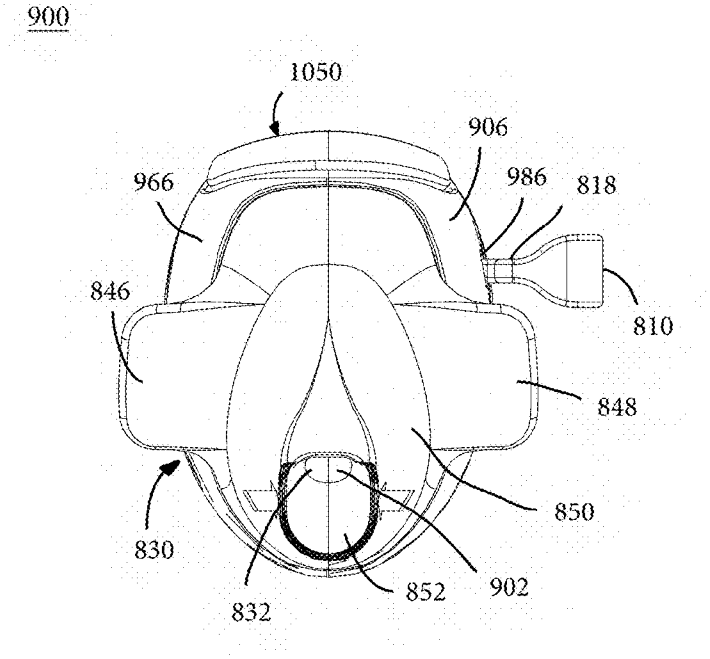
FIG. 60 is a first end view of the release instrument of FIG. 54, in accordance with an aspect of the present disclosure.
Figure 61:
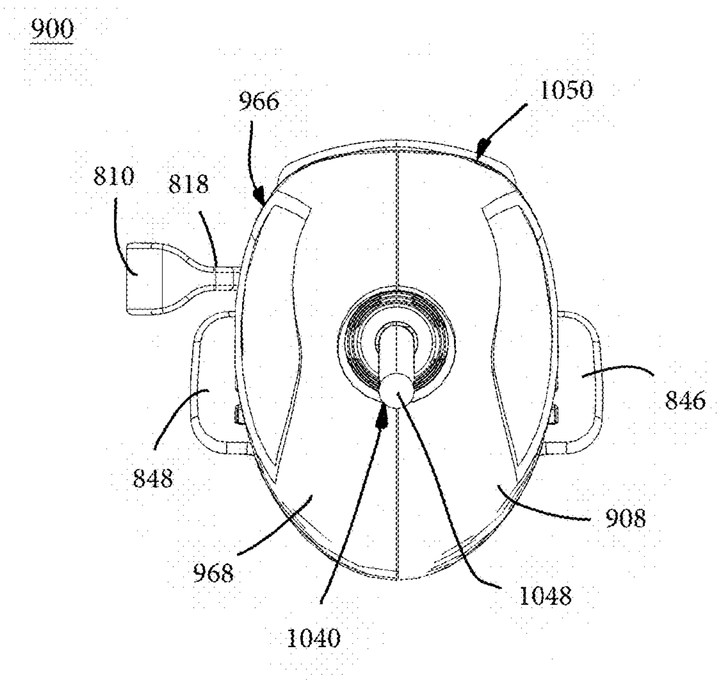
FIG. 61 is a second view of the release instrument of FIG. 54, in accordance with an aspect of the present disclosure.
Figure 62:
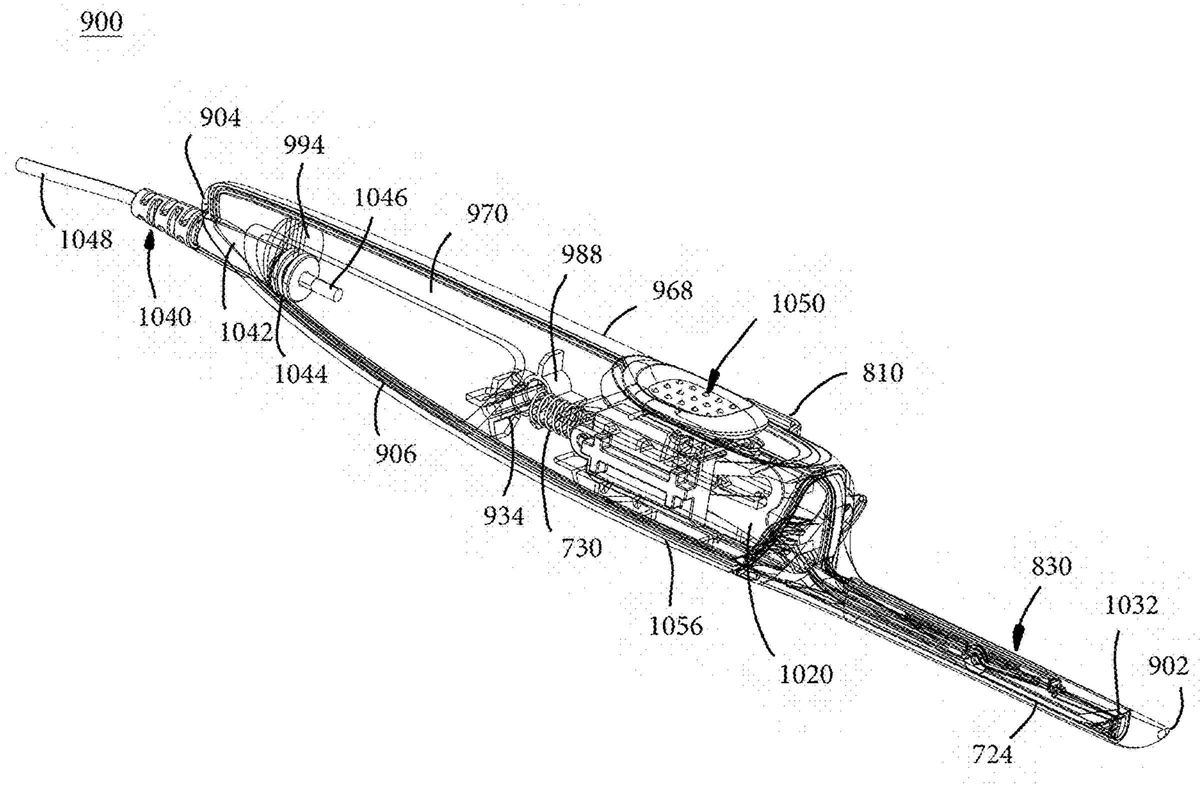
FIG. 62 is a perspective view of the release instrument of FIG. 54 with a transparent first housing and cannula, in accordance with an aspect of the present disclosure.
Figure 63:
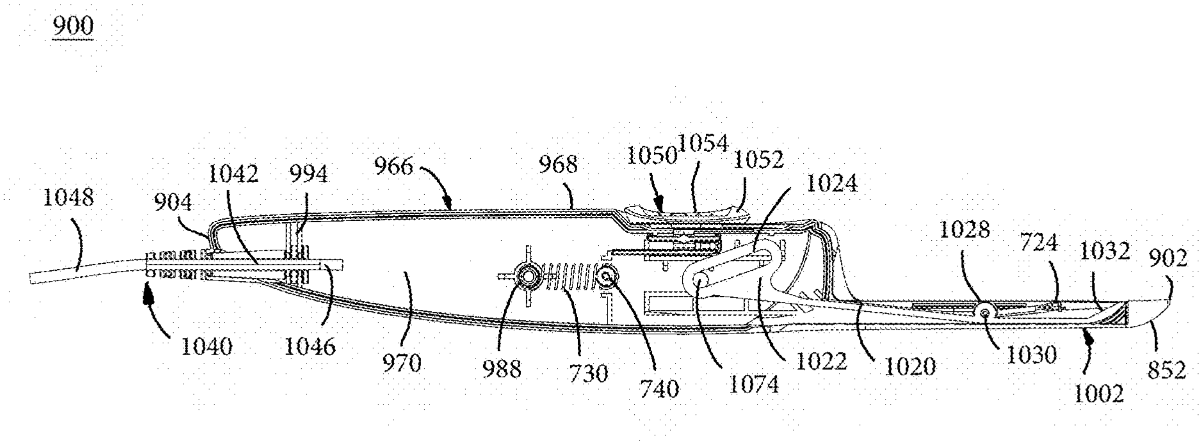
FIG. 63 is a cross-sectional, side view of the release instrument of FIG. 54 taken along line 63-63 in FIG. 58, in accordance with an aspect of the present disclosure.
Figure 64:
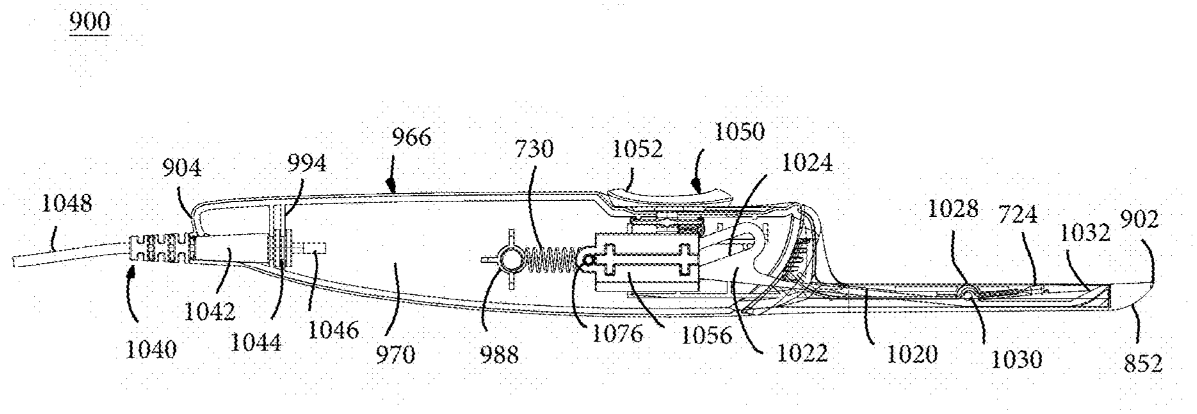
FIG. 64 is a side view of the release instrument of FIG. 54 with the first housing removed and a transparent cannula, in accordance with an aspect of the present disclosure.
Figure 65:
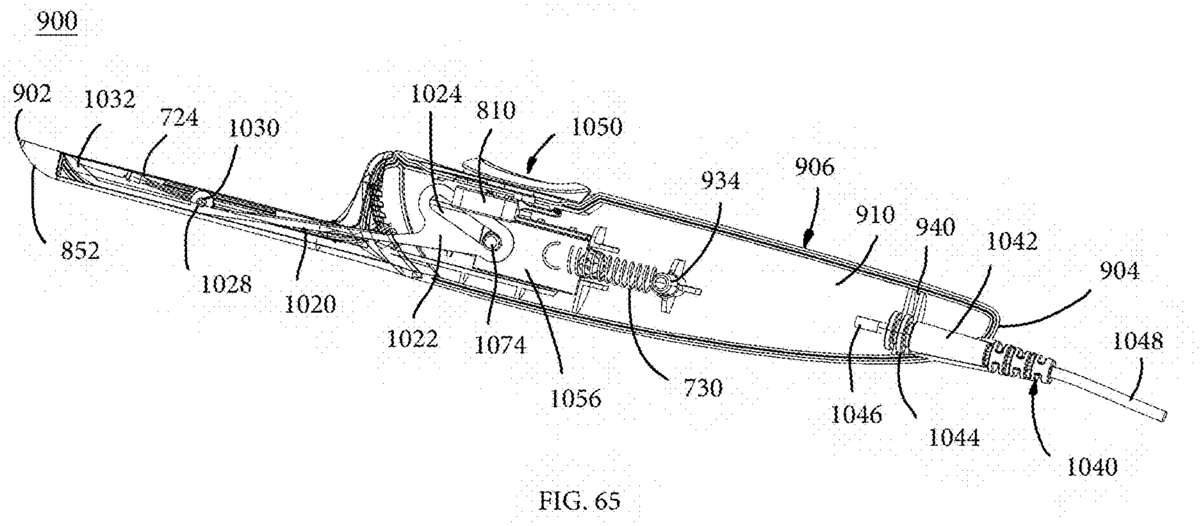
FIG. 65 is a perspective view of the release instrument of FIG. 54 with the second housing removed and a transparent cannula, in accordance with an aspect of the present disclosure.

The sheath portion or blade holder 952 may also be seen in FIGS. 57-58. The sheath portion 952 is coupled to and extends from the first end 914 of the handle portion 912. The sheath portion 952 may include a blade region 954 inset into a portion of the interior of the sheath portion 952. The blade region 954 may extend from the opening 946 to a position near the first end 902 of the release instrument 900. The blade region 954 may be, for example, inset into the sheath portion 952 of the first housing 906 the entire width of the blade member 1020 or only a portion of the width of the blade member 1020. The sheath portion 952 may also include a blade slot 956 extending from the blade region 954 at a bottom of the sheath portion 952 to a top of the sheath portion 952. The blade slot 956 may be, for example, angled or curved as it extends from the blade region 954 to a position near the first end of the sheath portion 952. The blade slot 956 may be, for example, configured or size and shaped to correspond to the shape of the blade 1032. In addition, the sheath portion 952 may include a hinge member 958 extending away from an interior surface of the sheath portion 952 along the blade region 954. The hinge member 958 may be positioned near a midpoint between the first and second ends of the sheath portion 952. The hinge member 958 allows for pivoting or rotation of the blade member 1020 during deployment and retraction of the blade 1032 during a surgical procedure. The pivoting or rotation movement of the blade member 1020 may be as described above with reference to blade 300 which will not be described again here for brevity's sake.

The sheath portion 952 may also include a cable channel 960 extending through the first end 914 of the first housing 906 and inset into the sheath portion 952, as shown in FIGS. 67-68. The cable channel 960 may be inset into the sheath portion 952 more than the blade region 954. A portion of the cable channel 960 may overlap with a portion of the blade region 954 where the blade 1032 is deployed from the sheath portion 952 of the first housing 906. The sheath portion 952 also includes a camera slot 962 for receiving a camera connector 722 and a camera 724. The slot 962 may be, for example, configured or sized and shaped to correspond the camera or camera sensor 724 being used in the release instrument 900. The sheath portion 952 further includes a camera opening 964 at the first end extending from an exterior surface of the sheath portion 952 into the camera slot 962. The opening 964 provides a window for the camera 724 to view the surrounding tissues and other structures during surgery.

Figure 66:
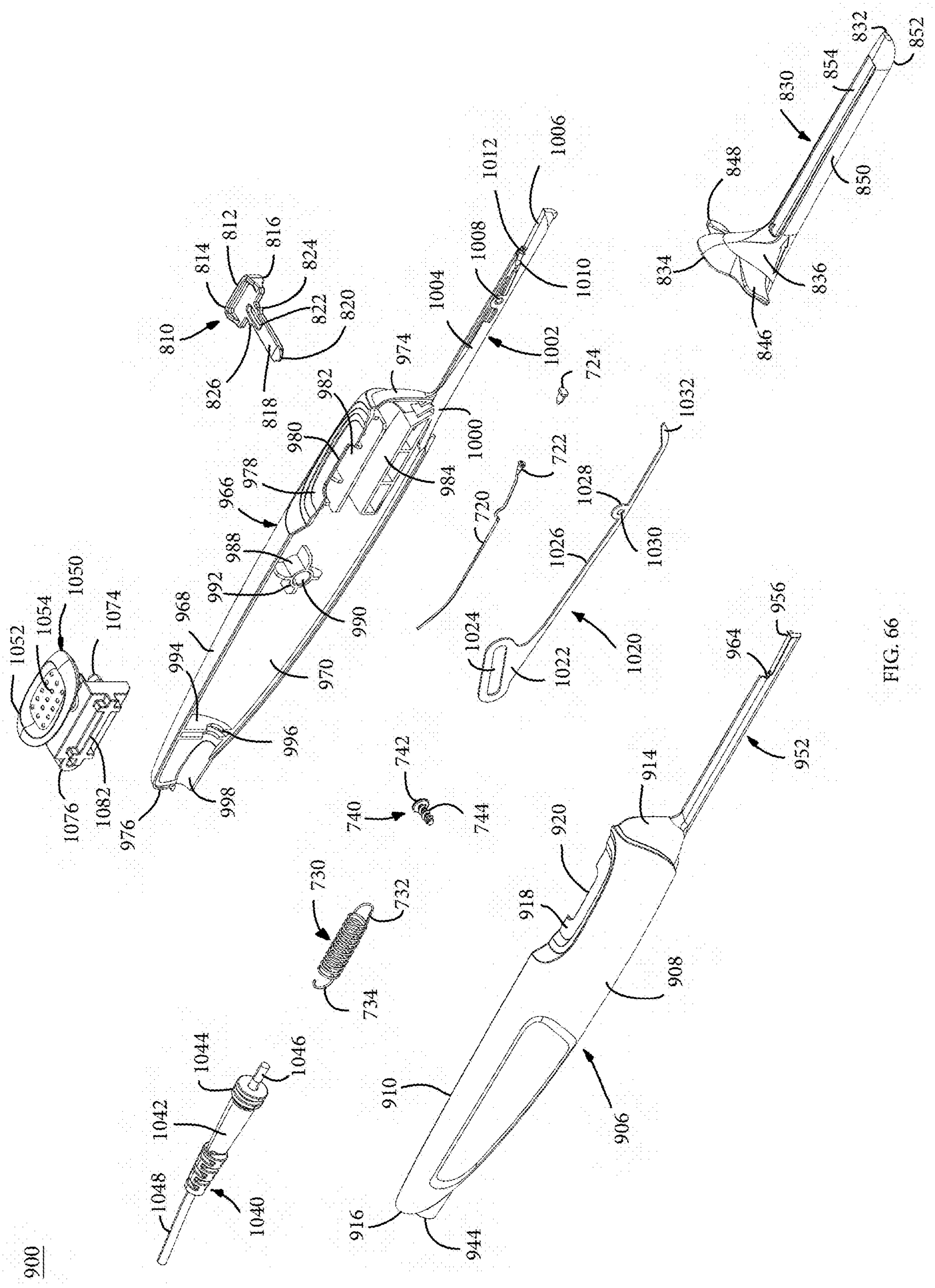
FIG. 66 is a first exploded, perspective view of the release instrument of FIG. 54, in accordance with an aspect of the present disclosure.
Figure 69:
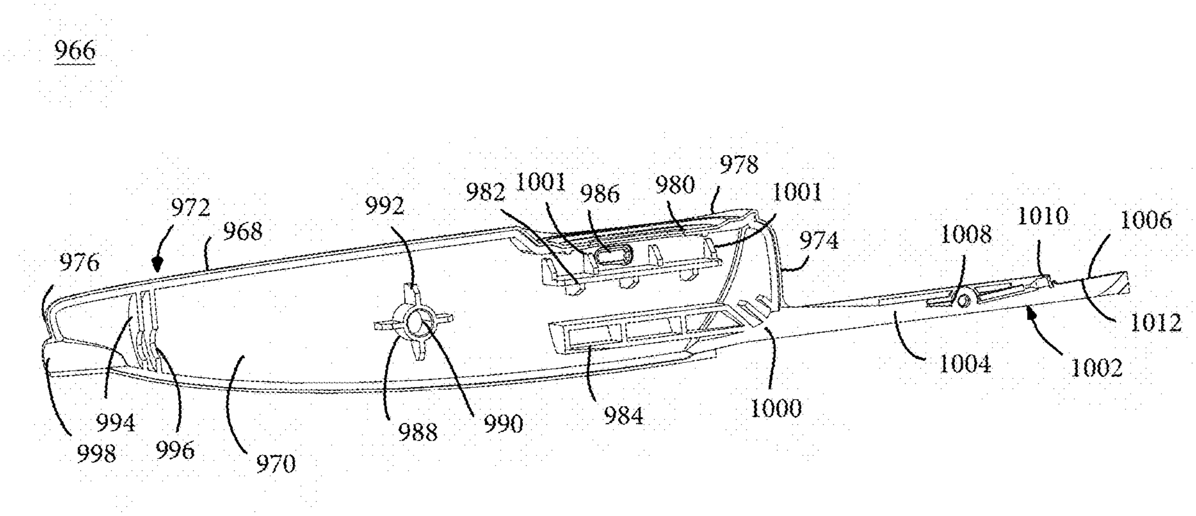
FIG. 69 is a perspective, side view of the second housing of the release instrument of FIG. 54, in accordance with an aspect of the present disclosure.

Referring now to FIGS. 66 and 69, the second housing 966 is shown. The second housing 966 includes an exterior surface 968 and an interior surface 970. The second housing 966 also includes a handle portion 972 and a sheath portion 1002 coupled to and extending away from the handle portion 972. The handle portion 972 may include a first end 974 and a second end 976 opposite the first end 974. The sheath portion 1002 may extend away from the first end 974 of the handle portion 972. The second housing 966 and sheath portion 972 may be, for example, a singular integral or monolithic piece (i.e., of one-piece construction), or may be formed from a plurality of components that are coupled (e.g., rigidly coupled) together to form the second housing 966. The second housing 966 may also include a recessed region 978 extending into a top surface of the second housing 966. The second housing 966 may further include an opening 980 extending from the exterior surface 968 of the second housing 966 into the interior surface 970 through the recessed region 978. The recessed region 978 and opening 980 are mirror images of the recessed region 918 and opening 920, respectively, of the first housing 906. The recessed region 978 and recessed region 918 couple together to form a single recessed region 918, 978 for receiving a portion of the switch 1050. The opening 980 and opening 920 couple together to form a single opening 920, 980 for receiving a portion of the switch 1050 as it extends from the exterior surfaces 908, 968 to the interior surfaces 910, 970 of the release instrument 900. The switch 1050 may be positioned to engage the recessed regions 918, 978 and the openings 920, 980.

The interior surface 970 also includes a first support structure or upper support 982 and a second support structure or lower support 984, as shown in FIGS. 66 and 69. The upper support structure 982 includes horizontal and vertical members. For example, the upper support structure 982 includes a horizontal member and a plurality vertical members. The plurality of vertical members may, for example, extend away from a top surface of the horizontal member and the bottom surface of the horizontal member. The horizontal member and two first vertical members may be connected to form a slot positioned superior to the horizontal member. The slot may be, for example, configured or sized and shaped to receive a portion of the safety tab 810 when inserted into the release instrument 900 to secure the blade 1032 in one of a deployed or undeployed position. The lower support structure 984 includes two horizontal members and a plurality of vertical members. The vertical members are coupled to a first horizontal member on a first end and a second horizontal member on a second end. The vertical members divide the lower support 984 into multiple cavities. At least one cavity may be, for example, configured or sized and shaped to receive a post 1074 that can translate within the cavity. The upper support 982 and lower support 984 each have, for example, approximately the same length. In addition, the upper support 982 and lower support 984 are each configured or sized and shaped to allow for the blade member 1020 to translate past the surfaces of the supports 982, 984.

With continued reference to FIGS. 66 and 69, the second housing 966 includes a through hole or safety tab hole 986 extending through the second housing 966 from the exterior surface 968 to the interior surface 970. The through hole 968 may be positioned inferior to the recessed region 978 and opening 980. The through hole 968 may be, for example, configured or sized and shaped to receive a shaft 818 of the safety tab 810. In addition, the second housing 966 includes a female coupling member 988 positioned on and extending away from the interior surface 970 of the second housing 966 toward the interior surface 970 of the first housing 906. The coupling member 988 may have, for example, a cylindrical shape and leg members 992 extending away from an exterior surface of the female coupling member 988. The coupling member 988 may also include an opening 990 extending into the female coupling member 988 from the open side of the second housing 966. The opening 990 may be, for example, configured or sized and shaped to receive a portion of the male coupling member 934. The coupling member 988 has a width extending from the interior surface 970 of the second housing 966 toward an interior surface 910 of the first housing 906. The width of the coupling member 988 is smaller than the width of the second housing 966.

Further, the interior surface 970 includes at least one cable support member 994, as shown in FIGS. 66 and 69. The at least one cable support member 994 may be, for example, two support members 994. Each of the at least one cable support members 994 may extend away from the interior surface 970 of the second housing 966 near the second end 976. The support members 994 may include a recess 996 inset into a portion of the support members 994 from the open side of the second housing 966 toward the interior surface 970 of the second housing 966. The recesses 996 may be, for example, configured or sized and shaped to couple to a portion of the cable attachment member 1040. The second end 976 of the second housing 966 may also include a cable opening 998 positioned adjacent to the at least one support member 994. The cable opening 998 may extend through the second housing 966 from an exterior surface 668 to an interior surface 970 allowing for the cable attachment member 1040 to pass from the interior of the release instrument 900 to the exterior of the release instrument 900.

With continued reference to FIGS. 66 and 69, the second housing 966 also includes a blade arm opening 1000. The opening 1000 is positioned near a first end 974 of the second housing 966. In addition, the opening 1000 is positioned near a bottom surface of the second housing 966. The opening 1000 is, for example, configured or sized and shaped to receive a portion of the blade arm 1026 as the blade arm 1026 extends from the handle portion 972 of the second housing 966 to the sheath portion 1002 of the second housing 966. In addition, the interior surface 970 of the handle portion 972 of the second housing 966 includes at least one tab 1001 extending away from the interior surface 970 inferior to the recessed region 978. The at least one tab 1001 may include a first tab 1001 positioned toward the first end 974 and a second tab 1001 positioned toward the second end 976. In addition, the first tab 1001 is positioned near a first end of the opening 980 and the second tab 1001 is positioned near a second end of the opening 980. The tabs 1001 may have, for example, a semi-circular shape and may extend the entire width of the wall at the top of the second housing 966. The tabs 1001 may be, for example, configured or sized and shaped to engage a portion of the switch 1050.

The sheath portion or blade holder 1002 may also be seen in FIGS. 66 and 69. The sheath portion 1002 is coupled to and extends from the first end 974 of the handle portion 972. The sheath portion 1002 may include a blade region or channel 1004 inset into a portion of the interior of the sheath portion 1002. The blade region 1004 may extend from the opening 1000 to a first end 902 of the release instrument 900. The blade region 1004 may be, for example, inset into the sheath portion 1002 of the second housing 966 the entire width of the blade member 1020 or only a portion of the width of the blade member 1020. When assembled the blade regions 954, 1004 combine together to form a blade region 954, 1004 that is at least as large as the width of the blade member 1020 to allow for translation of the blade arm 1026 through the blade region 954, 1004. The sheath portion 1002 may also include a blade slot 1024 extending from the blade region 1004 at a bottom of the sheath portion 1002 to a top of the sheath portion 1002. The blade slot 1024 is angled or curved as it extends from the blade region 1004 to a position near the first end of the sheath portion 1002. The blade slot 1024 may be, for example, configured or size and shaped to correspond to the shape of the blade 1032. The sheath portion 1002 also includes a camera slot 1010 for receiving a camera connector 722 and a camera or camera sensor 724. The slot 1010 may be, for example, configured or sized and shaped to correspond the camera 724 being used in the release instrument 900. The sheath portion 1002 further includes a camera opening 1012 at the first end extending from an exterior surface of the sheath portion 1002 into the camera slot 1010. The opening 1012 provides a window for the camera 724 to view the surrounding tissues and other structures during surgery.

Referring now to FIGS. 62-67, the blade member 1020 is shown. The blade member 1020 includes a base 1022, an arm 1026 coupled to the base 1022 on a first end, and a blade 1032 coupled to the arm 1026 on a second end. The blade member 1020 may also include a hinge member 1028 extending from the arm 1026 between the first end and the second end of the arm 1026. The base 1022 may have, for example, an oval shape. The base 1022 may also include a slot 1024 extending through the base 1022 from a first side to a second side. The slot 1024 may be, for example, angled or slanted as it extends from a first end to a second end. The angle of the slot 1024 may, for example, correspond to the desired rotation or pivoting of the blade 1032. The slot 1024 may also be configured or sized and shaped to receive at least a portion of the post 1074 of the switch 1050, as described in greater detail below. The arm 1026 extends away from the first end of the base 1022 and the arm 1026 may include, for example, angles or curves along the length of the arm 1026. The arm 1026 may be, for example, positioned at and coupled to a bottom or inferior end of the base 1022. The blade member 1020 may also include a blade or cutting end 1032 coupled to and extending from a second end of the arm 1026. The cutting end 1032 may extend from the arm 1026 at an angle greater than 0° and less than 90°, more preferably the angle is between 25° and 40°, and most preferably the angle is between 30° and 35°. The cutting end 1032 includes a sharp surface for cutting through tendinous, ligamentous, fibrous tissue, and the like. The cutting end 1032 may have, for example, a larger height and a smaller length than the arm 1026. The blade member 1020 may be, for example, a singular integral or monolithic piece (i.e., of one-piece construction), or may be formed from a plurality of components that are coupled (e.g., rigidly coupled) together to form the blade member 1020. The hinge member 1028 of the blade member 1020 may pivot or rotate about the hinge member 958 of the first housing 906 as the base 1022 of the blade member 1020 translates along the post 1074 of the switch 1050. As the blade member 1020 pivots or rotates about hinge member 958 to deploy and retract the blade 1032 from the cannula 830 of the release instrument 900.

With continued reference to FIGS. 62-67, the camera cable 720 is coupled to the camera connector 722 on a first end and the cable attachment member 1040 on a second end. The cable 720 extends from the camera slots 962, 1010 through the channel 960, into and through the handle portions 912, 972, and finally couples to the cable attachment member 1040 at a second end 904 of the release instrument 900. As the cable 720 extends through the handle portions 912, 972 the cable 720 is positioned to prevent engagement with the other components positioned inside the handle portions 912, 972 of the release instrument 900. The cable 720 may be, for example, at least one wire and/or cable to transmit power to the camera 724 and/or video to a display or a processor of the video unit 102. The at least one wire and/or cable 720 may be, for example, a single wire or separate wires for the camera 724. The camera connector 722 is positioned in the camera slot 962, 1010 and couples to a camera or camera sensor 724 also positioned in the camera slot 962, 1010. The camera 724 is positioned to align the lens of the camera with the openings 964, 1012 to allow for visualization of the surgical field during a procedure. The images collected by the camera 724 are transmitted to a video output through the cables 720, 1048.

Also shown in FIGS. 62-67 the first end 732 of the spring 730 has a first hook that is coupled to a portion of the switch 1050 by a screw 740. The second end 734 of the spring 730 has a second hook that is coupled to an exterior surface 936 of the male coupling member 934. The spring 730 expands and compresses during translation of the switch 1050. The head 742 of the screw 740 engages the first end 732 of the spring 730 to secure the first end 732 of the spring 730 between the head 742 and the switch 1050. The shaft 742 of the screw 740 is coupled to a through hole 1080 in the switch 1050.

The cable attachment member 1040 is shown in FIGS. 54-59 and 61-67. The attachment member 1040 includes a housing or strain relief portion 1042 including a plurality of recesses 1044 inset into the exterior surface of the housing 1042. The plurality of recesses 1044 have a shape that corresponds to the shapes of the recesses 942, 996 in the cable support portions 940, 994 of the housings 906, 966 of the release instrument 900. For example, the recesses 942, 996 may have circular or semi-circular shapes to correspond to the semi-circular shapes of the recesses 942, 996 of the cable supports 940, 994. The attachment member 1040 also includes a connector 1046 coupled to and extending from a first end of the housing 1042. The attachment member 1040 further includes a cable 1048 coupled to and extending from the second end of the housing 1042. A portion of the housing 1042 may be positioned in the cable opening 944, 998.

Referring now to FIGS. 54-72, and more particularly to FIGS. 66, 67 and 70-72, the switch 1050 is shown. The switch 1050 includes a button 1052 coupled to a base 1056 by a stem or connecting member 1090. The button 1052 includes a recessed region 1054 on a top surface that may include a textured region. The button 1052 and recessed region 1054 are, for example, configured or sized and shaped to receive a user's finger to translate the button 1052 and in turn deploy and retract the blade 1032 from the insertion instrument 900. The connecting member 1090 extends through the openings 920, 980 in the housings 906, 966. The button 1052 is coupled to a first end of the connecting member 1090 to position the button 1052 over the recessed regions 918, 978 and spaced apart from the exterior surfaces 908, 968 the housings 906, 966. The base 1056 is coupled to a second end of the connecting member 1090. The base 1056 is also positioned within the interior surfaces 910, 970 of the housings 906, 966. The base 1056 includes a first side 1058 opposite a second side 1060, a first end 1062 opposite a second end 1064, and a top 1066 opposite a bottom 1068. The first side 1058 includes a recessed region 1070 extending from an exterior surface into a portion of the base 1056. The recessed region 1070 may be, for example, configured or sized and shaped to receive the base 1022 of the blade member 1020. The recessed region 1070 may form a rim or wall across the top 1066 of the first side 1058 of the base 1056 to assist with retaining the blade member 1020 within the recessed region 1070. The first side 1058 may also include a post 1074 extending away from the first side 1058 of the base 1056. The post 1074 may be moveably coupled to the slot 1024 of the base 1022 of the blade member 1020.

The base 1056 may further include a tab 1076 extending away from the second end 1064 of the base 1056. The tab 1076 may include an exterior surface 1078 and a through hole 1080. The through hole 1080 extending through the tab 1076 from the exterior surface 1078 on a first side to the exterior surface 1078 on a second side. The through hole 1080 may be, for example, threaded to receive the threaded shaft 744 of the screw 740 to secure the first end of the spring 730 to the tab 786 of the base 1056. The head 742 of the screw 740 may engage a portion of the first side of the exterior surface 1078 and secure the first hook on the first end 732 of the spring 730 between the head 742 and the first side of the tab 1076.

Figure 70:
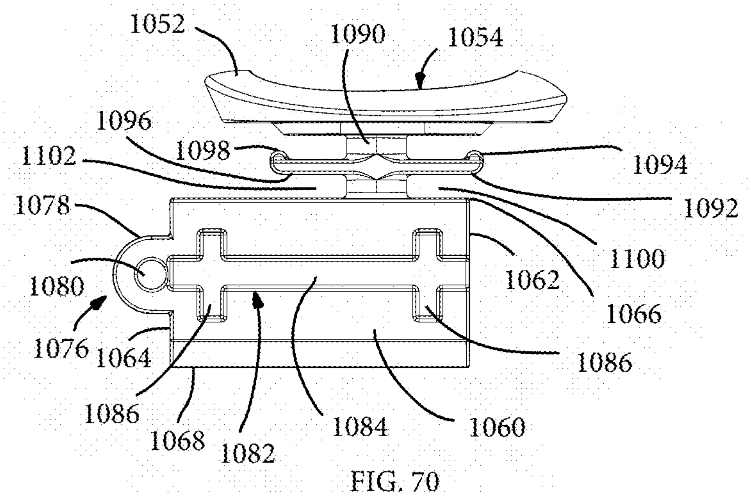
FIG. 70 is a first side view of the switch of the release instrument of FIG. 54, in accordance with an aspect of the present disclosure.
Figure 72:
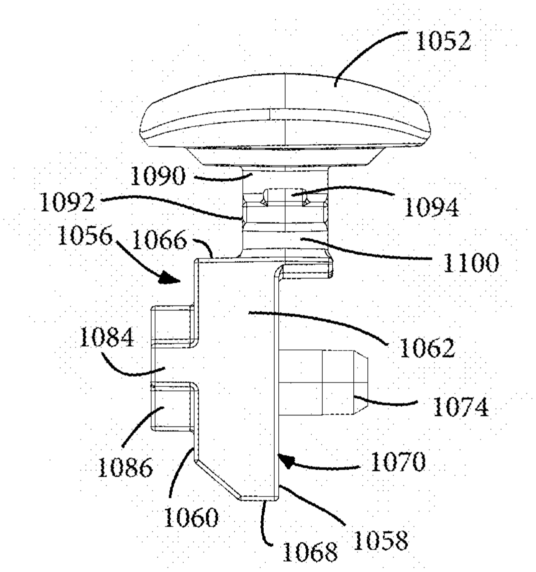
FIG. 72 is a first end view of the switch of the release instrument of FIG. 54, in accordance with an aspect of the present disclosure.

In addition, the base 1056 of the switch 1050 may include a protrusion 1082 extending away from the second side 1060 of the base 1056, as shown in FIGS. 66, 70 and 72. The protrusion 1082 may include a horizontal member 1084 and vertical members 1086. The protrusion 1082 may include, for example, one horizontal member and two vertical members spaced apart from each other along the length of the horizontal member. The vertical members may overlap the horizontal member. The protrusion 1082 may, for example, assist with translation of the switch 1050 relative to the housings 906, 966. The protrusion 1082 may slide along the housing 906 between the upper support 922 and the lower support 924.

The connecting member 1090 of the switch 1050 may also include a first arm or wing 1092 and a second arm or wing 1102, as shown in FIGS. 66, 67, 70 and 71. The first arm 1092 extends from the connecting member 1090 in the direction of the first end 1062 of the base 1056. The first arm 1092 may be, for example, positioned near a midpoint between a top surface 1066 of the base 1056 and a bottom surface of the button 1052. The first arm 1092 may also include a first projection 1094 extending away from a top surface of the first arm 1092. The first projection 1094 may extend the entire width of the first arm 1092. The first projection 1094 may be, for example, semi-circular or round shaped. The first projection 1094 may be, for example, configured or sized and shaped to engage the first tabs 948, 1001 on the interior surface 910, 970 of the housings 906, 966. The tabs 948, 1001 and projection 1094 assist with retaining the switch 1050 within the desired range of translation.

The second arm 1096 extends from the connecting member 1090 in the direction of the second end 1064 of the base 1056. The second arm 1096 may be, for example, positioned near a midpoint between the top surface 1066 of the base 1056 and the bottom surface of the button 1052. The second arm 1096 may also include a second projection 1098 extending away from a top surface of the second arm 1096. The second projection 1098 may extend the entire width of the second arm 1096 between the first side and the second side of the second arm 1096. The second projection 1098 may be, for example, semi-circular or round shaped. The second projection 1098 may be, for example, configured or sized and shaped to engage the second tabs 950, 1001 on the interior surface 910, 970 of the housings 906, 966. The tabs 950, 1001 and projection 1098 assist with retaining the switch 1050 within the desired range of translation.

Figure 71:
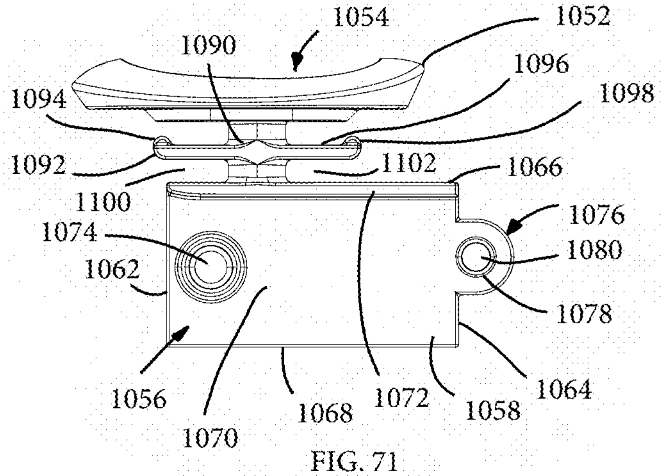
FIG. 71 is a second side view of the switch of the release instrument of FIG. 54, in accordance with an aspect of the present disclosure.

With continued reference to FIGS. 70 and 71, the switch 1050 may also include a first locking channel or undeployed channel 1100 and a second locking channel or deployed locking channel 1102. The first and second locking channels 1100, 1102 are configured and/or sized and shaped to receive a portion of the shaft 818 of the safety tab 810. The first locking channel 1100 is positioned between the top surface 1066 of the base 1056 and a bottom surface of the first arm 1092. The second locking channel 1102 is positioned between the top surface 1066 of the base 1056 and a bottom surface of the second arm 1096. When the safety tab 810 is inserted into the first locking channel 1100 the switch 1050 is secured in a first position or undeployed position. When the safety tab 810 is inserted into the second locking channel 1102 the switch 1050 is secured in a second position or deployed position.

Referring now to FIGS. 54-67, the cannula 830 is shown. The second end 834 is configured and/or sized and shaped to couple to the first and second housings 906, 966. The recess 844 may be, for example, configured and/or sized and shaped to receive a corresponding protrusion of the coupled housings 906, 966 of the release instrument 900. The wings 846, 848 of the cannula 830 may, for example, provide for a position to place the user's fingers during insertion, as well as assist with insertion and removal of the cannula 830 onto the coupled housings 906, 966. The channel 854 may open into the through hole 842 to allow for insertion of the coupled sheath portions 952, 1002 for deployment of the blade 1032 for cutting tendinous, ligamentous, fibrous tissue, and the like.

With continued reference to FIGS. 54-67, the camera cable 720 is positioned within the cable channel 960 and the camera slot 962, extends through the handle portion 912 of the first housing 906, and couples to the connector 1046 of the cable attachment member 1040. The camera cable 720 may be, for example, directly coupled to the connector 1046 or indirectly coupled to the connector 1046 with additional electrical components, such as, additional cables, circuit boards, bridge circuit boards, and the like. The camera or camera sensor 724 is coupled to the camera connector 722 and positioned within the camera slot 962. The cable attachment member 1040 is positioned to engage the at least one cable support 942, 996 and extend out of the release instrument 900 through the cable opening 944, 998 formed by the coupled housings 906, 966. The switch or translating member 1050 is positioned within the first housing 906. The post 1074 of the switch 1050 is moveably coupled to the blade support member 1020. The stem 1090 of the switch 1050 is positioned within the opening 920, 980 of the first and second housings 906, 966 to position the base 1056 of the switch 1050 to engage the upper support 922, lower support 924, and the bottom support 926. The tab 1076 of the switch 1050 may receive the screw 740 to couple the first end 732 of the spring 730 to the switch 1050 to allow for the spring 730 to expand and contract when the switch 1050 is translated. The second end 1064 of the switch 1050 engages the male coupling member 934 of the housing 906 through the spring 730 to secure the second end 1064 to the housing 906. The blade member 1020 is positioned adjacent to the base 1056 of the switch 1050 in the recessed region 1054. The post 1074 is inserted into the slot 1024 of the blade member 1020 and the arm 1026 is positioned in the blade region 954, 1004. In addition, the through hole 1030 of the blade member 1020 rotatably engages the hinge member 958 along the sheath 952. When the spring 730 is in an undeployed position the cutting end 1032 is also undeployed. The second housing 966 is coupled to the first housing 906 by aligning and engaging the male coupling member 934 with the female coupling member 988. Specifically, the exterior surface 936 of the male coupling member 934 is inserted into the opening 990 of the female coupling member 988. Once the first housing 906 is coupled to the second housing 966, the connecting member 1090 of the switch 1050 is positioned in the openings 920, 980. The safety tab 810 is then inserted into the through hole 986 of the second housing 966 and engages the locking slot 932 of the first housing 906. The shaft 818 of the safety tab 810 also engages the first locking channel 1100 in the undeployed position. The safety tab 810 may be partially removed from the coupled housings 906, 966 to disengage the shaft 818 from the first locking channel 1100. The switch 1050 may be translated to deploy at least a portion of the cutting end 1032 of the blade member 1020 above cannula 830. Then, the safety tab 810 may be released to engage the shaft 818 with the second locking channel 1102. After the cutting is complete, the safety tab 810 may be removed from the second locking channel 1102 and the switch 1050 translated back to retract the blade member 1020 to the undeployed position. Once in the undeployed position, the safety tab 810 may be reinserted into the first locking channel 1102.

Once assembled, the blade 1032 will be positioned in an undeployed position. The release instrument 900 can then be positioned for a release procedure. Once in position, as confirmed with the camera 724 and display 102, the blade 1032 may be moved to a second deployed position. The blade 1032 may be moved by rotating or pivoting the blade 1032 about the hinge member 958 of the sheath portion 952 of the first housing 906. The blade 1032 may be rotated by translating the switch 1050 from the first undeployed position to the second deployed position. As the switch 1050 is translated, the post 1074 of the switch 1050 translates within the slot 1024 of the blade member 1020 from a first end to a second end, thereby rotating the blade member 1020 about the hinge member 958. As the blade member 1020 is rotated or pivoted the cutting end 1032 extends above the top of the cannula 830. Once the cutting end 1032 is exposed the housings 906, 966 may be translated along the cannula 830 to perform the cut. After the cut is made, the switch 1050 may be translated in the opposite direction and the cutting end 1032 may pivot or rotate back to the undeployed position.

For a carpal tunnel release procedure, the surgical method may include making a single limited incision in the wrist flexor crease. Then, the insertion instrument 110, 350, 260, 450, 600, 900 is inserted until the deep side of the transverse carpal ligament (TCL) is directly visualized at the tip of the instrument 110, 350, 260, 450, 600, 900. At that point the cannula 140, 410, 830 remains stationary and the handpiece 120, 360, 270, 460, 606, 662, 906, 966, with the camera unit 190 provides a full length view of the entire carpal canal. Next, the surgeon actuates the cutting blade to either perform a forward cut with the insertion instrument 110, 350, 600 or a rearward cut with the insertion instrument 260, 450, 900 by translating the handpiece 120, 360, 270, 460, 606, 662, 906, 966 within the cannula 140, 410, 830. Once the cut is complete, the instrument 110, 350, 260, 450, 600, 900 is removed from the incision.

As may be recognized by those of ordinary skill in the art based on the teachings herein, numerous changes and modifications may be made to the above-described and other embodiments of the present disclosure without departing from the scope of the disclosure. The instruments, devices, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, devices, and systems may include more or fewer components or features than the embodiments as described and illustrated herein. For example, the components and features of the compression anchor systems of FIGS. 1-13, FIGS. 14-26, FIGS. 27-30, FIGS. 31-34, FIGS. 35-53, and FIGS. 54-72 may all be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A videoscopic arthroscopic system, comprising:
- a release instrument including a blade and at least one camera sensor, wherein the release instrument further comprises:
  - a handpiece with a first end and a second end, wherein the handpiece comprises:
    - at least one handle portion;
    - at least one sheath portion coupled to and extending from the at least one handle portion to a first end of the release instrument; and
  - a blade member including the blade at one end, wherein the blade member is a single monolithic piece; and a cannula with a first end and a second end, wherein the at least one sheath portion of the handpiece is slidingly received within the cannula;

wherein the at least one sheath portion comprises:

a blade channel extending through the at least one sheath portion, wherein the blade member is positioned within and translates within the blade channel; and a camera slot extending through the at least one sheath portion from a first end to a second end of the at least one sheath portion, wherein the at least one camera sensor is positioned within the camera slot and extends from the first end of the at least one sheath portion to the second end of the at least one sheath portion, and wherein the blade channel and the camera slot are spaced apart from each other within the at least one sheath portion;

wherein the blade member and the at least one camera sensor positioned within the at least one sheath portion translate together as the at least one sheath portion translates within the cannula, and wherein the blade of the blade member deploys and retracts from the at least one sheath portion and the cannula;

wherein the blade member further comprises:

a base;

an arm coupled to and extending away from the base at a first end; and the blade of the release instrument at a second end of the arm; and wherein the handpiece further comprises:

a blade support member coupling the blade member to a portion of the handpiece;

wherein the blade support member is coupled to and extending from an interior surface of a first housing of the handpiece, and wherein an opening extending through the base of the blade member from a first side to a second side of the base of the blade member, wherein the opening of the base of the blade member slidingly engages the blade support member, wherein the opening extends perpendicularly through the base of the blade member, and wherein the opening is angled as it extends from a first end to a second end of the base of the blade member; and a video unit electrically coupled to the release instrument.

2. The system of claim 1, wherein the handpiece comprises:

the first housing; and a second housing coupled to the first housing.

3. The system of claim 2, wherein the first housing comprises:

a first handle portion of the at least one handle portion extending from a second end of the release instrument toward the first end of the release instrument; and a first sheath portion of the at least one sheath portion coupled to and extending from the first handle portion to the first end of the release instrument; and wherein the second housing comprises:

a second handle portion of the at least one handle portion extending from the second end of the release instrument toward the first end of the release instrument; and a second sheath portion of the at least one sheath portion coupled to and extending from the second handle portion to the first end of the release instrument.

4. The system of claim 3, wherein the first sheath portion of the first housing and the second sheath position of the second housing couple together and are slidably received within a channel of the cannula.

5. The system of claim 2, further comprising:

a translating member moveably coupled to the first housing and the second housing.

6. The system of claim 5, wherein the translating member comprises:

a base positioned within the coupled first and second housings;

a connecting member with a first end and a second end, wherein the first end is coupled to the base; and a button coupled to the second end of the connecting member and positioned superior to an exterior surface of the coupled first and second housings;

wherein the translating member deploys and retracts the blade of the blade member from the at least one sheath portion and cannula.

7. The system of claim 6, wherein at least a portion of the connecting member is positioned in an opening extending through the first and second housings from the exterior surface to an interior surface.

8. The system of claim 7, wherein the second housing further comprises:

a through hole extending through the second housing from the exterior surface to an interior surface near a top surface of the second housing.

9. The system of claim 8, further comprising:

a locking member coupled to the handpiece, wherein a shaft of the locking member is inserted into the through hole in the second housing and the shaft engages a portion of the translating member.

10. The system of claim 6, wherein the blade support member is a post extending away from a first side of the translating member.

11. The system of claim 10, wherein the blade member further comprises:

a hinge member extending from the arm between the first end and the second end of the arm, and wherein the hinge member includes an opening extending through the hinge member from a first side to a second side, wherein the opening of the hinge member of the arm of the blade member is pivotably coupled to a protrusion extending from the sheath portion of the first housing.

12. The system of claim 6, further comprising:

a spring coupled to the interior surface of the first housing on a first end and to the translating member on a second end.

13. The system of claim 1, wherein the video unit is selected from at least one of a video display and a video processor, and wherein the video unit is coupled to the release instrument by a cable.

14. The system of claim 1, wherein the camera slot is positioned distal to the blade channel.

15. A release instrument, comprising:

a handpiece with a first end and a second end, wherein the handpiece comprises:

a handle portion extending from a second end of the handpiece towards the first end; and a sheath portion extending from the handle portion to the first end of the handpiece;

a translating member moveably coupled to the handle portion;

a blade member moveably coupled to the translating member, wherein the blade member is a single monolithic piece; and a cannula with a first end and a second end, wherein the sheath portion of the handpiece is slidingly received with the cannula, and wherein the translating member moves the blade member moves from an undeployed position to a deployed position;

wherein the sheath portion comprises:

a blade channel extending through the sheath portion, wherein the blade member is positioned within and translates within the blade channel; and a camera slot extending through the sheath portion from a first end to a second end of the sheath portion, wherein at least one camera sensor is positioned within the camera slot and extends from the first end of the sheath portion to the second end of the sheath portion, and wherein the blade channel and the camera slot are spaced apart from each other within the sheath portion;

wherein the blade member further comprises:

a base;

an arm coupled to and extending away from the base at a first end; and the blade member of the release instrument at a second end of the arm; and wherein the handpiece further comprises:

a blade support member coupling the blade member to a portion of the handpiece;

wherein the blade support member is coupled to and extending from an interior surface of a first housing of the handpiece, and wherein an opening extending through the base of the blade member from a first side to a second side of the base of the blade member, wherein the opening of the base of the blade member slidingly engages the blade support member, wherein the opening extends perpendicularly through the base of the blade member, and wherein the opening is angled as it extends from a first end to a second end of the base of the blade member.

16. The release instrument of claim 15, wherein the handle portion comprises a first handle portion coupled to a second handle portion, and wherein the sheath portion comprises a first sheath portion and a second sheath portion.

17. A surgical method for releasing tissue, comprises:

obtaining a videoscopic arthroscopic system, wherein the videoscopic arthroscopic system, comprises:

a release instrument including a blade and at least one camera sensor, wherein the blade and the at least one camera sensor translate together, wherein the release instrument further comprises:

a handpiece with a first end and a second end, wherein the handpiece comprises:

at least one handle portion;

at least one sheath portion coupled to and extending from the at least one handle portion to a first end of the release instrument; and a blade member including the blade at one end, wherein the blade member is a single monolithic piece; and a cannula with a first end and a second end, wherein at least one sheath portion of the handpiece is slidingly received within the cannula;

wherein the blade and the at least one camera sensor translate together relative to the cannula, and wherein the blade deploys and retracts from at least the cannula;

wherein the at least one sheath portion comprises:

a blade channel extending through the at least one sheath portion, wherein the blade member is positioned within and translates within the blade channel; and a camera slot extending through the at least one sheath portion from a first end to a second end of the at least one sheath portion, wherein the at least one camera sensor is positioned within the camera slot and extends from the first end of the at least one sheath portion to the second end of the at least one sheath portion, and wherein the blade channel and the camera slot are spaced apart from each other within the at least one sheath portion;

wherein the blade member further comprises:

a base;

an arm coupled to and extending away from the base at a first end; and the blade of the release instrument at a second end of the arm; and wherein the handpiece further comprises:

a blade support member coupling the blade member to a portion of the handpiece;

wherein the blade support member is coupled to and extending from an interior surface of a first housing of the handpiece, and wherein an opening extending through the base of the blade member from a first side to a second side of the base of the blade member, wherein the opening of the base of the blade member slidingly engages the blade support member, wherein the opening extends perpendicularly through the base of the blade member, and wherein the opening is angled as it extends from a first end to a second end of the base of the blade member; and a video unit electrically coupled to the release instrument;

creating an incision in a patient;

inserting a release instrument into the incision;

using the at least one camera sensor of the release instrument to position the blade adjacent to the tissue to be cut;

deploying the blade from the release instrument;

translating the handpiece of the release instrument within the cannula to translate the blade to cut the tissue to be cut;

removing the release instrument; and completing the procedure.

* * * * *